United States Patent
Peruzzi et al.

(10) Patent No.: US 12,385,067 B2
(45) Date of Patent: Aug. 12, 2025

(54) COMPOSITIONS AND THERAPEUTIC METHODS OF microRNA GENE DELIVERY

(71) Applicant: The Brigham and Women's Hospital, Inc., Boston, MA (US)

(72) Inventors: Pierpaolo Peruzzi, Newton, MA (US); Ennio Antonio Chiocca, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 18/441,280

(22) Filed: Feb. 14, 2024

(65) Prior Publication Data

US 2024/0240202 A1 Jul. 18, 2024

Related U.S. Application Data

(63) Continuation of application No. 17/051,527, filed as application No. PCT/US2019/029988 on Apr. 30, 2019, now Pat. No. 11,946,064.

(60) Provisional application No. 62/664,362, filed on Apr. 30, 2018.

(51) Int. Cl.
| | |
|---|---|
| *C12N 15/86* | (2006.01) |
| *A61K 45/06* | (2006.01) |
| *A61K 48/00* | (2006.01) |
| *C12N 15/113* | (2010.01) |
| *C12Q 1/68* | (2018.01) |

(52) U.S. Cl.
CPC .............. *C12N 15/86* (2013.01); *A61K 45/06* (2013.01); *A61K 48/005* (2013.01); *C12N 15/113* (2013.01); *C12N 2310/11* (2013.01); *C12N 2310/141* (2013.01); *C12N 2310/16* (2013.01); *C12N 2310/531* (2013.01); *C12N 2320/30* (2013.01); *C12N 2330/50* (2013.01); *C12N 2750/14143* (2013.01)

(58) Field of Classification Search
None
See application file for complete search history.

(56) References Cited

U.S. PATENT DOCUMENTS

2017/0306326 A1 10/2017 Amendt et al.

FOREIGN PATENT DOCUMENTS

| WO | WO-2010/036939 A2 | 4/2010 |
| WO | WO-2011109380 A1 | 9/2011 |
| WO | WO-2016115033 A1 | 7/2016 |
| WO | WO-2017036351 A1 | 3/2017 |
| WO | WO-2018057855 A1 | 3/2018 |

OTHER PUBLICATIONS

Yang et al (Hepatology, supporting Information, 4 pages, Dec. 2010).*
Bhaskaran et al. "Engineering, delivery, and biological validation of artificial microRNA clusters for gene therapy applications," Nat Protoc. 14(12):3538-3553 (Nov. 2019).
Bhaskaran et al. "The functional synergism of microRNA clustering provides therapeutically relevant epigenetic interference in glioblastoma," Nat Commun. 10:442 (Jan. 2019) (13 pages).
Calloni et al. "Scaffolds for Artificial miRNA Expression in Animal Cells." Hum Gene Ther Methods. 26(5):162-174. (2015).
Extended European Search Report for European Patent Application No. 19796578.3, dated Feb. 3, 2023 (10 pages).
Gabriely et al., "MicroRNA 21 promotes glioma invasion by targeting matrix metalloproteinase regulators," Mol Cell Biol. 28(17):5369-80 (Sep. 2008).
Gao et al., "miRNA oligonucleotide and sponge for miRNA-21 inhibition mediated by PEI-PLL in breast cancer therapy," Acta Biomater. 25:184-93 (Oct. 2015).
International Preliminary Report on Patentability for International Patent Application No. PCT/US2019/029988, issued Nov. 3, 2020 (8 pages).
International Search Report and Written Opinion for International Appliation No. PCT/US2019/029988, dated Oct. 16, 2019 (18 pages).
Kashida et al. "Three-dimensionally designed protein-responsive RNA devices for cell signaling regulation," Nucleic Acids Res. 40(18): 9369-9378 (2012).
Song et al., "miR-218 inhibits the invasive ability of glioma cells by direct downregulation of IKK-β," Biochem Biophys Res Commun. 402(1):135-40 (Nov. 2010).
Sun et al., "Multi-miRNA hairpin method that improves gene knockdown efficiency and provides linked multi-gene knockdown," Biotechniques. 41(1):59-63 (Jul. 2006).
Tamim et al. "Genomic analyses reveal broad impact of miR-137 on genes associated with malignant transformation and neuronal differentiation in glioblastoma cells," PLoS One. 9(1):e85591 (2014) (15 pages).
Yang et al., "Inhibition of hepatitis C virus replication using adeno-associated virus vector delivery of an exogenous anti-hepatitis C virus microRNA cluster," Hepatology. 52(6):1877-87 (Dec. 2010).
Zhou et al., "A tightly regulated Pol III promoter for synthesis of miRNA genes in tandem," available in PMC Nov. 1, 2009, published in final edited form as Biochim Biophys Acta 1779(11):773-9 (2008).

* cited by examiner

*Primary Examiner* — Sean McGarry
(74) *Attorney, Agent, or Firm* — Clark & Elbing LLP

(57) ABSTRACT

Described herein are compositions and methods for treating a disease in a subject by administering delivery vectors that express artificial microRNAs, artificial microRNA clusters, and/or a combination of microRNA clusters and associated non-coding RNAs to the subject. Also described herein are methods for preparing artificial microRNAs and artificial microRNA clusters.

35 Claims, 37 Drawing Sheets
Specification includes a Sequence Listing.

```
                          SEQUENCE LISTING

Sequence total quantity: 21
SEQ ID NO: 1              moltype = DNA  length = 629
FEATURE                   Location/Qualifiers
source                    1..629
                          mol_type = other DNA
                          organism = synthetic construct
SEQUENCE: 1
cttttcaatt tgaagagagt gcttcctctg ttcttaaggg gctagggaac caaattaggt   60
tgtttcaata tcgtgctaaa agatactgcc tttagaagaa ggctattgac aatccagcgt   120
gtctcggtgg aactctgact ccatggttca ctttcatgat ggccacatgc ctcctgccca   180
gagcccggca gccagtccag tgggaagggg ggccgataca ctgtacgaga gtgagtagca   240
ggtctcacag tgaaccggtc tctttcccta ctggacagct gcctcgggaa gccaagttgg   300
gctttaaagt gcagggcctg ctgatgttga gtgcttttg ttggcctctc tctccgtgtt   360
cacagcggac cttgatttaa atgtccatac aattaaggca cgcggtgaat gccaagaatg   420
gggctggcaa cactcctaat ggaatgccgt tatccaaaga gcagcacgaa cccgacaggg   480
ctgagtggct tgtgctaggg agaggtttgt gtcattcctg ctgaccaaac tgcaggaaaa   540
actgctaatt gtcatgctga agactgcctg acggggagac tctgccttct gtaagtaggt   600
catgtaaaga gcacgtgctc cttgctgct                                    629

SEQ ID NO: 2              moltype = DNA  length = 795
FEATURE                   Location/Qualifiers
source                    1..795
                          mol_type = other DNA
                          organism = synthetic construct
SEQUENCE: 2
cttttcaatt tgaagagagt gcttcctctg ttcttaaggg gctagggaac caaattaggt   60
tgtttcaata tcgtgctaaa agatactgcc tttagaagaa ggctattgac aatccagcgt   120
gtctcggtgg aactctgact ccatggttca ctttcatgat ggccacatgc ctcctgccca   180
gagcccggca gccagtccag tgggaagggg ggccgataca ctgtacgaga gtgagtagca   240
ggtctcacag tgaaccggtc tctttcccta ctggacagct gcctcgggaa gccaagttgg   300
gctttaaagt gcagggcctg ctgatgttga gtgcttttg ttggcctctc tctccgtgtt   360
cacagcggac cttgatttaa atgtccatac aattaaggca cgcggtgaat gccaagaatg   420
gggctggcat aagaagttat gtattcatcc aataattcaa gccaagcaag tatataggtg   480
ttttaatagt ttttgtttgc actgactctc ttcggtgacg ggtattcttg ggtggataat   540
acggattacg ttgttattgc ttaagaatac gcgtagtcga ggagagtacc agtgcacact   600
cctaatggaa tgccgttatc caaagagcag cacgaacccg acagggctga gtggcttgtg   660
ctagggagag gtttgtgtca ttcctgctga ccaaactgca ggaaaactg ctaattgtca   720
tgctgaagac tgcctgacgg ggagactctg ccttctgtaa gtaggtcatg taaagagcac   780
gtgctccttg ctgct                                                   795
```

| SEQ ID NO: 3 | moltype = DNA length = 1168 |
| --- | --- |
| FEATURE | Location/Qualifiers |
| source | 1..1168 |
| | mol_type = other DNA |
| | organism = synthetic construct |

SEQUENCE: 3

```
cttttcaatt tgaagagagt gcttcctctg ttcttaaggc tagggaacca aattaggttg    60
tttcaatatc gtgctaaaag atactgcctt tagaagaagg ctattgacaa tccagcgtgt   120
ctcggtggaa ctctgactcc atggttcact ttcatgatgg ccacatgcct cctgcccaga   180
gcccggcagc cagtccagtg ggaaggggg  ccgatacact gtacgagagt gagtagcaga   240
tctcacagtg aaccggtctc tttccctact ggacagctgc ctcgggaagc caagttgggc   300
tttaaagtgc agggcctgct gatgttgagt gcttttgtt  ggcctctctc tccgtgttca   360
cagcggacct tgatttaaat gtccatacaa ttaaggcacg cggtgaatgc caagaatggg   420
gctggcataa gaagttatgt attcatccaa taattcaag  caagcaagta tataggtgtt   480
ttaatagttt ttgtttgcac tgactctctt cggtgacggg tattcttggg tggataatac   540
ggattacgtt gttattgctt aagaatacgc gtagtcgagg agagtaccag tgctatttcc   600
ttcaaatgaa tgattttac  taattttgtg tactttatt  gtgtcgatgt agaatctgcc   660
tggtctatct gatgtgacag cttctgtagt ggaccggctg gccccatctg gaagactagt   720
gattttgttg ttgtcttact gcgctcaaca acaaatccca gtctacctaa tggtgccagc   780
catcgctgct agctgtagaa ctccagcttc ggcctgtcgc ccaatcaaac tgtcctgtta   840
ctgaacacgt gataatgtag cgagattttc tgttgtgctt gatctaacca tgtggttgcg   900
aggtatgaag aaaacatggt tccgtcaagc accatgaagc gtcacgcagc tttctacgtg   960
acactcctaa tggaatgccg ttatccaaag agcagcacga acccgacagg gctgagtggc  1020
ttgtgctagg gagaggtttg tgtcattcct gctgaccaaa ctgcaggaaa aactgctaat  1080
tgtcatgctg aagactgcct gacggggaga ctctgccttc gtaagtagg  tcatgtaaag  1140
agcacgtgct ccttgctgct gcggccgc                                     1168
```

| SEQ ID NO: 4 | moltype = DNA length = 1314 |
| --- | --- |
| FEATURE | Location/Qualifiers |
| source | 1..1314 |
| | mol_type = other DNA |
| | organism = synthetic construct |

SEQUENCE: 4

```
cttttcaatt tgaagagagt gcttcctctg ttcttaaggg gctagggaac caaattaggt    60
tgtttcaata tcgtgctaaa agatactgcc tttagaagaa ggctattgac aatccagcgt   120
gtctcggtgg aactctgact ccatggttca ctttcatgat ggccacatgc ctcctgccca   180
gagcccggca gccagtccag tgggaagggg ggccgataca ctgtacgaga gtgagtagca   240
ggtctcacag tgaaccggtc tctttcccta ctggacagct gcctcgggaa gccaagttgg   300
gctttaaagt gcagggcctg ctgatgttga gtgcttttt  tggcctctc  tctccgtgtt   360
cacagcggac cttgatttaa atgtccatac aattaaggca cgcggtgaat gccaagaatg   420
gggctggcat aagaagttat gtattcatcc aataattcaa gccaagcaag tatataggtg   480
ttttaatagt ttttgtttgc actgactctc ttcggtgacg ggtattcttg gtggataat   540
acggattacg ttgttattgc ttaagaatac gcgtagtcga ggagagtacc agtgctattt   600
ccttcaaatg aatgattttt actaatttg  tgtacttta  ttgtgtcgat gtagaatctg   660
cctggtctat ctgatgtgac agcttctgta gtggaccggc tggccccatc tggaagacta   720
gtgattttgt tgttgtctta ctgcgctcaa caacaaatcc cagtctacct aatggtgcca   780
gccatcgctg ctagctgtag aactccagct tcggcctgtc gcccaatcaa actgtcctgt   840
tactgaacac gtgataatgt agcgagattt tctgttgtgc ttgatctaac catgtggttg   900
cgaggtatga gtaaaacatg gttccgtcaa gcaccatgga acgtcacgca gctttctacg   960
tgaaaagtct gtagaaaagt aagggaaact caaacccctt tcggcagcg  tgagtgtttc  1020
tttggcagtg tcttagctgg ttgttgtgag caatagtaag gaagcaatca gcaagtatac  1080
tgccctagaa gtgctgcacg ttgtggggcc cgagacactc ctaatggaat gccgttatcc  1140
aaagagcagc acgaacccga cagggctgag tggcttgtgc tagggagagg tttgtgtcat  1200
tcctgctgac caaactgcag gaaaaactgc taattgtcat gctgaagact gcctgacggg  1260
gagactctgc cttctgtaag taggtcatgt aaagagcacg tgctccttgc tgct        1314
```

| SEQ ID NO: 5 | moltype = DNA length = 797 |
| --- | --- |
| FEATURE | Location/Qualifiers |
| source | 1..797 |
| | mol_type = other DNA |
| | organism = synthetic construct |

SEQUENCE: 5

```
cttttcaatt tgaagagagt gcttcctctg ttcttaaggc tagggaacca aattaggttg    60
tttcaatatc gtggacgggcg ctaggatcaa ctcaacatca gtcaatgtga taagctacaa   120
gtattctggt cacagaatac aactcaacat cagtcaatgt gataagctac aagatgatcc   180
tagcgccgtc ttgtcggcag tgggaagggg ggccgataca ctgtacgaga gtgagtagca   240
ggtctcacag tgaaccggtc tctttcccta ctgccgacag ctgcctcggg aagccaagtt   300
gggctttaaa gtgcagggcc tgctgatgtt gagtgctttt tgttggcctc tctctccgtg   360
ttcacagcgg accttgattt aaatgtccat acaattaagg cacgcggtga atgccaagaa   420
tggggctggc ataagaagtt atgtattcat ccaataattc aagccaagca agtatatagg   480
tgttttaata gttttgtttt gcactgactc tcttcggtga cggtattct tgggtggata   540
atacggatta cgttgttatt gcttaagaat acgcgtagtc gaggagagta ccagtgcaca   600
ctcctaatgg aatgccgtta tccaaagagc agcacgaacc cgacagggct gagtggcttg   660
tgctagggag aggtttgtgt cattcctgct gaccaaactg caggaaaaac tgctaattgt   720
catgctgaag actgcctgac ggggagactc tgccttctgt aagtaggtca tgtaaagagc   780
acgtgctcct tgctgct                                                  797
```

| SEQ ID NO: 6 | moltype = DNA length = 811 |
| --- | --- |
| FEATURE | Location/Qualifiers |

```
source                    1..811
                          mol_type = other DNA
                          organism = synthetic construct
SEQUENCE: 6
cttttcaatt tgaagagagt gcttcctctg ttcttaaggc tagggaacca aattaggttg     60
tttcaatatc gtggacggcg ctaggatcaa ctcaacatca gtcaatgtga taagctacaa    120
gtattctggt cacagaatac aactcaacat cagtcaatgt gataagctac aagatgatcc    180
tagcgccgtc tttcttatgt ctcgggatat cccagggggg ccgatacact gtacgagagt    240
gagtagcagg tctcacagtg aaccggtctc tttctgggat atcctcgaga cataagaaac    300
aagatagatc ctgaaactgt tttaaggttg gccgatcttc tgctcgagaa tgcatgaagc    360
gttccatatt ttttccgtgt tcacagcgga ccttgattta aatgtccata caattaaggc    420
acgcggtgaa tgccaagaat aatatggaac gcttatgtat tcatccaata attcaagcca    480
agcaagtata taggtgtttt aatagttttt gtttgcactg actctcttcg gtgacgggta    540
ttcttgggtg gataatacgg attacgttgt tattgcttaa gaatacgcgt agtcgaggag    600
agtaccagtg cacactccta atggaatgcc gttatccaaa gagcagcacg aacccgacag    660
ggctgagtgc cttgtgctag ggagaggttt gtgtcattcc tgctgaccaa actgcaggaa    720
aaactgctaa ttgtcatgct gaagactgcc tgacggggag actctgcctt ctgtaagtag    780
gtcatgtaaa gagcacgtgc tccttgctgc t                                   811

SEQ ID NO: 7              moltype = DNA  length = 76
FEATURE                   Location/Qualifiers
source                    1..76
                          mol_type = other DNA
                          organism = synthetic construct
SEQUENCE: 7
cagtgggaag gggggccgat acactgtacg agagtgagta gcaggtctca cagtgaaccg     60
gtctctttcc ctactg                                                     76

SEQ ID NO: 8              moltype = DNA  length = 83
FEATURE                   Location/Qualifiers
source                    1..83
                          mol_type = other DNA
                          organism = synthetic construct
SEQUENCE: 8
ggcctctctc tccgtgttca cagcggacct tgatttaaat gtccatacaa ttaaggcacg     60
cggtgaatgc caagaatggg gct                                             83

SEQ ID NO: 9              moltype = DNA  length = 91
FEATURE                   Location/Qualifiers
source                    1..91
                          mol_type = other DNA
                          organism = synthetic construct
SEQUENCE: 9
ctgactctct tcggtgacgg gtattcttgg gtggataata cggattacgt tgttattgct     60
taagaatacg cgtagtcgag gagagtacca g                                    91

SEQ ID NO: 10             moltype = DNA  length = 98
FEATURE                   Location/Qualifiers
source                    1..98
                          mol_type = other DNA
                          organism = synthetic construct
SEQUENCE: 10
gtggaccggc tggccccatc tggaagacta gtgattttgt tgttgtctta ctgcgctcaa     60
caacaaatcc cagtctacct aatggtgcca gccatcgc                             98

SEQ ID NO: 11             moltype = DNA  length = 109
FEATURE                   Location/Qualifiers
source                    1..109
                          mol_type = other DNA
                          organism = synthetic construct
SEQUENCE: 11
gtgataatgt agcgagattt tctgttgtgc ttgatctaac catgtggttg cgaggtatga     60
gtaaaacatg gttccgtcaa gcaccatgga acgtcacgca gctttctac                109

SEQ ID NO: 12             moltype = DNA  length = 109
FEATURE                   Location/Qualifiers
source                    1..109
                          mol_type = other DNA
                          organism = synthetic construct
SEQUENCE: 12
ggccagcgtg agtgtttctt tggcagtgtc ttagctggtt ttgtgagca atagtaagga     60
agcaatcagc aagtatactg ccctagaagt gctgcacgtt gtggggccc                109

SEQ ID NO: 13             moltype = DNA  length = 194
FEATURE                   Location/Qualifiers
source                    1..194
                          mol_type = other DNA
                          organism = synthetic construct
SEQUENCE: 13
```

```
cttttcaatt tgaagagagt gcttcctctg ttcttaaggg gctagggaac caaattaggt    60
tgtttcaata tcgtgctaaa agatactgcc tttagaagaa ggctattgac aatccagcgt   120
gtctcggtgg aactctgact ccatggttca ctttcatgat ggccacatgc ctcctgccca   180
gagcccggca gcca                                                    194

SEQ ID NO: 14         moltype = DNA   length = 192
FEATURE               Location/Qualifiers
source                1..192
                      mol_type = other DNA
                      organism = synthetic construct
SEQUENCE: 14
cttttcaatt tgaagagagt gcttcctctg ttcttaaggc tagggaacca aattaggttg    60
tttcaatatc gtggacggcg ctaggatcaa ctcaacatca gtcaatgtga taagctacaa   120
gtattctggt cacagaatac aactcaacat cagtcaatgt gataagctac aagatgatcc   180
tagcgccgtc tt                                                      192

SEQ ID NO: 15         moltype = DNA   length = 200
FEATURE               Location/Qualifiers
source                1..200
                      mol_type = other DNA
                      organism = synthetic construct
SEQUENCE: 15
acactcctaa tggaatgccg ttatccaaag agcagcacga acccgacagg gctgagtggc    60
ttgtgctagg gagaggtttg tgtcattcct gctgaccaaa ctgcaggaaa aactgctaat   120
tgtcatgctg aagactgcct gacggggaga ctctgccttc gtaagtaggt catgtaaag   180
agcacgtgct ccttgctgct                                              200

SEQ ID NO: 16         moltype = DNA   length = 62
FEATURE               Location/Qualifiers
source                1..62
                      mol_type = other DNA
                      organism = synthetic construct
SEQUENCE: 16
agctgcctcg ggaagccaag ttgggcttta aagtgcaggg cctgctgatg ttgagtgctt    60
tt                                                                  62

SEQ ID NO: 17         moltype = DNA   length = 69
FEATURE               Location/Qualifiers
source                1..69
                      mol_type = other DNA
                      organism = synthetic construct
SEQUENCE: 17
taagaagtta tgtattcatc caataattca agccaagcaa gtatataggt gttttaatag    60
tttttgttt                                                           69

SEQ ID NO: 18         moltype = DNA   length = 92
FEATURE               Location/Qualifiers
source                1..92
                      mol_type = other DNA
                      organism = synthetic construct
SEQUENCE: 18
tatttccttc aaatgaatga ttttttactaa ttttgtgtac ttttattgtg tcgatgtaga    60
atctgcctgg tctatctgat gtgacagctt ct                                 92

SEQ ID NO: 19         moltype = DNA   length = 56
FEATURE               Location/Qualifiers
source                1..56
                      mol_type = other DNA
                      organism = synthetic construct
SEQUENCE: 19
tagctgtaga actccagctt cggcctgtcg cccaatcaaa ctgtcctgtt actgaa        56

SEQ ID NO: 20         moltype = DNA   length = 37
FEATURE               Location/Qualifiers
source                1..37
                      mol_type = other DNA
                      organism = synthetic construct
SEQUENCE: 20
aaaagtctgt agaaaagtaa gggaaactca aacccct                             37

SEQ ID NO: 21         moltype = DNA   length = 98
FEATURE               Location/Qualifiers
source                1..98
                      mol_type = other DNA
                      organism = synthetic construct
SEQUENCE: 21
gggatatcct cgagacataa gaaacaagat agatcctgaa actgttttaa ggttggccga    60
tcttctgctc gagaatgcat gaagcgttcc atattttt                           98
```

COMPOSITIONS AND THERAPEUTIC METHODS OF microRNA GENE DELIVERY

CROSS-REFERENCE TO RELATED APPLICATIONS

The application claims priority to, and the benefit of U.S. Provisional Patent Application No. 62/664,362, filed Apr. 30, 2018, the disclosure of which is incorporated by reference in its entirety.

SEQUENCE LISTING

The instant application contains a Sequence Listing which has been submitted electronically in XML format and is hereby incorporated by reference in its entirety. Said XML copy, created Dec. 5, 2023, is named 51377-002003 Sequence Listing 12_5_23 and is 26,066 bytes in size.

FIELD OF THE INVENTION

The invention relates to artificial microRNA clusters and methods of using the same.

BACKGROUND

MicroRNAs are small non-coding RNAs that are important for regulation of gene expression in plants, animals, and viruses. The biological action of microRNAs is exerted by its interaction with a target messenger RNA (mRNA) molecule. Binding of a microRNA to an mRNA leads to destabilization, cleavage, and/or less efficient translation of the mRNA molecule. Given the important role of microRNAs In normal cell function, alterations in the microRNA expression have been associated with a variety of human diseases including diseases of the heart, kidney, nervous system, and cancer. Cancers and many other diseases have boon associated with reduced expression of multiple microRNAs, and a corresponding increase in multiple epigenetic regulator proteins under their control. Current treatment modalities simultaneously targeting multi-protein signaling pathways are lacking, thus underscoring the need for new therapeutic avenues.

SUMMARY OF THE INVENTION

The present invention provides methods and compositions for artificial microRNAs and microRNA clusters for the treatment of a disease (e.g., cancer, such as glioblastoma multiforme (GBM), leukemia, breast cancer, or thyroid cancer, among others) in a subject (e.g. a human subject). The compositions described herein provide therapeutic artificial microRNA and microRNA cluster constructs based on the genetic scaffolds of naturally occurring microRNAs and microRNA clusters. The disclosure also provides expression vectors for therapeutic delivery of compositions described herein as well as methods for preparing the artificial microRNAs and microRNA clusters.

In one aspect, the invention provides a composition including a non-naturally occurring (e.g. artificial) microRNA, wherein the microRNA includes a 5' flanking sequence, a single microRNA hairpin domain, and a 3' flanking sequence, wherein the microRNA hairpin domain is heterologous with respect to the non-naturally occurring microRNA, wherein the 5' and/or 3' flanking sequences include a non-coding RNA sequence, wherein the non-coding RNA sequence includes a biologically active sequence, wherein the 5' flanking sequence is contiguous with a 5' end of the microRNA hairpin domain, wherein the 3' flanking sequence is contiguous with a 3' end of the microRNA hairpin domain. In some embodiments, the 5' flanking sequence is not contiguous with a 5' end of the microRNA hairpin domain. In some embodiments, the 3' flanking sequence is not contiguous with a 3' end of the microRNA hairpin domain. In some embodiments, the non-naturally occurring microRNA includes a pair of acceptor sites (e.g., base of stem sequences) attached to the microRNA hairpin domain. In some embodiments, the pair of acceptor sites includes a 5' acceptor site and a 3' acceptor site. In some embodiments, the 5' acceptor site is attached at its 3' end to the 5' end of the microRNA hairpin domain. In some embodiments, the 3' acceptor site is attached at its 5' end to the 3' end of the microRNA hairpin domain. In some embodiments, the pair of acceptor sites is homologous to the non-naturally occurring microRNA. In some embodiments, the pair of acceptor sites is homologous to the 5' flanking sequence. In some embodiments, the pair of acceptor sites is homologous to the microRNA hairpin domain. In some embodiments, the pair of acceptor sites is homologous to the 3' flanking sequence. In some embodiments, the pair of acceptor sites is heterologous to the non-naturally occurring microRNA. In some embodiments, the pair of acceptor sites is heterologous to the 5' flanking sequence. In some embodiments, the pair of acceptor sites is heterologous to the microRNA hairpin domain. In some embodiments, the pair of acceptor sites is heterologous to the 3' flanking sequence. In some embodiments, the acceptor sites are short nucleotide sequences (e.g., 3-21 nucleotides). In some embodiments, the 5' acceptor site is attached at its 5' end to a 5' flanking sequence. In some embodiments, the 5' acceptor site is attached at its 5' end to a spacer sequence. In some embodiments, the 3' acceptor site is attached at its 3' end to a 3' flanking sequence. In some embodiments, the 3' acceptor site is attached at its 3' end to a spacer sequence. In some embodiments, the pair of acceptor sites is based on non-coding RNA sequences within the artificial microRNA. In some embodiments, the microRNA hairpin domain is heterologous with respect to the 5' flanking sequence. In some embodiments, the microRNA hairpin domain is heterologous with respect to the 3' flanking sequence. In some embodiments, the microRNA hairpin domain is heterologous with respect to the 5' and 3' flanking sequences. In some embodiments, the microRNA hairpin domain includes any one of miR-128, miR-124, miR-137, miR-7, miR-218, and miR-34 hairpin domains. In some embodiments, the microRNA hairpin domain includes a hairpin domain of any microRNA known to have reduced expression in a human disease (e.g., cancer, such as glioblastoma multiforme (GBM), leukemia, breast cancer, or thyroid cancer, among others). In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes an aptamer. In some embodiments, the non-coding RNA sequence encodes a microRNA sponge sequence. In some embodiments, the microRNA sponge sequence is antisense or partially antisense to a target microRNA sequence. In some embodiments, the target microRNA sequence is a miR-21 nucleotide sequence.

In another aspect, the invention provides a composition including a non-naturally occurring microRNA cluster composition, wherein the microRNA cluster includes a 5' flanking sequence, two or more (e.g., 2, 3, 4, 5, 6, or more) microRNA hairpin domains, wherein the two or more hairpin domains are separated by one or more (e.g., 1, 2, 3, 4, 5, or more) spacer sequences, and a 3' flanking sequence. In some embodiments, the 5' flanking sequence is contiguous with a 5' end of a microRNA hairpin domain. In some embodiments, the 3' flanking sequence is contiguous with a 3' end of a microRNA hairpin domain. In some embodiments, the 5' flanking sequence is not contiguous with a 5' end of a microRNA hairpin domain. In some embodiments, the 3' flanking sequence is not contiguous with a 3' end of a microRNA hairpin domain. In some embodiments, the non-naturally occurring microRNA cluster includes two or more pairs of acceptor sites attached to the two or more microRNA hairpin domains. In some embodiments, the two or more pairs of acceptor sites include a 5' acceptor site and a 3' acceptor site. In some embodiments, the 5' acceptor site is attached at its 3' end to the 5' end of a microRNA hairpin domain. In some embodiments, the 3' acceptor site is attached at its 5' end to the 3' end of a microRNA hairpin domain. In some embodiments, the two or more pairs of acceptor sites are homologous to the non-naturally occurring microRNA cluster. In some embodiments, the two or more pairs of acceptor sites are homologous to the 5' flanking sequence. In some embodiments, the two or more pairs of acceptor sites are homologous to one or more microRNA hairpin domains. In some embodiments, the two or more pairs of acceptor sites are homologous to the 3' flanking sequence. In some embodiments, the two or more pairs of acceptor sites are heterologous to the non-naturally occurring microRNA cluster. In some embodiments, the two or more pairs of acceptor sites are heterologous to the 5' flanking sequence. In some embodiments, the two or more pairs of acceptor sites are heterologous to one or more microRNA hairpin domains. In some embodiments, the two or more pairs of acceptor sites are heterologous to the 3' flanking sequence. In some embodiments, the acceptor sites are short nucleotide sequences (e.g., 3-21 nucleotides). In some embodiments, the 5' acceptor site is attached at its 5' end to a 5' flanking sequence. In some embodiments, the 5' acceptor site is attached at its 5' end to a spacer sequence. In some embodiments, the 3' acceptor site is attached at its 3' end to a 3' flanking sequence. In some embodiments, the 3' acceptor site is attached at its 3' end to a spacer sequence. In some embodiments, the two or more pairs of acceptor sites are based on non-coding RNA sequences within the artificial microRNA cluster. In some embodiments of any of the foregoing aspects, the hairpin domain of the microRNA or the two or more hairpin domains of the microRNA cluster include a stem domain and a loop domain, wherein the stem domain includes a biologically active sequence. In some embodiments of any of the foregoing aspects, the biologically active sequence is antisense or partially antisense to a target sequence. In some embodiments, the two or more hairpin domains of the microRNA cluster are heterologous to the microRNA cluster. In some embodiments, the two or more hairpin domains of the microRNA cluster are heterologous to the 5' flanking sequence. In some embodiments, the two or more hairpin domains of the microRNA cluster are heterologous to the 3' flanking sequence. In some embodiments, the two or more hairpin domains of the microRNA cluster are heterologous to the 5' and 3' flanking sequences. In some embodiments, the two or more hairpin domains of the microRNA cluster are heterologous to the one or more spacer sequences. In some embodiments, the microRNA cluster includes the nucleic acid sequence of any one of SEQ ID NOs. 1-6, or a variant thereof having at least 70% (e.g., at least 70%, 75%, 80% k, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6.

In some embodiments, the microRNA cluster includes two or more (e.g., 2, 3, 4, 5, 6, or more) microRNA hairpin domains. In some embodiments, the microRNA cluster includes one microRNA hairpin domain. In some embodiments, the microRNA cluster includes two microRNA hairpin domains. In some embodiments, the microRNA cluster includes three microRNA hairpin domains. In some embodiments, the microRNA cluster includes four microRNA hairpin domains. In some embodiments, the microRNA cluster includes five microRNA hairpin domains. In some embodiments, the microRNA cluster includes six microRNA hairpin domains. In some embodiments, the microRNA cluster includes two or more (e.g. 2, 3, 4, 5, 6, or more) microRNA hairpin domains. In some embodiments, the two hairpin domains include miR-128 and miR-124 hairpin domains. In some embodiments, the two hairpin domains include any one of miR-128, miR-124, miR-137, miR-7, miR-218, and miR-34 hairpin domains. In some embodiments, the microRNA cluster includes three or more (e.g. 3, 4, 5, 6, or more) microRNA hairpin domains. In some embodiments, the three hairpin domains include miR-128, miR-124, and miR-137 hairpin domains. In some embodiments, the three hairpin domains include any one of miR-128, miR-124, miR-137, miR-7, miR-218, and miR-34 hairpin domains. In some embodiments, the microRNA cluster includes four or more (e.g. 4, 5, 6, or more) microRNA hairpin domains. In some embodiments, the four hairpin domains include miR-128, miR-124, miR-137, and miR-7 hairpin domains. In some embodiments, the four hairpin domains include any one of miR-128, miR-124, miR-137, miR-7, miR-218, and miR-34 hairpin domains. In some embodiments, the microRNA cluster includes five or more (e.g. 5, 6, or more) microRNA hairpin domains. In some embodiments, the five hairpin domains include miR-128, miR-124, miR-137, miR-7, and miR-218 hairpin domains. In some embodiments, the five hairpin domains include any one of miR-128, miR-124, miR-137, miR-7, miR-218, and miR-34 hairpin domains. In some embodiments, the microRNA cluster includes six or more (e.g., 6 or more) microRNA hairpin domains. In some embodiments, the six hairpin domains include miR-128, miR-124, miR-137, miR-7, miR-218, and miR-34 hairpin domains. In some embodiments, the six hairpin domains include any one of miR-128, miR-124, miR-137, miR-7, miR-218, and miR-34 hairpin domains. In some embodiments, the microRNA cluster includes any one of miR-128, miR-124, miR-137, miR-7, miR-218, and miR-34 hairpin domains. In some embodiments, the hairpin one or more hairpin domains include the nucleic acid sequence of any one of SEQ ID NOs. 7-12, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12. In some embodiments, the one or more (e.g., 1, 2, 3, 4, 5, or more) spacer sequences separating the two or more (e.g., 2, 3, 4, 5, 6, or more) hairpin domains are spacer sequences homologous to a miR-17-92 cluster, a miR-367-302 cluster, a miR-181a-b cluster, a miR-24-23-27 cluster, or a miR-143-145 cluster. In some embodiments, the one or more spacer sequences separating the two or more hairpin domains are spacer sequences heterologous to a miR-17-92 cluster, a miR-367-302 cluster, a miR-181a-b cluster, a miR-24-23-27 cluster, or a miR-143-145 cluster. In some embodiments, the one or more spacer sequences include a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes an aptamer. In some embodiments, the aptamer binds to a p50 protein. In some embodiments, the one or more spacer sequences include the nucleic acid sequence of any one of SEQ ID NOs. 16-21, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21.

In some embodiments of any of the foregoing aspects, the 5' flanking sequence and/or the 3' flanking sequence includes a non-coding RNA sequence. In some embodiments of any of the foregoing aspects, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments of any of the foregoing aspects, the non-coding RNA sequence encodes a microRNA sponge sequence. In some embodiments of any of the foregoing aspects, the microRNA sponge sequence is antisense or partially antisense to a target microRNA sequence. In some embodiments of any of the foregoing aspects, the target microRNA sequence is a miR-21 nucleotide sequence. In some embodiments of any of the foregoing aspects, the non-coding RNA sequence encodes an aptamer. In some embodiments of any of the foregoing aspects, the non-coding RNA sequence is a 5' flanking sequence of miR-128, miR-124, miR-137, miR-7, miR-218, or miR-34. In some embodiments of any of the foregoing aspects, the non-coding RNA sequence is a 3' flanking sequence of miR-128, miR-124, miR-137, miR-7, miR-218 or miR-34. In some embodiments of any of the foregoing aspects, the 5' flanking sequence includes the nucleic acid sequence of SEQ ID NO. 13 or SEQ ID NO. 14, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 13 or SEQ ID NO. 14. In some embodiments of any of the foregoing aspects, the 3' flanking sequence includes the nucleic acid sequence of SEQ ID NO. 15, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15.

In some embodiments, the microRNA cluster includes in a 5' to 3' direction, a miR-128 5' flanking sequence, a miR-128 hairpin domain, a first miR-17-92 spacer sequence, a miR-124 hairpin domain, and a miR-128 3' flanking sequence.

In some embodiments, the microRNA cluster includes in a 5' to 3' direction, a miR-128 5' flanking sequence, a miR-128 hairpin domain, a first miR-17-92 spacer sequence, a miR-124 hairpin domain, a second miR-17-92 spacer sequence, a miR-137 hairpin domain, and a miR-128 3' flanking sequence In some embodiments, the microRNA cluster includes in a 5' to 3' direction, a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, and a miR-128 3' flanking sequence.

In some embodiments, the microRNA cluster includes in a 5' to 3' direction, a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 domain, and a miR-128 3' flanking sequence.

In some embodiments, the microRNA cluster includes in a 5' to 3' direction, a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 domain, a fifth miR-17-92 spacer sequence, a miR-34 hairpin domain, and a miR-128 3' flanking sequence.

In some embodiments of any of the foregoing aspects, at least one (e.g., at least 1, 2, 3, 4, 5, 6, or more) hairpin domain is heterologous with respect to the 5' flanking sequence. In some embodiments of any of the foregoing aspects, at least one hairpin domain is heterologous with respect to the 3' flanking sequence. In some embodiments of any of the foregoing aspects, at least one hairpin domain is heterologous with respect to the one or more spacer sequences. In some embodiments of any of the foregoing aspects, at least one hairpin domain is heterologous with respect to at least one pair of acceptor sites.

In some embodiments of any of the foregoing aspects, the non-naturally occurring microRNA and/or artificial microRNA cluster include sequences necessary for natural processing of the microRNAs and/or microRNA clusters within a cell (e.g., a cell of a human subject).

In some embodiments of any of the foregoing aspects, an expression vector is provided that includes any of the foregoing compositions. In some embodiments of any of the foregoing aspects, the vector is a plasmid or a virus. In some embodiments of any of the foregoing aspects, the virus is a lentivirus, an adeno-associated virus (AAV), or a replicating retrovirus. In some embodiments of any of the foregoing aspects, the AAV is AAV2 or AAV9. In some embodiments of any of the foregoing aspects, the vector further includes a promoter operably linked to the composition of any of the above aspects and embodiments. In some embodiments of any of the foregoing aspects, the promoter is endogenous to a eukaryotic cell. In some embodiments of any of the foregoing aspects, the promoter is selected from the list including the cytomegalovirus (CMV) promoter, the elongation factor 1 (EF1) promoter, and the bacteriophage T7 (T7) promoter. In some embodiments of any of the foregoing aspects, the invention provides an AAV expression vector including a polynucleotide encoding a non-naturally-occurring microRNA cluster, the cluster including a 5' flanking sequence, two or more microRNA hairpin domains, wherein the two or more hairpin domains are separated by one or more spacer sequences, a 3' flanking sequence, wherein the microRNA hairpin domain is heterologous with respect to the microRNA cluster, wherein the 5' flanking sequence, the 3' flanking sequence, and/or one or more spacer sequences include a non-coding RNA sequence, wherein the microRNA hairpin domain and/or non-coding RNA sequence include a biologically active sequence.

In some embodiments of any of the foregoing aspects, the invention provides a replicating retroviral expression vector including a polynucleotide encoding a non-naturally-occurring microRNA cluster, the cluster including a 5' flanking sequence, two or more microRNA hairpin domains, wherein the two or more hairpin domains are separated by one or more spacer sequences, a 3' flanking sequence, wherein the microRNA hairpin domain is heterologous with respect to the microRNA cluster, wherein the 5' flanking sequence, the 3' flanking sequence, and/or one or more spacer sequences include a non-coding RNA sequence, wherein the microRNA hairpin domain and/or non-coding RNA sequence include a biologically active sequence.

In some embodiments, the invention provides a lentiviral expression vector including a polynucleotide encoding a non-naturally-occurring microRNA cluster, the cluster including a 5' flanking sequence, two or more microRNA hairpin domains, wherein the two or more hairpin domains are separated by one or more spacer sequences, a 3' flanking sequence, wherein the microRNA hairpin domain is heterologous with respect to the microRNA cluster, wherein the 5' flanking sequence, the 3' flanking sequence, and/or one or more spacer sequences include a non-coding RNA sequence, wherein the microRNA hairpin domain and/or non-coding RNA sequence include a biologically active sequence.

In some embodiments of any of the foregoing aspects, a method is provided for treating a disease (e.g., cancer, such as GBM, leukemia, breast cancer, or thyroid cancer, among others) in a subject in need of treatment, the method including administering to the subject the expression vector of the foregoing embodiments, wherein the expression vector includes the composition of any of the foregoing aspects and embodiments, wherein the composition is capable of entering target cells (e.g. cancer cells) of the subject in an amount effective to produce a therapeutic effect. In some embodiments of any of the foregoing aspects, the subject is a human subject. In some embodiments of any of the foregoing aspects, the expression vector is administered to the subject as part of a targeted delivery system. In some embodiments of any of the foregoing aspects, the targeted delivery system is selected from a group including liposomes, exosomes, virosomes, and nanoparticles. In some embodiments of any of the foregoing aspects, the expression vector is administered to autologous cells of the subject ex vivo, and the cells are then administered to the subject in vivo. In some embodiments of any of the foregoing aspects, the cells are administered to the subject intratumorally. In some embodiments of any of the foregoing aspects, the cells are administered to the subject by way of intravenous injection, intraperitoneal injection, oral Ingestion, or Inhalation (e.g., by way of a nebulizer). In some embodiments of any of the foregoing aspects, the cells are administered by way of intracerebroventricular injection or intraparenchymal injection. In some embodiments of any of the foregoing aspects, the autologous cells are multipotent cells. In some embodiments of any of the foregoing aspects, the multipotent cells are mesenchymal stem cells. In some embodiments of any of the foregoing aspects, the autologous cells are cancer cells. In some embodiments of any of the foregoing aspects, the cancer cells are glioblastoma GBM cancer cells. In some embodiments of any of the foregoing aspects, the cancer cells are leukemia cancer cells. In some embodiments of any of the foregoing aspects, the cancer cells are breast cancer cells. In some embodiments of any of the foregoing aspects, the cancer cells are thyroid cancer cells.

In some embodiments of any of the foregoing aspects, the expression vector is administered to the subject by way of intravenous injection, intraperitoneal injection, oral ingestion, or inhalation (e.g. by way of a nebulizer). In some embodiments of any of the foregoing aspects, the expression vector is administered by way of intrathecal injection, intracerebroventricular injection, intraparenchymal injection, or intratumoral injection. In some embodiments of any of the foregoing aspects, the expression vector is administered by way of intratumoral injection.

In some embodiments of any of the foregoing aspects, upon administration of the expression vector to the subject, the vector expresses the composition of any one of the foregoing aspects and embodiments in one or more target cells in the subject, wherein the one or more target cells then secrete microRNAs expressed individually or in a microRNA cluster and any associated heterologous non-coding RNA sequences within extracellular vesicles, wherein the extracellular vesicles containing the microRNAs are then internalized by neighboring cells.

In some embodiments of any of the foregoing aspects, the expression vector is administered to the subject in combination with a second therapeutic agent or a second therapeutic modality. In some embodiments of any of the foregoing aspects, the second therapeutic agent is a chemotherapeutic drug. In some embodiments, the chemotherapeutic drug is temozolomide. In some embodiments of any of the foregoing aspects, the second therapeutic agent is an immunomodulatory agent. In some embodiments of any of the foregoing aspects, the second therapeutic modality is radiation therapy. In some embodiments of any of the foregoing aspects, the disease is cancer. In some embodiments of any of the foregoing aspects, the cancer is GBM. In some embodiments of any of the foregoing aspects, the cancer is leukemia. In some embodiments of any of the foregoing aspects, the cancer is breast cancer. In some embodiments of any of the foregoing aspects, the cancer is thyroid cancer. In some embodiments of any of the foregoing aspects, the therapeutic effect results from regulation of chromatin and/or cellular signaling pathways associated with epigenetic regulation.

In another aspect, the invention provides a method for preparing a non-naturally occurring microRNA, wherein the method includes providing a microRNA scaffold, wherein the scaffold includes in a 5' to 3' direction, a 5' flanking sequence, a pair of acceptor sites for attaching a single microRNA hairpin domain, wherein the pair of acceptor sites includes a 5' and a 3' acceptor site, wherein the scaffold further includes a 3' flanking sequence, the method further including attaching a microRNA hairpin domain to the pair of acceptor sites.

In another aspect, the invention provides a method for preparing a non-naturally occurring microRNA cluster, wherein the method includes providing a microRNA cluster scaffold, wherein the scaffold includes in a 5' to 3' direction, a 5' flanking sequence, two or more pairs of acceptor sites for attaching two or more microRNA hairpin domains, wherein each pair of acceptor sites includes a 5' and a 3' acceptor site, wherein the scaffold further includes one or more spacer sequences separating the two or more of the hairpin domains, and a 3' flanking sequence, the method further including attaching the two or more microRNA hairpin domains to the two or more pairs of acceptor sites. In some embodiments of the two foregoing aspects, the pair or pairs of acceptor sites are short nucleotide sequences (e.g., 3-21 nucleotides long) that are based on or derived from the hairpin domains of the naturally occurring microRNA cluster-based scaffold. In some embodiments of the two foregoing aspects, the pairs of acceptor sites include synthetic sequences. In some embodiments of the two foregoing aspects, the pairs of acceptor sites are heterologous to the artificial microRNA or microRNA cluster. In some embodiments, the pairs of acceptor sites are based on non-coding RNA sequences within the artificial microRNA cluster. In some embodiments, the pairs of acceptor sites include a 5' and a 3' acceptor site. In some embodiments, the method of the two forgoing aspects is performed in silico. In some embodiments, the microRNA cluster scaffold is derived from a miR-17-92 cluster. In some embodiments, the microRNA cluster scaffold is derived from a microRNA cluster selected from the group consisting of a miR-367-302 cluster, a miR-181a-b cluster, a miR-24-23-27 cluster, or a miR-143-145 cluster. In some embodiments of the two foregoing aspects, the single hairpin domain of the microRNA or the two or more hairpin domains of the microRNA cluster are heterologous to the microRNA scaffold or the microRNA cluster scaffold. In some embodiments of the two foregoing aspects, the single heterologous microRNA hairpin domain or the two or more heterologous microRNA hairpin domains are selected from a group including a miR-128 hairpin domain, miR-124 hairpin domain, miR-137 hairpin domain, miR-7 hairpin domain, miR-218 hairpin domain, and a miR-34 miR hairpin domain. In some embodiments of the two foregoing aspects, the 5' flanking sequence or the 3' flanking sequence is heterologous to the microRNA scaffold, the microRNA cluster scaffold, the single hairpin domain, or two or more hairpin domains. In some embodiments of the two foregoing aspects, the 5' flanking sequence and the 3' flanking sequence are heterologous to the microRNA scaffold, the microRNA cluster scaffold, the single hairpin domain, or two or more hairpin domains. In some embodiments of the two foregoing aspects, the 5' flanking sequence or the 3' flanking sequence includes a non-coding RNA sequence. In some embodiments of the two foregoing aspects, the 5' flanking sequence and the 3' flanking sequence include a non-coding RNA sequence. In some embodiments of the two foregoing aspects, the noncoding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments of the two foregoing aspects, the non-coding RNA sequence encodes a microRNA sponge sequence. In some embodiments of the two foregoing aspects, the microRNA sponge sequence is antisense or partially antisense to a target microRNA sequence. In some embodiments of the two foregoing aspects, the target microRNA sequence is a miR-21 nucleotide sequence. In some embodiments of the two foregoing aspects, the non-coding RNA sequence encodes an aptamer. In some embodiments of the two foregoing aspects, the non-coding RNA sequence includes a miR-128 5' or 3' flanking sequence, miR-124 5' or 3' flanking sequence, miR-137 5' or 3' flanking sequence, miR-7 5' or 3' flanking sequence, a miR-218 5' or 3' flanking sequence, or a miR-34 5' or 3' flanking sequence. In some embodiments, the one or more spacer sequences are heterologous to the microRNA scaffold, microRNA cluster scaffold, the single hairpin domain, or the two or more hairpin domains. In some embodiments, the spacer sequence includes a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes an aptamer. In some embodiments, the aptamer binds to a p50 protein.

Some embodiments of the invention described herein can be defined according to any of the following numbered paragraphs:

1. A composition including a non-naturally occurring microRNA, the microRNA including
   i. a 5' flanking sequence
   ii. a single microRNA hairpin domain; and
   iii. a 3' flanking sequence;
   wherein the microRNA hairpin domain is heterologous with respect to the non-naturally occurring microRNA, wherein the 5' and/or 3' flanking sequences include a non-coding RNA sequence, wherein the non-coding RNA sequence includes a biologically active sequence, wherein the 5' flanking sequence is contiguous with a 5' end of the microRNA hairpin domain, wherein the 3' flanking sequence is contiguous with a 3' end of the microRNA hairpin domain.
2. The composition of paragraph 1, wherein the microRNA hairpin domain includes any one of miR-128, miR-124, miR-137, miR-7, miR-218, and miR-34 hairpin domains.
3. A composition including a non-naturally occurring microRNA cluster composition, the cluster including:
   i. a 5' flanking sequence;
   ii. two or more microRNA hairpin domains, wherein the two or more hairpin domains are separated by one or more spacer sequences; and
   iii. a 3' flanking sequence.
4. The composition of any one of paragraphs 1-3, wherein the hairpin domain of the microRNA or the two or more hairpin domains of the microRNA cluster include a stem domain and a loop domain, wherein the stem domain includes a biologically active sequence.
5. The composition of paragraph 4, wherein the biologically active sequence is antisense or partially antisense to a target sequence.
6. The composition of any one of paragraphs 3-5, wherein the two or more hairpin domains of the microRNA cluster are heterologous to the microRNA cluster.
7. The composition of any one of paragraphs 3-6, wherein the two hairpin domains include miR-128 and miR-124 hairpin domains.
8. The composition of any one of paragraphs 3-7, wherein the microRNA cluster includes three or more hairpin domains.
9. The composition of paragraph 8, wherein the three hairpin domains include miR-128, miR-124, and miR-137 hairpin domains.
10. The composition of any one of paragraphs 3-9, wherein the microRNA cluster includes four or more hairpin domains.
11. The composition of paragraph 10, wherein the four hairpin domains include miR-128, miR-124, miR-137, and miR-7 hairpin domains.
12. The composition of any one of paragraphs 3-11, wherein the microRNA cluster includes five or more hairpin domains.
13. The composition of paragraph 12, wherein the five hairpin domains include miR-128, miR-124, miR-137, miR-7, and miR-218 hairpin domains.
14. The composition of any one of paragraphs 3-13, wherein the microRNA cluster includes six hairpin domains.

15. The composition of paragraph 14, wherein the six hairpin domains include miR-128, miR-124, miR-137, miR-7, miR-218, and miR-34 hairpin domains.
16. The composition of any one of paragraphs 3-15, wherein the one or more spacer sequences separating the two or more hairpin domains are spacer sequences homologous to a miR-17-92 cluster, a miR-367-302 cluster, a miR-181a-b cluster, a miR-24-23-27 cluster, or a miR-143-145 cluster.
17. The composition of any one of paragraphs 3-15, wherein the one or more spacer sequences separating the two or more hairpin domains are spacer sequences heterologous to a miR-17-92 cluster, a miR-367-302 cluster, a miR-181a-b cluster, a miR-24-23-27 cluster, or a miR-143-145 cluster.
18. The composition of any one of paragraphs 3-17, wherein the one or more spacer sequences include a non-coding RNA sequence.
19. The composition of paragraph 18, wherein the non-coding RNA sequence encodes an aptamer.
20. The composition of paragraph 19, wherein the aptamer binds to a p50 protein.
21. The composition of any one paragraphs 1-20, wherein the 5' flanking sequence and/or the 3' flanking sequence includes a non-coding RNA sequence.
22. The composition of paragraph 21, wherein the non-coding RNA sequence encodes a microRNA sponge sequence.
23. The composition of paragraph 22, wherein the microRNA sponge sequence is antisense or partially antisense to a target microRNA sequence.
24. The composition of paragraph 23, wherein the target microRNA sequence is a miR-21 nucleotide sequence.
25. The composition of paragraph 21, wherein the non-coding RNA sequence encodes an aptamer.
26. The composition of paragraph 21, wherein the non-coding RNA sequence is a 5' flanking sequence of miR-128, miR-124, miR-137, miR-7, miR-218, or miR-34.
27. The composition of paragraph 21, wherein the non-coding RNA is a 3' flanking sequence of miR-128, miR-124, miR-137, miR-7, miR-218 or miR-34.
28. The composition of paragraph 3, wherein the microRNA cluster includes in a 5' to 3' direction a miR-128 5' flanking sequence, a miR-128 hairpin domain, a first miR-17-92 spacer sequence, a miR-124 hairpin domain, and a miR-128 3' flanking sequence.
29. The composition of paragraph 3, wherein the microRNA cluster includes a miR-128 5' flanking sequence, a miR-128 hairpin domain, a first miR-17-92 spacer sequence, a miR-124 hairpin domain, a second miR-17-92 spacer sequence, a miR-137 hairpin domain, and a miR-128 3' flanking sequence.
30. The composition of paragraph 3, wherein the microRNA cluster includes a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, and a miR-128 3' flanking sequence.
31. The composition of paragraph 3, wherein the microRNA cluster includes a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 domain, and a miR-128 3' flanking sequence.
32. The composition of paragraph 3, wherein the cluster includes a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 domain, a fifth miR-17-92 spacer sequence, a miR-34 hairpin domain, and a miR-128 3' flanking sequence.
33. The composition of any one of paragraphs 1-32, wherein at least one hairpin domain is heterologous with respect to the 5' flanking sequence.
34. The composition of any one of paragraphs 1-33, wherein at least one hairpin domain is heterologous with respect to the 3' flanking sequence.
35. The composition of any one of paragraphs 3-34, wherein at least one hairpin domain is heterologous with respect to the one or more spacer sequences.
36. An expression vector including the composition of any one of paragraphs 1-35.
37. The vector of paragraph 36, wherein the vector is a plasmid or a virus.
38. The vector of paragraph 37, wherein the virus is a lentivirus, an adeno-associated virus (AAV), or a replicating retrovirus.
39. The vector of paragraph 38, wherein the AAV is AAV2 or AAV9.
40. The vector of any one of paragraphs 36-39, wherein the vector further includes a promoter operably linked to the composition of any one of paragraphs 1-35.
41. The vector of paragraph 40, wherein the promoter is endogenous to a eukaryotic cell.
42. The vector of paragraph 40, wherein the promoter is a promoter selected from the list including the CMV promoter, the EF1 promoter, or the T7 promoter.
43. A method of treating a disease in a subject in need thereof, the method including administering to the subject the expression vector of any one of paragraphs 36-42, wherein the expression vector includes the composition of anyone of paragraphs 1-35, wherein the composition is capable of entering target cells of the subject in an amount effective to produce a therapeutic effect.
44. The method of paragraph 43, wherein the subject is a human subject.
45. The method of paragraph 43 or 44, wherein the expression vector is administered to the subject as part of a targeted delivery system.
46. The method of paragraph 45, wherein the targeted delivery system is selected from a group consisting of liposomes, exosomes, virosomes, and nanoparticles.
47. The method of any one of paragraphs 43-46, wherein the expression vector is administered to autologous cells of the subject ex vivo, and the cells are then administered to the subject in vivo.
48. The method of paragraph 47, wherein the autologous cells are multipotent cells.
49. The method of paragraph 48, wherein the multipotent cells are mesenchymal stem cells.
50. The method of paragraph 47, wherein the autologous cells are cancer cells.
51. The method of anyone of paragraphs 43-50, wherein the expression vector is administered to the subject systemically.

52. The method of paragraph 51, wherein the expression vector is administered to the subject by way of intravenous injection, intraperitoneal injection, oral ingestion, or inhalation.
53. The method of any one of paragraphs 43-50, wherein the expression vector is administered by way of intrathecal injection, intracerebroventricular injection, intraparenchymal injection, or intratumoral injection.
54. The method of anyone of paragraphs 43-53, wherein upon administration of the expression vector to the subject, the vector expresses the composition of any one of paragraphs 1-35 in one or more target cells, wherein the one or more target cells then secrete microRNAs expressed individually or in a microRNA cluster and any associated heterologous non-coding RNA sequences within extracellular vesicles, wherein the extracellular vesicles containing the microRNAs are then internalized by neighboring cells.
55. The method of any one of paragraphs 43-54, wherein the expression vector is administered to the subject in combination with a second therapeutic agent or a second therapeutic modality.
56. The method of paragraph 55, wherein the second therapeutic agent is a chemotherapeutic drug.
57. The method of paragraph 56, wherein the chemotherapeutic drug is temozolomide.
58. The method of paragraph 55, wherein the second therapeutic agent is an immunomodulatory agent.
59. The method of paragraph 55, wherein the second therapeutic modality is radiation therapy.
60. The method of any one of paragraphs 43-59, wherein the disease is cancer.
61. The method of paragraph 60, wherein the cancer is glioblastoma multiforme.
62. The method of paragraph 60, wherein the cancer is leukemia.
63. The method of paragraph 60, wherein the cancer is breast cancer.
64. The method of paragraph 60, wherein the cancer is thyroid cancer.
65. The method of any one of paragraphs 43-64, wherein the therapeutic effect results from regulation of chromatin and/or cellular signaling pathways associated with epigenetic regulation.
66. A method for preparing a non-naturally occurring microRNA, the method including:
   i. providing a microRNA scaffold, wherein the scaffold includes in a 5' to 3' direction a 5' flanking sequence, a pair of acceptor sites for attaching a single microRNA hairpin domain, wherein the pair of acceptor sites includes a 5' and a 3' acceptor site, wherein the scaffold further includes a 3' flanking sequence; and
   ii. attaching a microRNA hairpin domain to the pair of acceptor sites.
67. A method for preparing a non-naturally occurring microRNA cluster, the method including:
   i. providing a microRNA cluster scaffold, wherein the scaffold includes in a 5' to 3' direction a 5' flanking sequence, two or more pairs of acceptor sites for attaching two or more microRNA hairpin domains, wherein each pair of acceptor sites includes a 5' and a 3' acceptor site, wherein the scaffold further includes one or more spacer sequences separating the two or more of the hairpin domains, and a 3' flanking sequence; and
   ii. attaching two or more microRNA hairpin domains to the two or more pairs of acceptor sites.
68. The method of paragraph 66 or 67, wherein the method is performed in silico.
69. The method of paragraph 67 or 68, wherein the microRNA cluster scaffold is derived from a miR-17-92 cluster.
70. The method of paragraph 67 or 68, wherein the microRNA cluster scaffold is derived from a microRNA cluster selected from the group consisting of a miR-367-302 cluster, a miR-181a-b cluster, a miR-24-23-27 cluster, or a miR-143-145 cluster.
71. The method of any one of paragraphs 66-70, wherein the single hairpin domain of the microRNA or the two or more hairpin domains of the microRNA cluster are heterologous to the microRNA scaffold or the microRNA cluster scaffold.
72. The method of paragraph 71, wherein the single or two or more heterologous microRNA hairpin domains are selected from a group including a miR-128 hairpin domain, miR-124 hairpin domain, miR-137 hairpin domain, miR-7 hairpin domain, miR-218 hairpin domain, and a miR-34 miR hairpin domain.
73. The method of anyone of paragraphs 66-72, wherein the 5' flanking sequence or the 3' flanking sequence is heterologous to the microRNA scaffold, the microRNA cluster scaffold, the single hairpin domain, or two or more hairpin domains.
74. The method of any one of paragraphs 66-73, wherein the 5' flanking sequence or the 3' flanking sequence includes a non-coding RNA sequence.
75. The method of paragraph 74, wherein the non-coding RNA sequence encodes a microRNA sponge sequence.
76. The method of paragraph 75, wherein the microRNA sponge sequence is antisense or partially antisense to a target microRNA sequence.
77. The method of paragraph 76, wherein the target microRNA sequence is a miR-21 nucleotide sequence.
78. The method of paragraph 74, wherein the non-coding RNA sequence encodes an aptamer.
79. The method of paragraph 74, wherein non-coding RNA sequence includes a miR-128 5' or 3' flanking sequence, miR-124 5' or 3' flanking sequence, miR-137 5' or 3' flanking sequence, miR-7 5' or 3' flanking sequence, a miR-218 5' or 3' flanking sequence, or a miR-34 5' or 3' flanking sequence.
80. The method any one of paragraphs 67-79, wherein the one or more spacer sequences are heterologous to the microRNA scaffold, microRNA cluster scaffold, the single hairpin domain, or the two or more hairpin domains.
81. The method of any one paragraphs 67-80, wherein the spacer sequence includes a non-coding RNA sequence.
82. The method of paragraph 81, wherein non-coding RNA sequence encodes an aptamer.
83. The method of paragraph 82, wherein the aptamer binds to a p50 protein.

Definitions

By "3' flanking sequence" is meant a non-coding RNA sequence that is a region of the microRNA or microRNA cluster gene or transcript that is adjacent to the 3' end of the gene or transcript. A 3' flanking sequence may be contiguous with microRNA hairpins or may be separated from the microRNA hairpins by additional elements (e.g. nucleotides). A 3' flanking sequence may be heterologous with respect to any nucleic acid sequence contained within the microRNA or microRNA cluster to which it is attached. As such, the 3' flanking sequence may encode non-coding RNAs having a specified biological activity (e.g. microRNA sponge activity or aptamer activity, among others). Alternatively, a 3' flanking sequence of a microRNA or microRNA cluster may be naturally occurring within (e.g. homologous to) the microRNA or microRNA cluster.

By "5' flanking sequence" is meant a non-coding RNA sequence that is a region of the microRNA or microRNA cluster gene or transcript that is adjacent to the 5' end of the gene or transcript. A 5' flanking sequence may be contiguous with microRNA hairpins or may be separated from the microRNA hairpins by additional elements (e.g. nucleotides). A 5' flanking sequence may be heterologous with respect to any nucleic acid sequence contained within the microRNA or microRNA cluster to which it is attached. As such, the 5' flanking sequence may encode non-coding RNAs having a specified biological activity (e.g. microRNA sponge activity or aptamer activity, among others). Alternatively, a 5' flanking sequence of a microRNA or microRNA cluster may be naturally occurring within (e.g. homologous to) the microRNA or microRNA cluster.

By "acceptor site" is meant a short (e.g., typically 3-21 nucleotides) sequence of a microRNA or microRNA cluster that serves as an insertion site for a microRNA hairpin sequence. For a given microRNA hairpin sequence, two acceptor sites may be necessary to attach to the 5' and 3' ends of the microRNA hairpin sequence. In some embodiments, the acceptor sites are provided by a naturally-occurring microRNA or microRNA cluster. In some embodiments, the acceptor sites are provided by the stem domain of a microRNA hairpin. In some embodiments, the acceptor sites are homologous with respect to an artificial microRNA or microRNA cluster. In some embodiments, the acceptor sites are heterologous with respect to an artificial microRNA or microRNA cluster. In some embodiments, the acceptor site may be provided by a non-coding RNA sequence of a microRNA or microRNA cluster described herein. The term "acceptor site" may be used interchangeably with "base of stem" sequence.

By "antisense or partially antisense" is meant the degree of complementarity and, therefore, the strength of hybridization between two nucleic acid molecules oriented in opposite directions. A nucleic acid sequence, such as those described herein, may be used to target and bind to another nucleic acid molecule (e.g., an mRNA or a microRNA), subsequently leading to its cleavage, degradation, destabilization, and/or to less efficient mRNA translation or microRNA binding to its target. A nucleic acid may be "antisense" to its target sequence if it has 100% complementarity in complex with the target. A nucleic acid may be "partially antisense" If it has greater than 0% but less than 100% complementarity to its target sequence. As such, the degree of complementarity between antisense nucleic acids and their targets may determine the magnitude of the biological effect exerted by them, such as cleavage, degradation, and/or destabilization. The degree of complementarity between two nucleic acid sequences in complex may be determined using routine methods in the art.

By "aptamer" is meant a synthetic non-coding nucleic acid sequence that can adopt specific three-dimensional conformations and bind to a specific molecule, such as a protein, so to modulate (e.g. inhibit) its biological activity. Aptamers typically consist of short strands of oligonucleotides. As described herein, aptamer sequences can be introduced into artificial microRNA or microRNA cluster constructs to expand the repertoire of biological activities of the microRNA or microRNA cluster. Any biological activity associated with the function of an aptamer sequence is termed "aptamer activity."

By "artificial" is meant with respect to microRNA compositions described herein means non-naturally occurring. For example, the microRNAs and microRNA clusters described may be considered artificial when they are manipulated to contain heterologous sequences not normally contained within the microRNAs and/or microRNA clusters. The terms "artificial and "non-naturally occurring" may be used interchangeably.

By "autologous" is meant organs, tissues, cells, or proteins taken from one part of the body of a person and transplanted to the same or a different part of the body of the same person.

By "biologically active sequence" is meant a sequence of a nucleic acid (e.g., microRNA or microRNA clusters as well as any associated non-coding RNA sequences described herein) that can, upon binding to a target sequence, elicit a biological effect, such as, for example, cleavage, degradation, destabilization, and/or less efficient translation of a target sequence. Additionally, "biologically active sequence" refers to a sequence of a nucleic acid that, upon binding to a protein, may modulate (e.g., increase or decrease) its levels of expression or activity.

By "derived" with respect to a nucleic acid sequence is meant that the nucleic acid sequence may contain segments or the entirety of another nucleic acid sequence. For example, as used herein, a microRNA genetic scaffold or microRNA cluster genetic scaffold may be derived from a naturally occurring microRNA cluster when it contains segments, such as structural or functional parts (e.g. 5' flanking sequences, spacer sequences, 3' flanking sequences, acceptor sites, among others), of the naturally occurring microRNA or microRNA cluster. A single nucleic acid sequence (e.g., a nucleic acid sequence of an artificial microRNA cluster) may contain, for example, sequences derived from a single nucleic acid molecule or from multiple different nucleic acid molecules.

By "heterologous," with respect to a nucleic acid sequence, is meant a nucleic acid sequence that is not normally contained within a specific DNA or RNA molecule, not normally expressed in a cell (e.g., a mammalian cell), and/or is not normally found occurring in nature. As used herein, a heterologous nucleic acid may be a microRNA or microRNA cluster having regions of its nucleotide sequence replaced with other sequences. For example, a microRNA or microRNA cluster may have a hairpin sequence that is heterologous with respect to the microRNA or microRNA cluster or any associated non-coding RNA sequence if it is not normally expressed in the microRNA or microRNA cluster in a cell or found occurring in nature.

By "homologous," with respect to a nucleic acid sequence, is meant a nucleic acid sequence that is typically contained within a specific DNA or RNA molecule, is typically expressed in a cell (e.g., a mammalian cell), or is typically found occurring in nature.

By "microRNA" is meant a short (e.g., typically ~22 nucleotide) sequence of non-coding RNA that regulates mRNA translation and thus influences target protein abundance. Some microRNAs are transcribed as single genes (e.g., miR-124, miR-128, miR-137, miR-7, miR-218, miR-34, among others), while others are part of clusters (e.g., miR-367-302, miR-181a-b, miR-24-23-27, miR-17-92, and miR-143-145, among others). The structure of a microRNA may include 5' and 3' flanking sequences, hairpin sequences including stem and stem loop sequences, base of stem sequences. The biological action of microRNAs is exerted at the level of translational regulation through binding to regions of the mRNA molecule, typically the 3' untranslated region, and leading to the cleavage, degradation, destabilization, and/or less efficient translation of the mRNA. Binding of the microRNA to its target is generally mediated by a short (e.g., typically 6-8 nucleotide) "seed region" within the hairpin sequence of the microRNA. As described herein, a microRNA may be a non-naturally occurring microRNA, such as a microRNA having one or more heterologous nucleic acid sequences.

By "microRNA cluster" is meant a polycistronic sequence encoding multiple microRNAs within a single construct. The structure of the microRNA cluster contains all of the individual elements of each microRNA as well as spacer sequences separating any two microRNA hairpin sequences within the cluster. As described herein, a microRNA cluster may be a non-naturally occurring microRNA cluster, such as those having heterologous nucleic acid sequences.

By "microRNA hairpin," "microRNA hairpin domain," or "microRNA hairpin sequence" is meant a portion of the microRNA having the biologically active sequence that is antisense or partially antisense to a target sequence. The microRNA hairpin contains a stem and stem loop domain, wherein the stem domain contains a short (e.g., typically 6-8) nucleotide seed region that hybridizes with a target sequence (e.g. an mRNA target sequence). As used herein, the microRNA hairpin may refer to a hairpin found in naturally occurring microRNAs or microRNA clusters or a hairpin. Alternatively, the microRNA hairpin may refer to a heterologous sequence inserted into an artificial microRNA or microRNA cluster, as described herein.

By "microRNA scaffold" is meant the genetic backbone of a microRNA that generally excludes the microRNA hairpin sequence. As described herein, the microRNA scaffold may contain in a 5' to 3' direction a 5' flanking sequence, a pair of donor acceptor sites (e.g. base of stem sequences) for attaching one microRNA hairpin domain, and a 3' flanking sequence.

By "microRNA cluster scaffold" is meant the genetic backbone of a microRNA cluster that generally excludes one or more of the microRNA hairpin sequences. As described herein, the microRNA cluster scaffold may contain in a 5' to 3' direction a 5' flanking sequence, two or more pairs of acceptor sites for attaching two or more microRNA hairpin domains, spacer sequences separating any two hairpin sequences, and a 3' flanking sequence.

By "microRNA sponge sequence" is meant a nucleic acid sequence (e.g. a non-coding RNA sequence) that is antisense or partially antisense to a target sequence (e.g. a microRNA nucleotide sequence). Non-coding RNAs having a microRNA sponge sequence may, upon binding to a microRNA (e.g. miR-21), lead to its cleavage, degradation, destabilization, and/or regulation (e.g., regulating its binding to a target mRNA). A microRNA sponge sequence may be encoded into the artificial microRNA or microRNA cluster compositions described herein. Any biological activity associated with the function of a microRNA sponge sequence is referred to as "microRNA sponge activity."

By "non-coding RNA" and "non-coding RNA sequence" is meant a sequence of RNA or a gene encoding the RNA that does not encode a protein or polypeptide. Non-coding RNAs include the microRNA and microRNA cluster compositions described herein as well as any of their component elements (e.g. 5' and 3' flanking sequences, spacer sequences, hairpin sequences including stem and stem loop sequences, base of stem sequences, aptamer sequences, microRNA sponge sequences, among others). Non-coding RNA sequences that may be introduced into the microRNA compositions described herein may have virtually any function associated with non-coding RNAs such as, for example, scaffolds for proteins, modifiers of pro-mRNA splicing, transfer-RNAs, short interfering RNAs, short hairpin RNAs, ribosomal RNAs, Piwi-interacting-RNAs, small nucleolar RNAs, small nuclear RNAs, extracellular RNAs, small Cajal body-specific RNAs, long non-coding RNAs.

By "non-naturally occurring microRNA" is meant a microRNA or microRNA cluster molecule which contains segments or regions of nucleic acid sequences that are not normally found in nature (e.g. heterologous sequences). As a non-limiting example, a microRNA normally found in nature may be transformed into a non-naturally occurring microRNA by way of replacing the 5' and/or 3' flanking sequences flanking the microRNA hairpin sequence. As another non-limiting example, a microRNA cluster normally found in nature may be transformed into a non-naturally occurring microRNA cluster by way of replacing the microRNA hairpin sequences with other microRNA hairpin sequences not found within the cluster in nature, by way of replacing the 5' and/or 3' flanking sequences at the 5' and/or 3' ends of the microRNA cluster with other non-coding RNA sequences (e.g. microRNA sponge or aptamer sequences, among others), by way of replacing the spacer sequences of the microRNA cluster with other non-coding RNA sequences (e.g. microRNA sponge or aptamer sequences, among others), or by way of any other modifications that result in a microRNA or microRNA molecules not found in nature.

By "operably linked" is meant a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

By "promoter" is meant a recognition site on DNA that is bound by an RNA polymerase. The polymerase drives transcription of the transgene. Additionally, the term "promoter" may refer to a synthetic promoter, which are regulatory DNA sequences that do not occur naturally in biological systems. Synthetic promoters contain parts of naturally occurring promoters combined with polynucleotide sequences that do not occur in nature and can be optimized to express recombinant DNA using a variety of transgenes, vectors, and target cell types. As described herein, a promoter may be "endogenous" to a eukaryotic cell when it is normally found or expressed in the cell. A promoter may be heterologous to a eukaryotic cell when if it is not normally found or expressed within the cell.

By "spacer sequence" is meant a sequence of nucleotides encoding a non-coding RNA that separates any two microRNA hairpin sequences contained within a microRNA cluster. Generally, the spacer sequence is longer than 20 nucleotides. As described herein, a spacer sequence may be a homologous spacer sequence native to a particular microRNA cluster. Alternatively, the spacer sequence may be heterologous with respect to a particular microRNA cluster and may include non-coding RNA sequences having a specified biological activity (e.g., microRNA sponge activity, aptamer activity, among others).

By "target sequence" is meant a DNA or RNA sequence targeted by a microRNAs, microRNA clusters, or any associated non-coding RNA sequences. A target sequence may be present in a protein-coding primary transcript or mRNA, in a microRNA (e.g. miR-21), in a regulatory sequence associated with a gene, or any other DNA or RNA sequence subject to regulation within a cell (e.g. a mammalian cell). The term "target sequence" may also refer to a nucleic acid sequence (e.g. a microRNA nucleic acid sequence) that is targeted by a microRNA sponge sequence.

By "vector" is meant a nucleic acid vector, e.g., a DNA vector, such as a plasmid, a RNA vector, virus, or other suitable replicon (e.g., viral vector). A variety of vectors have been developed for the delivery of polynucleotides encoding exogenous nucleic acids into a prokaryotic or eukaryotic cell. Expression vectors suitable for use with the compositions and methods described herein may contain a polynucleotide sequence as well as, e.g., additional sequence elements used for the expression of or the integration of these polynucleotide sequences into the genome of a mammalian cell. Certain vectors that can be used herein include plasmids that contain regulatory sequences, such as promoter and enhancer regions, which direct gene transcription. Other useful vectors contain polynucleotide sequences that improve the stability or nuclear export of the mRNA that results from gene transcription. These sequence elements may include, e.g., 5' and 3' untranslated regions, an IRES, and polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker are genes that encode resistance to antibiotics, such as ampicillin, chloramphenicol, kanamycin, nourseothricin, or zeocin.

The present invention provides a number of advantages. For example, the methods and artificial microRNA compositions provide several advantages over existing approaches for targeted microRNA delivery for therapeutic treatment of human diseases or disorders. In one advantage, the invention provides methods and compositions for delivering multiple microRNAs in a single expression vector to target multi-protein cellular signaling pathways in a subject (e.g., a human subject). This advantage enables one having sufficient skill in the art to treat diseases or conditions associated with dysregulation of one or multiple proteins or microRNAs within the cells of the subject, therefore allowing for a target-based and mechanism-based therapy. In another example, microRNAs have relatively simple biogenesis and short lengths (for example, typically ~70 nucleotides in a precursor form) facilitating incorporation into virtually any expression vector suitable for therapeutic administration. In still another advantage, microRNAs are naturally occurring within normal (e.g. healthy) cells and therefore are less likely to produce an immunogenic response upon administration to the subject. This advantage allows microRNAs or microRNA clusters of the present invention to act as so-called endogenous drugs within a patient. In a further advantage, the invention provides for the construction and administration of microRNAs as well as non-coding RNA sequences that can be incorporated into the compositions described herein. Such non-coding RNA sequences are readily selected to have a variety of functions associated with non-coding RNA sequences. For example, the non-coding RNA sequences may encode antisense non-coding RNA sequences to target nucleic acids within the cells of the subject (e.g. target microRNAs, such as target microRNAs associated with a human disease or disorder). Such antisense non-coding RNA sequences (e.g. microRNA sponge sequences) may bind to target nucleic acids within the cells of the subject and lead to degradation, cleavage, or destabilization of the target nucleic acids. Furthermore, the non-coding sequences may encode aptamer sequences that can bind to target proteins to regulate their function, thereby expanding the therapeutic capacity of a single therapeutic microRNA construct. The non-coding RNA sequences that may be introduced into the microRNA compositions may include virtually any other function associated with non-coding RNAs such as, for example, scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, long non-coding RNAs. In still another advantage, the invention provides microRNA cluster compositions that may act synergistically to target proteins that cannot be regulated by the overexpression of a single microRNA. Advantageously, the invention provides for artificial microRNAs and microRNA clusters that may be transferred from cells targeted by an expression vector to bystander cells without necessitating physical cell-to-cell contact (e.g., by way of microvesicles), thereby providing an enhanced therapeutic effect that is amplified beyond the cells targeted by the vector. In still another advantage, methods of preparing artificial microRNAs and/or microRNA clusters are relatively fast.

Other features and advantages of the invention will be apparent from the following description, and from the claims.

BRIEF DESCRIPTION OF THE DRAWINGS

FIG. 1A shows a schematic representing the miR-17-92 cluster and its components. FIG. 1B shows the removal of native hairpins from the miR-17-92 cluster. The base of stem sequences remain intact, as well as the spacer sequences. FIG. 1C shows a schematic for the construction of an artificial miRNA. Here, the schematic shows the isolation of hairpins encoding microRNAs and their attachment to the base of stem sequences of miR-17-92. This allows for a reconstitution of the cluster structure with different microRNA-encoding hairpins. FIG. 1D shows a schematic image of the construction of miR-128-124 artificial microRNA cluster based on miR-17-92 cluster backbone. FIG. 1E shows the engineering of two artificial microRNAs: one containing miR-124, miR-128, and miR-137 ("Cluster 3") and another containing miR-124, miR-128, miR-137, miR-7, and miR-218 ("Cluster 5"). The genetic backbone of a naturally existing microRNA cluster (miR-17-92) is removed from the native microRNA hairpin structures and replaced with therapeutic microRNA hairpins of choice as in Cluster 3 and Cluster 5.

FIG. 2A shows a volcano plot depicting various deregulated microRNAs in GBM (n=520) vs normal brain (n=10), generously provided by Dr. Josie Hayes of University of California, San Francisco. Measures of microRNA expression were obtained from The Cancer Genome Atlas (TCGA) database. FIG. 2B shows a pooling of TCGA data on microRNA expression, showing 10 downregulated (including miR-124, miR-128, miR-137, miR-7, and miR-218) and 5 upregulated microRNAs in GBM (including miR-21). FIG. 2C shows qRT-PCR data, evidencing clustering of miR-124, miR-128, and miR-137 during induced neuronal differentiation. FIG. 2D illustrates known targets of miR-124, miR-128, and miR-137, namely the epigenetic proteins BMI1 proto-oncogene polycomb ring finger (BMI1), enhancer of zeste 2 polycomb repressive complex 2 subunit (EZH2), and lysine demethylase 1A (LSD1), respectively. FIG. 2E shows a western blot of epigenetic proteins BMI1, EZH2, and LSD1, targets of miR-124, miR-128, and miR-137, displaying an inverse correlation with the 3 microRNAs in neuronal differentiation. FIG. 2F shows protein quantification of epigenetic regulator proteins LSD1, EZH2, and BMI1 from healthy (Brain) brains and GBM brains.

FIG. 3A shows an artificial miR-128-124 cluster, termed "Cluster 2. " FIG. 3B shows qRT-PCR analysis of expression of miR-128 and miR-124 upon transduction of human GBM (G34) cells with Cluster 2, demonstrating that the microRNA hairpins of the artificial cluster were correctly processed and expressed. FIG. 3C shows a series of western blots from cells expressing Cluster 2, demonstrating downregulation of known specific miR-124 targets, miR-128 targets, and common targets. FIG. 3D shows a clonal assay with GBM tumor initiating cells expressing either control, single microRNAs, or miR-128-124 genes. FIG. 3E shows a Kaplan-Meier plot, demonstrating survival differences among nude mice after intracranial injection of 50,000 GBM stem cells expressing either control, single microRNA, or miR-128-124 genes.

FIG. 4A shows a series of western blots demonstrating upregulated expression of epigenetic proteins upon single knock-down of either EZH2 or BMI1 in GBM cells in vitro. FIG. 4B shows western blots demonstrating upregulation of epigenetic proteins in GBM cells in vitro upon administration of a chemotherapeutic agent, temozolomide (TMZ; FIG. 4B, left and middle) or upon irradiation (FIG. 4B, right). FIG. 4C shows a schematic of an experiment in which a mouse model of GBM is left untreated or is treated with TMZ (FIG. 4C, left). Tumors were analyzed in both conditions using western blots, demonstrating that tumor cells from mice treated with TMZ showed upregulation of epigenetic proteins (FIG. 4C, right).

FIG. 5A shows a schematic image demonstrating that the genomic sequence encoding cluster miR-17-92 was removed of its native microRNAs, which were replaced with different numbers of microRNAs of choice, while leaving the intervening spacer sequences intact, generating Cluster 3, Cluster 5, Cluster 6. As a control, a separate cluster having a scrambled sequence of Cluster 3 was also produced. Also included in FIG. 5A are secondary structures of the microRNA cluster sequences for Cluster 3, scrambled Cluster 3, and Cluster 6. The DNA sequences were then cloned into retroviral (lentiviral) vectors (pCDH) and virus particles were used to create stable cell lines. FIG. 5B shows qRT-PCR from glioblastoma initiating cells (GCI) infected for 1 week with virus particles encoding for each microRNA individually or Cluster 3, scrambled Cluster 3, Cluster 5, or Cluster 6. The expression of each one of the microRNAs was verified. The scrambled Cluster 3 sequence did not produce mature microRNAs, confirming the importance of sequence specificity for producing mature microRNAs encoded from artificial clusters. FIG. 5C shows western blots from the GIC cells described in FIG. 5B, including known targets of the microRNAs used within the clusters. FIG. 5D shows a PCR analysis, demonstrating the expression levels of microtubule associated protein 2 (MAP2) and tubulin beta 3 class III (TUBB3) genes, known to be involved in neuronal differentiation, after expression of single microRNAs or clustered microRNAs in G34 GBM cells. FIG. 5E shows a soft agar clonal assay with G34 cells overexpressing either GFP alone, versus single microRNAs, versus, clustered microRNAs (FIG. 5E, left). Bar graphs shows quantification of colonies (FIG. 5E, right). FIG. 5F (top) shows a survival curve of mice after intracranial implantation of 5,000 G34 cells transduced with either GFP, single microRNAs, or clustered microRNAs. Hematoxylin and eosin stains of representative brain sections at day 12 after implantation are depicted below the survival curve. =p<0.01; **=p<0.0001.

FIG. 6A shows qRT-PCR data demonstrating reduced expression of naturally-expressed miR-124, miR-128, and miR-137 in GICs following treatment with TMZ, as compared to control conditions. FIG. 6B shows fluorescence-activated cell sorting (FACS) analysis for 7-aminoactinomycin D (7-AAD) intensity on the y-axis of the top two rows or propidium iodide on the y-axis of the bottom two rows, and annexin-V intensity on the x-axis, demonstrating that GICs overexpressing artificial microRNA clusters are markedly more susceptible to undergo cell death following treatment with TMZ or radiation. FIG. 6C shows a western blot analysis of cell lysates from G34 cells, showing that microRNA Cluster 3 prevents the upregulation of epigenetic proteins upon treatment with TMZ, an effect that is absent in the control transgene. FIG. 6D shows the quantification of protein levels shown in the western blots of FIG. 6C. FIG. 6E shows a proliferation assay of G34 cells in culture with 15 µM TMZ treatment (right panel) and without (left panel), quantifying the cell count per well of cells treated with a control transgene, one of individual miR-124, miR-128, or miR-137, or a transgene encoding microRNA Cluster 3. Co-treatment of G34 cells with Cluster 3 and GBM resulted in a profound reduction in cancer cell proliferation, as compared to the control transgene, or transgenes encoding single microRNAs. FIG. 6F shows an experiment in which GICs overexpressing either negative control or Cluster 3 or Cluster 5 were implanted intracranially in athymic nude mice (n=6) and mice were treated with 20 mg/kg/day of TMZ for 5 days starting at day 6 after implantation. Solid lines represent animals which did not receive TMZ. Dotted lines represent animals treated with TMZ. Different line colors represent the different overexpressed clusters.

FIG. 7A shows an schematic drawing of an experiment in which 5,000 GICs stably expressing RFP (RFP+ cells) were mixed intracranially at a 1:1 ratio with GFP-expressing (GFP+) GICs expressing either negative control or Cluster 3 transgene. At time of sacrifice, the tumors were collected and RFP+ and GFP+ cells were isolated by FACS. FIG. 7B shows qRT-PCR analysis demonstrating microRNA expression from sorted cells. RFP+ cells that were not directly transduced with the Cluster 3 transgene showed robust overexpression of microRNAs expressed by the cluster. FIG. 7C shows a western blot analysis of epigenetic protein levels in RFP+ cells mixed with GFP+ control cells or GFP+ cells expressing Cluster 3 in vivo. Levels of epigenetic regulators were significantly reduced only in RFP+ cells mixed with Cluster 3-expressing GFP+ cells, suggesting that transferred microRNAs were biologically active. FIG. 7D shows a survival plot of mice injected intracranially with RFP+ cells either alone or at a 1:1 ratio with GFP+ cells expressing negative control or Cluster 3 transgene. n.s.=non-significant. ***=p<0.0001. FIG. 7E shows a confocal microscopy image of one representative brain section per group sacrificed at day 12, showing the two cell populations at low magnification and ×20 magnification. Scale bars: 1 mm (whole slide); 100 μm (insets).

FIG. 8A shows a schematic of a trans-well assay used for microRNA transfer analysis. GFP+ cells expressing a control transgene, individual microRNAs (124, 128, 137), or Cluster 3 ("Donor" cells) were co-cultured in a well that separated them from RFP+ cells ("Receiver" cells) by a semipermeable membrane that precluded physical cell-to-cell contact between the two cell populations but allows for passage microvesicles. FIG. 8B shows fluorescent microscope images of G34 neurospheres in different co-culturing conditions. Delivery of single microRNA constructs had no effect on clonogenicity of Receiver cells and only a modest effect on the Donor cells. FIG. 8C shows the same experiments described above, but with the Donor cells expressing Cluster 3. Under these conditions, both the Donor cells and the Receiver cells showed a dramatic decrease in colony formation.

FIG. 9A shows a survival curve of mice receiving tumor cell implants at day 0, followed by intratumoral delivery of AAV2 vectors expressing Cluster 3 at day 5. Mice receiving Cluster 3-expressing AAV2 vectors showed almost a 3 fold increase in survival (FIG. 9A) and a reduced tumor burden (FIG. 9B), despite the absence of any other treatments.

FIG. 10C shows PCR analysis from cytoplasmic (Cy) and nuclear (Nu) extracts, confirming the persistence and distribution of the 5' and 3' flanking sequences and spacer sequences.

FIG. 11A shows qRT-PCR analysis from GBM cells, demonstrating expression of different microRNAs after transduction with a control transgene (ctrl), a transgene encoding Cluster 3 (CL3), or a transgene encoding Cluster 3 with the anti-miR-21 sequence in its 5' flanking region (CL3-21). FIG. 11B shows a luciferase assay in HEK293 cells after transduction with a luciferase vector associated to a miR-21 responsive element in the 3' UTR. FIG. 11C shows a western blot demonstrating downregulation of epigenetic proteins targeted by microRNAs, and upregulation of known targets of miR-21 (e.g., phosphatase and tensin homolog (PTEN)). FIG. 11D shows cell counts from proliferation assay of GBM cells transduced with different transgenes. FIG. 11E shows a scratch assay of GBM cells expressing different transgenes. FIG. 11F shows the quantification of the size of the gap from the scratch assay shown if FIG. 11E.

FIG. 12A shows qRT-PCR analysis demonstrating expression level of microRNAs after transduction with control transgenes (ctrl), transgenes encoding Cluster 3 (CL3), transgenes encoding Cluster 3 having an anti-miR-21 sequence in the 5' flanking sequence (CL3-21), or transgenes encoding Cluster 3 having the anti-miR-21 sequences as described above and a spacer sequence encoding an aptamer sequence targeted against the p50 protein (CL3-21-ap50). FIG. 12B shows a western blot representing targets of either microRNAs (EZH2, BMI1, LSD1, and PTEN) or the nuclear factor kappa B subunit 1 (NFκB) pathway (COX-2). Programmed death ligand 1 (PDL1) was also tested for its immunological role and also as a known downstream target of PTEN. FIG. 12C shows an assessment of the NFκB pathway activation by luciferase expression in HEK293 cells. FIG. 12D shows representative photomicrographs of GBM cell colony formation in culture after expression of aforementioned transgenes. FIG. 12E shows cell counts from the cell culture of FIG. 12D.

DETAILED DESCRIPTION

Figure 1A:
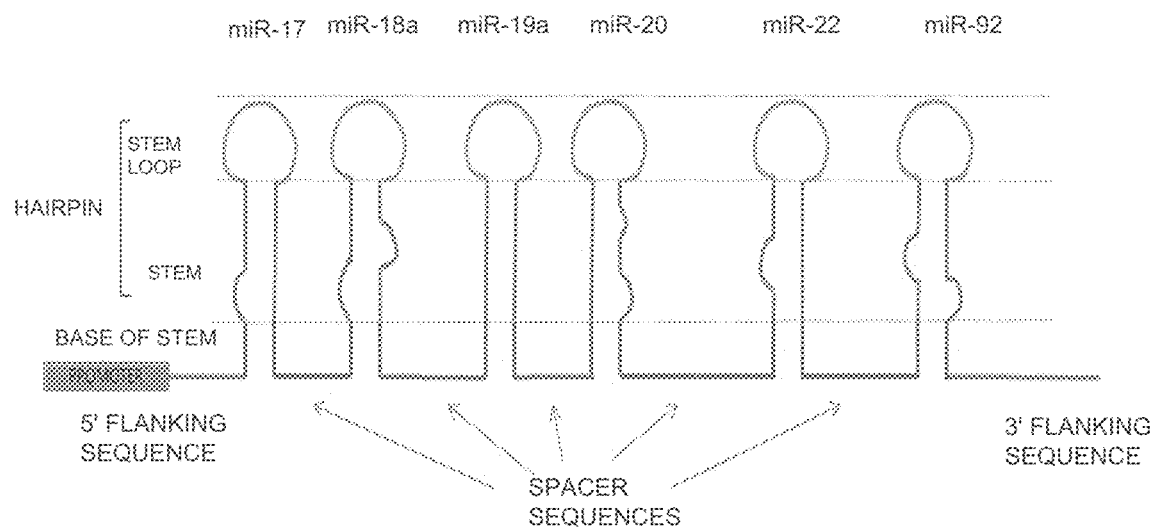
FIGS. 1A-1E show a series of schematics demonstrating the construction of artificial microRNA clusters.

Described herein are compositions and methods for the treatment of a disease (e.g., cancer, such as glioblastoma multiforme (GBM), leukemia, breast cancer, or thyroid cancer, among others) in a subject (such as a mammalian subject, for example, a human) using artificial (e.g., non-naturally occurring) microRNAs or artificial microRNA clusters. In some embodiments, the disease may be associated with dysregulated (e.g., increased or decreased) expression or activity of single or multiple microRNAs and/or proteins. Using the compositions and methods described herein, one can treat a disease in a subject by administering an expression vector including transgene constructs encoding an artificial microRNA or artificial microRNA cluster compositions (e.g., compositions described herein). For example, described herein are compositions that include single artificial microRNAs or artificial microRNA clusters and methods of treatment of a subject having a disease (e.g., cancer, such as GBM, leukemia, breast cancer, or thyroid cancer, among others) using the compositions. Also described are methods for preparing non-naturally occurring microRNAs and microRNA clusters. The sections that follow describe the methods and compositions useful for treatment of a disease.

MicroRNA

MicroRNAs are short (typically about ~22 nucleotide) sequences of non-coding RNA that broadly regulate mRNA translation and thus influence target protein abundance. Some microRNAs are transcribed as single genes (e.g., miR-124, miR-128, miR-137, miR-7, miR-218, miR-34, among others), while others are part of clusters (e.g., miR- 17-92, miR-367-302, miR-181a-b, miR-24-23-27, and miR-143-145, among others). The biologically active component (e.g., biologically active sequence) of microRNAs is contained in the "stem" domain (e.g., stem sequence) of microRNA "hairpins" domains (e.g., hairpin sequence). The stem sequences of the microRNA hairpin domains act by complementary base-pairing with hundreds of target mRNA molecules, usually by binding within the 3' untranslated region (3'UTR), thereby leading to cleavage of the mRNA strand, destabilization of the mRNA by shortening its poly (A)-tail, and/or less efficient translation of the mRNA. In animals, microRNAs are capable of recognizing their target mRNAs using only about 6-8 nucleotides within their seed region near the 5' end of the microRNA molecule and, at times, several microRNAs may work in a combinatorial fashion to target a single mRNA. In some embodiments, the biologically active sequence of the stem domain of an artificial microRNA or artificial microRNA cluster is antisense or partially antisense to a target sequence (e.g., a target mRNA sequence). In some embodiments, the target mRNA sequence is an mRNA encoding the enhancer of zeste 2 polycomb repressive complex 2 subunit (EZH2) protein, the signal transducer and activator of transcription 3 (STAT3) protein, the BMI1 proto-oncogene polycomb ring finger (BMI1) protein, the lysine demethylase 1A (LSD1) protein, the embryonic ectoderm development (EED) protein, the epidermal growth factor receptor (EGFR) protein, the roundabout guidance receptor (ROBO1) protein, the ret proto-oncogene (RET) protein, the MET proto-oncogene receptor tyrosine kinase (c-MET) protein, the MYC proto-oncogene BHLH transcription factor (MYC) protein, the phosphatase and tensin homolog (PTEN) protein, and/or the programmed cell death 4 (PDCD4) protein.

MicroRNAs have several unique features which make them ideally suited to be exploited for targeting multi-protein cellular pathways, like epigenetic protein complexes, including: 1) their relatively simple biogenesis and structure which are amenable to genetic manipulation; 2) with a length of only about ~70 nucleotides in their precursor forms, they are the smallest genes encoded by the human genome, making them ideal for a combinatorial approach; 3) microRNAs can be shed from microvesicles, suggesting a potential for a bystander effect; 4) microRNAs naturally occur within normal cells, therefore minimizing side effects as a result of their reintroduction in vivo; 5) many microRNAs exist in nature associated in clusters, suggesting their tendency to work in combination.

Naturally Occurring microRNA Clusters

Naturally occurring microRNAs are transcribed as single genes encoding one microRNA (e.g., monocistronic transcripts) or as polycistronic genes encoding multiple microRNAs in a gene cluster (e.g., a naturally occurring microRNA cluster). Typical naturally occurring microRNA clusters include two or three microRNA such as miR-181a-b, miR-143-145, and miR-24-23-27, but larger clusters, such as the miR-17-92 composed of six microRNAs, miR-367-302 composed of five microRNAs, also exist. Deregulation of polycistronic microRNA clusters such as miR-17-92 have been identified as oncogenic drivers in cancer through metabolic reprogramming of cells, a feature of cancer required to sustain the demands of sustained malignant growth and proliferation. The methods and compositions described herein employ naturally occurring polycistronic microRNA clusters to construct artificial clusters in which the normally oncogenic, deleterious, or disadvantageous microRNA hairpin domains are replaced with therapeutically beneficial microRNAs, as described in detail below.

Artificial microRNAs and microRNA Clusters
Construction of Artificial microRNA Clusters Gene therapy research and application usually focuses on the delivery of single genes, mostly due to the limitation of the size of the gene to be delivered to cells, making it difficult to deliver multiple genes simultaneously. The invention is based, in part, on the idea that microRNAs have two unique characteristics: 1) They are typically very short nucleotide sequences; and 2) clusters of microRNAs within short DNA segments occur in nature. The invention is further based, in part, on the use of one or more naturally occurring DNA sequences of microRNA clusters as a backbone genetic structure (also referred to herein as a scaffold) in which the native, naturally occurring microRNAs are replaced with selected microRNAs of choice. This methodology creates an artificial cluster of microRNAs to be processed normally by the cell in view of its native DNA backbone scaffolding. This allows for the simultaneous, effective, delivery of multiple microRNAs of choice to mammalian cells to investigate their synergistic effect in cell biology.

The creation of an artificial microRNA cluster allows for the generation a multitude of useful gene therapy approaches based on simultaneous multiple microRNA delivery. Because of the small size of microRNAs and the existence in nature of DNA sequences that are able to produce multiple microRNAs simultaneously, the invention envisions that this engineering approach will translate into the creation of gene delivery vectors useful for not only the investigation but also the treatment of any number of human diseases (e.g., cancer, such as GBM, leukemia, breast cancer, or thyroid cancer, among others). Moreover, as is disclosed herein, the principle of modifying the genetic backbone (e.g. scaffold) of naturally occurring microRNAs to incorporate therapeutically relevant segments of microRNAs (e.g., 5' and 3' flanking sequences or hairpin sequences) similarly applies for delivery of single artificial microRNAs.

The invention further includes methods and compositions for using and preparing artificial microRNAs or artificial microRNA clusters in treatment of a disease (e.g., cancer, such as GBM, leukemia, breast cancer, or thyroid cancer, among others). Such artificial microRNAs and or microRNA clusters may be based on and/or derived from the genetic backbone (e.g., microRNA scaffold or microRNA cluster scaffold) of a naturally occurring microRNA or microRNA cluster. A non-limiting example for the construction of an artificial microRNA cluster is described in Example 1. In this example, a naturally occurring miR-17-92 microRNA cluster is used to provide a scaffold upon which microRNAs of interest that do not naturally occur in miR-17-92 may be added in place of native microRNAs of the cluster for use as a therapeutic agent in the treatment of a disease (e.g., cancer, such as GBM, leukemia, breast cancer, or thyroid cancer, among others).

In some embodiments, the method of preparing an artificial (e.g., non-naturally occurring) microRNA cluster is performed in silico. In some embodiments, the method of preparing the artificial microRNA cluster includes providing a microRNA cluster scaffold. In some embodiments, the microRNA scaffold is based on or derived from a naturally occurring microRNA cluster (e.g., a miR-17-92 cluster, a miR-367-302 cluster, a miR-181a-b cluster, or a miR-24-23-27 cluster, among others). In some embodiments, the microRNA cluster scaffold includes a 5' flanking sequence. In some embodiments, the microRNA cluster scaffold includes two or more pairs of acceptor sites for attaching two or more microRNA hairpin domains that are not naturally occurring within the scaffold (e.g., are heterologous with respect to the scaffold). In some embodiments, the pairs of acceptor sites are short nucleotide sequences (e.g., 3-21 nucleotides long) that are based on or derived from the hairpin domains of the naturally occurring microRNA cluster-based scaffold. In some embodiments, the pairs of acceptor sites are based on non-coding RNA sequences within the artificial microRNA cluster. In some embodiments, the pairs of acceptor sites include a 5' and a 3' acceptor site. In some embodiments, the microRNA cluster scaffold includes one or more spacer sequences. In some embodiments, the microRNA cluster scaffold includes a 3' flanking sequence. In some embodiments, the method of preparing the artificial microRNA cluster further includes attaching two or more microRNA hairpin domains to the two or more pairs of acceptor sites.

In some embodiments, the method of preparing an artificial (e.g., non-naturally occurring) microRNA is performed in silico. In some embodiments, the method of preparing the artificial microRNA includes providing a microRNA scaffold. In some embodiments, the microRNA scaffold is based on or derived from naturally occurring microRNAs or microRNA clusters (e.g., a miR-17-92 cluster, a miR-367-302 cluster, a miR-181a-b cluster, or a miR-24-23-27 cluster, among others). In some embodiments, the microRNA scaffold includes a 5' flanking sequence. In other embodiments, the microRNA cluster scaffold includes a pair of acceptor sites for attaching a microRNA hairpin domain that is not naturally occurring within the scaffold (e.g., is heterologous with respect to the scaffold). In yet other embodiments, the pair of acceptor sites are short nucleotide sequences (3-21 nucleotides long) that are based on or derived from the hairpin domains of the naturally occurring microRNA-based or microRNA cluster-based scaffold. In certain embodiments, the pair of acceptor sites includes a 5' and a 3' acceptor site. In some embodiments, the pairs of acceptor sites are based on non-coding RNA sequences within the artificial microRNA cluster. In some embodiments, the artificial microRNA includes a 3' flanking sequence. In some embodiments, the method of preparing the artificial microRNA cluster further includes attaching a microRNA hairpin domain to the pair of acceptor sites.

Cancer

MicroRNA deregulation has been shown to be associated with many human diseases, including cancers. Cancer-associated microRNAs are termed "oncomirs" and contribute to cancer development and pathophysiology. For example, microRNAs are important to the development and function of B cells and specific signatures of microRNA deregulation are present in B-cell lymphomas. Other cancers associated with altered expression of microRNAs include colorectal cancer, ulcerative-colitis-associated colon cancers, hepatocellular carcinomas, Hodgkin lymphoma, cervical cancer, and GBM, among others. In some embodiments, the cancer associated with altered expression of microRNAs is GBM.

The compositions and methods described herein are useful for treating cancer in a subject by administering to the subject an effective amount of an artificial microRNA or microRNA cluster composition (e.g., a composition described herein). The method may include administering locally (e.g., intratumorally) to the subject a composition described herein in a dose (e.g., effective amount) and for a time sufficient to treat the cancer. For example, the stroma associated with the tumor, e.g., fibroblasts, is disrupted such that an essential function, e.g., the production of matrix metalloproteases, is altered to inhibit tumor survival or promote tumor control.

In some embodiments, the composition produces a therapeutic effect, including, but not limited to the effects described below. In some embodiments, the composition inhibits proliferation or disrupts the function of non-neural cells associated with the cancer, e.g., the method includes administering to the subject an effective amount of a composition (e.g., compositions disclosed herein) for a time sufficient to inhibit proliferation or disrupt the function of non-neural cells associated with the cancer. Non-neural cells associated with the cancer include malignant cancer cells, malignant cancer cells in necrotic and hypoxic areas, adipocytes, pericytes, endothelial cells, cancer associated fibroblasts, fibroblasts, mesenchymal stem cells, red blood cells, or extracellular matrix. The proliferation of non-neural cells associated with the cancer may be decreased in the subject at least 1%, 2%, 5%, 10%, 15%, 20%, 25%, 30%, 35%, 40%, 50%, 60%, 70%, 80%, 90%, 95% or more, compared to before the administration. The proliferation of non-neural cells associated with the cancer can be decreased in the subject between 5-20%, between 5-50%, between 10-50%, between 20-80%, between 20-70%.

The compositions described herein can treat cancer by increasing cancer cell death, or cancer cell autophagy in a subject (e.g., a human subject or animal model) or in a cancer cell culture (e.g., a culture generated from a patient tumor sample, a cancer cell line, or a repository of patient samples). A composition described herein can increase cancer cell death or cancer cell autophagy by at least 1%, 2%, 5%, 10%, 15%, 20%, 25%, 30%, 35%, 40%, 50%, 60%, 70%, 80%, 90%, 95% or more compared to before administration to a subject or cancer cell culture. A composition described herein can increase cancer cell death or cancer cell autophagy in a subject or cancer cell culture between 5-20%, between 5-50%, between 10-50%, between 20-80%, between 20-70%.

The compositions disclosed herein can also act to inhibit cancer cell growth, proliferation, metastasis, migration, or invasion, e.g., the method includes administering to the subject (e.g., a human subject or animal model) or a cancer cell culture (e.g., a culture generated from a patient tumor sample, a cancer cell line, or a repository of patient samples) a composition (e.g., composition disclosed herein) in an amount (e.g., an effective amount) and for a time sufficient to inhibit cancer cell growth, proliferation, motastasis, migration, or invasion. Cancer cell growth, proliferation, metastasis, migration, or invasion can be decreased in the subject or cancer cell culture at least 1%, 2%, 5%, 10%, 15%, 20%, 25%, 30%, 35%, 40%, 50%, 60%, 70%, 80%, 90%, 95% or more, compared to before the administration. Cancer cell growth, proliferation, metastasis, migration, or invasion can be decreased in the subject or cancer cell culture between 5-20%, between 5-50%, between 10-50%, between 20-80%, between 20-70%.

The compositions disclosed herein can also act to alter (e.g., increase or decrease) the expression level and/or activity of a protein or microRNA associated with the cancer (e.g., GBM, leukemia, breast cancer, or thyroid cancer, among others). For example, the compositions disclosed herein may reduce the expression level and/or activity of chromatin-modifying epigenetic regulator proteins such as, e.g., enhancer of zeste 2 polycomb repressive complex 2 subunit (EZH2), BMI1 proto-oncogene polycomb ring finger (BMI1), lysine demethylase 1 (LSD1), DNA methyltransferase 1 (DNMT1), and/or MYC proto-oncogene BHLH transcription factor (cMYC), by 10%, 15%, 20%, 25%, 30%, 35%, 40%, 45%, 50%, 55%, 60%, 65%, 70%, 75%, 80%, 85%, 90%, 95%, 99%, or more. In another example, the compositions disclosed herein may increase the expression level and/or activity of microRNAs associated with cancer (e.g., GBM, leukemia, breast cancer, or thyroid cancer, among others). For example, the compositions disclosed herein may increase the expression level and/or activity of miR-128, miR-124, miR-137, miR-7, miR-218, miR34, or any other microRNA associated with a disease (e.g. cancer, such as GBM, leukemia, breast cancer, or thyroid cancer, among others) in a cell (e.g. a mammalian cell) or in a subject by 10%, 15%, 20%, 25%, 30%, 35%, 40%, 45%, 50%, 55%, 60%, 65%, 70%, 75%, 80%, 85%, 90%, 95%, 99%, or more. Expression levels and or activity levels may be measured using standard methods known in the art such as, e.g., western blots, immunohistochemistry, immunoprecipitation, qRT-PCR, in situ hybridization, ELISA assay, among others.

Cancer Types

In the use of the compositions and methods described herein, the cancer or neoplasm may be any solid or liquid cancer and includes benign or malignant tumors, and hyperplasias, including CNS cancer including malignant glioma (e.g., GBM), gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g., head and neck squamous cell cancer); astrocytomas, retinoblastomas and brain metastases; malignant mesothelioma; non-metastatic or metastatic breast cancer (e.g., hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, leukemia, acute myelogenous leukemia, chronic myelogenous leukemia, myelodysplastic syndrome, acute lymphoblastic leukemia, Hodgkin's lymphoma). In some embodiments, the cancer is GBM. In some embodiments, the cancer is leukemia. In some embodiments, the cancer is breast cancer. In some embodiments, the cancer is thyroid cancer.

Additional cancers that can be treated according to the compositions and methods described herein include breast cancer, lung cancer, stomach cancer, colon cancer, liver cancer, renal cancer, colorectal cancer, prostate cancer, pancreatic cancer, cervical cancer, anal cancer, vulvar cancer, penile cancer, vaginal cancer, testicular cancer, pelvic cancer, thyroid cancer, uterine cancer, rectal cancer, brain cancer, head and neck cancer, esophageal cancer, bronchus cancer, gallbladder cancer, ovarian cancer, bladder cancer, oral cancer, oropharyngeal cancer, larynx cancer, biliary tract cancer, skin cancer, a cancer of the central nervous system, a cancer of the respiratory system, and a cancer of the urinary system. Examples of breast cancers include, but are not limited to, triple-negative breast cancer, triple-positive breast cancer, HER2-negative breast cancer, HER2-positive breast cancer, estrogen receptor-positive breast cancer, estrogen receptor-negative breast cancer, progesterone receptor-positive breast cancer, progesterone receptor-negative breast cancer, ductal carcinoma in situ (DCIS), invasive ductal carcinoma, invasive lobular carcinoma, inflammatory breast cancer, Paget disease of the nipple, and phyllodes tumor.

Other cancers that can be treated according to the methods described herein include leukemia (e.g., B-cell leukemia, T-cell leukemia, acute myeloid leukemia (AML), chronic myeloid leukemia (CML), acute lymphocytic (lymphoblastic) leukemia (ALL), chronic lymphocytic leukemia (CLL), and erythroleukemia), sarcoma (e.g., angiosarcoma, chondrosarcoma, Ewing's sarcoma, fibrosarcoma, gastrointestinal stromal tumor, leiomyosarcoma, liposarcoma, malignant peripheral nerve sheath tumor, malignant fibrous cytoma, osteosarcoma, pleomorphic sarcoma, rhabdomyosarcoma, synovial sarcoma, vascular sarcoma, Kaposi's sarcoma, dermatofibrosarcoma, epithelioid sarcoma, leyomyosarcoma, and neurofibrosarcoma), carcinoma (e.g., basal cell carcinoma, large cell carcinoma, small cell carcinoma, non-small cell lung carcinoma, renal cell carcinoma, hepatocarcinoma, gastric carcinoma, choriocarcinoma, adenocarcinoma, hepatocellular carcinoma, giant (or oat) cell carcinoma, squamous cell carcinoma, adenosquamous carcinoma, adrenocortical carcinoma, cholangiocarcinoma, Merkel cell carcinoma, DCIS, and invasive ductal carcinoma), blastoma (e.g., hepatoblastoma, medulloblastoma, nephroblastoma, neuroblastoma, pancreatoblastoma, pleuropulmonary blastoma, retinoblastoma, and glioblastoma multiforme), lymphoma (e.g., Hodgkin's lymphoma, non-Hodgkin's lymphoma, and Burkitt lymphoma), myeloma (e.g., multiple myeloma, plasmacytoma, localized myeloma, and extramedullary myeloma), melanoma (e.g., superficial spreading melanoma, nodular melanoma, lentigo maligna melanoma, acral lentiginous melanoma, and amelanotic melanoma), neuroma (e.g., ganglioneuroma, Pacinian neuroma, and acoustic neuroma), glioma (e.g., astrocytoma, oligoastrocytoma, ependymoma, brainstem glioma, optic nerve glioma, and oligoastrocytoma), pheochromocytoma, meningioma, malignant mesothelioma, and virally induced cancer.

In some embodiments, the cancer is a paraneoplastic cancer (e.g., a cancer that causes a paraneoplastic syndrome). Paraneoplastic syndromes are rare disorders that are triggered by an altered immune system response to a neoplasm, and are mediated by humoral factors such as hormones, cytokines, or auto-antibodies produced by the tumor. Symptoms of paraneoplastic syndrome may be endocrine, neuromuscular, or musculoskeletal, cardiovascular, cutaneous, hematologic, gastrointestinal, renal, or neurological. Paraneoplastic syndromes commonly present with lung, breast, and ovarian cancer and cancer of the lymphatic system (e.g., lymphoma). Paraneoplastic neurological disorders are disorders that affect the central or peripheral nervous system, and can include symptoms such as ataxia (difficulty with walking and balance), dizziness, nystagmus (rapid uncontrolled eye movements), difficulty swallowing, loss of muscle tone, loss of fine motor coordination, slurred speech memory loss, vision problems, sleep disturbances, dementia, seizures, or sensory loss in the limbs. Breast, ovarian, and lung cancers are most commonly associated with paraneoplastic neurological disorders. Other common types of paraneoplastic syndromes include paraneoplastic cerebellar degeneration, paraneoplastic pemphigus, paraneoplastic autonomic neuropathy, paraneoplastic encephalomyelitis, and cancer-associated autoimmune retinopathy.

Endocrine paraneoplastic syndromes include Cushing syndrome (caused by ectopic ACTH), which is most commonly caused by small coil lung cancer, pancreatic carcinoma, neural tumors, or thymoma; SIADH (caused by antidiuretic hormone), which is most commonly caused by small cell lung cancer and CNS malignancies; hypercalcemia (caused by PTHrp, TGFα, TNF, or IL-1), which is most commonly caused by lung cancer, breast carcinoma, renal and bladder carcinoma, multiple myeloma, adult T cell leukemia/lymphoma, ovarian carcinoma, and squamous cell carcinoma (e.g., lung, head, neck, or esophagus carcinoma); hyperglycemia (caused by insulin insulin-like substance, or "big" IGF-II), which is most commonly caused by fibrosarcoma, mesenchymal sarcomas, insulinoma, and hepatocellular carcinoma; carcinoid syndrome (caused by serotonin or bradykinin), which is most commonly caused by bronchial adenoma, pancreatic carcinoma, and gastric carcinoma; and hyperaldosteronism (caused by aldosterone), which is most commonly caused by adrenal adenoma/Conn's syndrome, non-Hodgkin's lymphoma, ovarian carcinoma, and pulmonary cancer.

Neurological paraneoplastic syndromes include Lambert-Eaton myasthenic syndrome (LEMS), which is most commonly caused by small cell lung cancer; paraneoplastic cerebellar degeneration, which is most commonly caused by lung cancer, ovarian cancer, breast carcinoma, and Hodgkin's lymphoma; encephalomyelitis; limbic encephalitis, which is most commonly caused by small cell lung carcinoma; myasthenia gravis, which is most commonly caused by thymoma; brainstem encephalitis; opsoclonus myoclonus ataxia (caused by autoimmune reaction against Nova-1), which is most commonly caused by breast carcinoma, ovarian carcinoma, small cell lung carcinoma, and neuroblastoma; anti-NMDA receptor encephalitis (caused by autoimmune reaction against NMDAR subunits), which is most commonly caused by teratoma; and polymyositis, which is most commonly caused by lung cancer, bladder cancer, and non-Hodgkin's lymphoma. Mucocutaneous paraneoplastic syndromes include acanthosis nigricans, which is most commonly caused by gastric carcinoma, lung carcinoma, and uterine carcinoma; dermatomyositis, which is most commonly caused by bronchogenic carcinoma, breast carcinoma, ovarian cancer, pancreatic cancer, stomach cancer, colorectal cancer, and Non-Hodgkin's lymphoma; Leser-Trelat sign; necrolytic migratory erythema, which is most commonly caused by glucoganoma; Sweet's syndrome; florid cutaneous papillomatosis; pyoderma gangrenosum; and acquired generalized hypertrichosis.

Hematological syndromes include granulocytosis (caused by G-CSF); polycythemia (caused by erythropoietin), which is commonly caused by renal carcinoma, cerebellar homangioma, and heptatocellular carcinoma; Trousseau sign (caused by mucins), which is commonly caused by pancreatic carcinoma and bronchogenic carcinoma; nonbacterial thrombotic endocarditis, which is caused by advanced cancers; and anemia, which is most commonly caused by thymic neoplasms. Other paraneoplastic syndromes include membranous glomerular nephritis; neoplastic fever; Staffer syndrome, which is caused by renal cell carcinoma; and tumor-induced osteomalacia (caused by FGF23), which is caused by hemangiopericytoma and phosphaturic mesenchymal tumor.

In some embodiments, a subject is identified as having cancer after presenting with symptoms of a paraneoplastic syndrome. A common symptom of paraneoplastic syndrome is fever. Auto-antibodies directed against nervous system proteins are also frequently observed in patients with paraneoplastic syndromes, including anti-Hu, anti-Yo, anti-Ri, anti-amphiphysin, anti-CV2, anti-Ma2, anti-recoverin, anti-transducin, anti-carbonic anhydrase II, anti-arrestin, anti-GCAP1, anti-GCAP2, anti-HSP27, anti-Rab6A, and anti-PNR. Other symptoms that can be used to identify a patient with paraneoplastic cancer include ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs. In some embodiments, a patient presents with symptoms of paraneoplastic syndrome and is then identified as having cancer based on imaging tests (e.g., CT, MRI, or PET scans).

The cancer may be metastatic, non-metastatic cancer, or benign (e.g., a benign tumor). The cancer may be a primary tumor or a metastasized tumor.

In some embodiments, the cancer is associated with dysregulated expression and/or activity (increased or decreased expression and or activity) of microRNAs and/or epigenetic regulator proteins with respect to normal, non-cancerous tissue from the subject.

Glioblastoma Multiforme

With a median survival of 14.6 months, GBM is the most aggressive and common malignant primary brain tumor in adults. A wealth of data derived from gene expression analysis over the past decade has shown that deregulation of microRNA expression is a hallmark of this tumor. Several microRNAs have been studied in the context of GBM and found to be important to its biology. MicroRNAs have been postulated to be particularly important for the fine tuning of complex biological pathways, due to their broad targeting capacity, and their fundamental role in regulating the expression of target proteins. One of the most crucial functions regulating cell biology is epigenetic control of gene expression. This is orchestrated by a complex of multiple epigenetic regulator proteins which interact with DNA and nucleosomes, determining the so called histone code. A constant feature of GBM is the deregulation of many of these proteins, resulting in impaired cell differentiation and permanence of stem traits, a characteristic of glioblastoma initiating cells (GIC). These features are considered by many the major culprits responsible for tumor propagation and resistance to treatment. Polycomb repressive complexes and (PRC1, PRC2), as well as DNA methyltransferases (DNMTs), histone deacetylases (HDACs), histone demethylases, like LSD1, and several transcription factors, including MYC, are all important effectors of this epigenetic regulation machinery. Therefore, GBM treatment is highly difficult as there are no currently available therapies that target multi-protein epigenetic signaling networks. Available treatment modalities for GBM locus largely on palliative treatment and symptom management, underscoring the need for new therapeutic avenues.

Unlike the available treatment modalities for GBM, which only treat disease symptoms, the compositions and methods described herein provide the benefit of treating a biological phenomenon that can underlie GBM, e.g., targeting multi-protein epigenetic regulator protein complexes involved in GBM pathogenesis and maintenance. As such, the compositions and methods described herein target the physiological cause of the disease, representing a potential curative therapy. The compositions and methods disclosed herein may be used in treatment of a subject having GBM by administering expression vectors including polynucleotides that encode artificial microRNAs or microRNA cluster compositions. These compositions and methods can be used to treat GBM with any etiology, e.g., genetic mutation, environmental toxin, or idiopathic. These compositions and methods can also be used to treat subjects having GBM associated with dysregulated expression and/or activity (increased or decreased expression and or activity) of microR- NAs and/or epigenetic regulator proteins. These compositions and methods can also be used to treat subjects having GBM associated with normal expression and/or activity of microRNAs and/or epigenetic regulator proteins.

Expression of microRNA Clusters in Mammalian Cells

Polynucleotides Encoding Artificial microRNA Clusters

Constructs encoding artificial (e.g., non-naturally occurring) microRNAs or artificial microRNA clusters that may be used in conjunction with the compositions and methods described herein include transgene constructs including polynucleotides encoding 1 or more (e.g., 1, 2, 3, 4, 5, or 6) microRNA hairpin domains. In some embodiments the construct includes a polynucleotide encoding 1 microRNA hairpin domain (e.g., any one of miR-128, miR-124, miR-137, miR-7, miR-218, miR-34, among others). In some embodiments the construct includes a polynucleotide encoding 2 microRNA hairpin domains (e.g., any one of miR-128, miR-124, miR-137, miR-7, miR-218, miR-34, among others). In some embodiments the construct includes a polynucleotide encoding 3 microRNA hairpin domains (e.g., any one of miR-128, miR-124, miR-137, miR-7, miR-218, miR-34, among others). In some embodiments the construct includes a polynucleotide encoding 4 microRNA hairpin domains (e.g., any one of miR-128, miR-124, miR-137, miR-7, miR-218, miR-34, among others). In some embodiments the construct includes a polynucleotide encoding 5 microRNA hairpin domains (e.g., any one of miR-128, miR-124, miR-137, miR-7, miR-218, miR-34, among others). In some embodiments the construct includes a polynucleotide encoding 6 microRNA hairpin domains (e.g., any one of miR-128, miR-124, miR-137, miR-7, miR-218, miR-34, among others).

In some embodiments, an artificial microRNA construct that includes 2 or more microRNA hairpin domains is an artificial microRNA cluster. In some embodiments, the artificial microRNA cluster construct includes a polynucleotide encoding the nucleic acid sequence of any one of SEQ ID NO. 1-6, or a variant thereof such as a polynucleotide encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 1-6, as described below.

In some embodiments, the artificial microRNA cluster construct includes a miR-128 5' flanking sequence, a miR-128 hairpin, a first miR-17-92 spacer sequence, a miR-124 hairpin domain, and a miR-128 3' flanking sequence and has the nucleic acid sequence of SEQ ID NO. 1.

```
                                           (SEQ ID NO. 1)
CTTTTCAATTTGAAGAGAGTGCTTCCTCTGTTCTTAAGGGGCTAGGGA

ACCAAATTAGGTTGTTTCAATATCGTGCTAAAAGATACTGCCTTTAGA

AGAAGGCTATTGACAATCCAGCGTGTCTCGGTGGAACTCTGACTCCAT

GGTTCACTTTCATGATGGCCACATGCCTCCTGCCCAGAGCCCGGCAGC

CAGTCCAGTGGGAAGGGGGCCGATACACTGTACGAGAGTGAGTAGCA

GGTCTCACAGTGAACCGGTCTCTTTCCCTACTGGACAGCTGCCTCGGG

AAGCCAAGTTGGGCTTTAAAGTGCAGGGCCTGCTGATGTTGAGTGCTT

TTTGTTGGCCTCTCTCTCCGTGTTCACAGCGGACCTTGATTTAAATGT

CCATACAATTAAGGCACGCGGTGAATGCCAAGAATGGGGCTGGCAACA

CTCCTAATGGAATGCCGTTATCCAAAGAGCAGCACGAACCCGACAGGG
```

```
CTGAGTGGCTTGTGCTAGGGAGAGGTTTGTGTCATTCCTGCTGACCAA

ACTGCAGGAAAAACTGCTAATTGTCATGCTGAAGACTGCCTGACGGGG

AGACTCTGCCTTCTGTAAGTAGGTCATGTAAAGAGCACGTGCTCCTTG

CTGCT
```

In some embodiments, the artificial microRNA cluster construct includes a miR-128 5' flanking sequence, a miR-128 hairpin, a first miR-17-92 spacer sequence, a miR-124 hairpin domain, a second miR-17-92 spacer sequence, a miR-137 hairpin domain, and a miR-128 3' flanking sequence and has the nucleic acid sequence of SEQ ID NO. 2 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 2.

```
                                           (SEQ ID NO. 2)
CTTTTCAATTTGAAGAGAGTGCTTCCTCTGTTCTTAAGGGGCTAGGGA

ACCAAATTAGGTTGTTTCAATATCGTGCTAAAAGATACTGCCTTTAGA

AGAAGGCTATTGACAATCCAGCGTGTCTCGGTGGAACTCTGACTCCAT

GGTTCACTTTCATGATGGCCACATGCCTCCTGCCCAGAGCCCGGCAGC

CAGTCCAGTGGGAAGGGGGCCGATACACTGTACGAGAGTGAGTAGCA

GGTCTCACAGTGAACCGGTCTCTTTCCCTACTGGACAGCTGCCTCGGG

AAGCCAAGTTGGGCTTTAAAGTGCAGGGCCTGCTGATGTTGAGTGCTT

TTTGTTGGCCTCTCTCTCCGTGTTCACAGCGGACCTTGATTTAAATGT

CCATACAATTAAGGCACGCGGTGAATGCCAAGAATGGGGCTGGCATAA

GAAGTTATGTATTCATCCAATAATTCAAGCCAAGCAAGTATATAGGTG

TTTTAATAGTTTTTGTTTGCACTGACTCTCTTCGGTGACGGGTATTCT

TGGGTGGATAATACGGATTACGTTGTTATTGCTTAAGAATACGCGTAG

TCGAGGAGAGTACCAGTGCACACTCCTAATGGAATGCCGTTATCCAAA

GAGCAGCACGAACCCGACAGGGCTGAGTGGCTTGTGCTAGGGAGAGGT

TTGTGTCATTCCTGCTGACCAAACTGCAGGAAAAACTGCTAATTGTCA

TGCTGAAGACTGCCTGACGGGGAGACTCTGCCTTCTGTAAGTAGGTCA

TGTAAAGAGCACGTGCTCCTTGCTGCT
```

In some embodiments, the artificial microRNA cluster construct includes a miR-128 5' flanking sequence, a miR-128 hairpin, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 hairpin domain, and a miR-128 3' flanking sequence and has the nucleic acid sequence of SEQ ID NO. 3 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 3.

(SEQ ID NO. 3)
CTTTTCAATTTGAAGAGAGTGCTTCCTCTGTTCTTAAGGCTAGGGAAC

CAAATTAGGTTGTTTCAATATCGTGCTAAAAGATACTGCCTTTAGAAG

AAGGCTATTGACAATCCAGCGTGTCTCGGTGGAACTCTGACTCCATGG

TTCACTTTCATGATGGCCACATGCCTCCTGCCCAGAGCCCGGCAGCCA

GTCCAGTGGGAAGGGGGCCGATACACTGTACGAGAGTGAGTAGCAGG

TCTCACAGTGAACCGGTCTCTTTCCCTACTGGACAGCTGCCTCGGGAA

GCCAAGTTGGGCTTTAAAGTGCAGGGCCTGCTGATGTTGAGTGCTTTT

TGTTGGCCTCTCTCCGTGTTCACAGCGGACCTTGATTTAAATGTCC

ATACAATTAAGGCACGCGGTGAATGCCAAGAATGGGGCTGGCATAAGA

AGTTATGTATTCATCCAATAATTCAAGCCAAGCAAGTATATAGGTGTT

TTAATAGTTTTTGTTTGCACTGACTCTCTTCGGTGACGGGTATTCTTG

GGTGGATAATACGGATTACGTTGTTATTGCTTAAGAATACGCGTAGTC

GAGGAGAGTACCAGTGCTATTTCCTTCAAATGAATGATTTTTACTAAT

TTTGTGTACTTTTATTGTGTCGATGTAGAATCTGCCTGGTCTATCTGA

TGTGACAGCTTCTGTAGTGGACCGGCTGGCCCCATCTGGAAGACTAGT

GATTTTGTTGTTGTCTTACTGCGCTCAACAACAAATCCCAGTCTACCT

AATGGTGCCAGCCATCGCTGCTAGCTGTAGAACTCCAGCTTCGGCCTG

TCGCCCAATCAAACTGTCCTGTTACTGAACACGTGATAATGTAGCGAG

ATTTTCTGTTGTGCTTGATCTAACCATGTGGTTGCGAGGTATGAGTAA

AACATGGTTCCGTCAAGCACCATGGAACGTCACGCAGCTTTCTACGTG

ACACTCCTAATGGAATGCCGTTATCCAAAGAGCAGCACGAACCCGACA

GGGCTGAGTGGCTTGTGCTAGGGAGAGGTTTGTGTCATTCCTGCTGAC

CAAACTGCAGGAAAAACTGCTAATTGTCATGCTGAAGACTGCCTGACG

GGGAGACTCTGCCTTCTGTAAGTAGGTCATGTAAAGAGCACGTGCTCC

TTGCTGCTGCGGCCGC

In some embodiments, the artificial microRNA cluster construct includes a miR-128 5' flanking sequence, a miR-128 hairpin, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 hairpin domain, a fifth miR-17-92 spacer sequence, a miR-34 hairpin domain, and a miR-128 3' flanking sequence and has the nucleic acid sequence of SEQ ID NO. 4 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 4.

(SEQ ID NO. 4)
CTTTTCAATTTGAAGAGAGTGCTTCCTCTGTTCTTAAGGGGCTAGGGA

ACCAAATTAGGTTGTTTCAATATCGTGCTAAAAGATACTGCCTTTAGA

AGAAGGCTATTGACAATCCAGCGTGTCTCGGTGGAACTCTGACTCCAT

GGTTCACTTTCATGATGGCCACATGCCTCCTGCCCAGAGCCCGGCAGC

CAGTCCAGTGGGAAGGGGGCCGATACACTGTACGAGAGTGAGTAGCA

GGTCTCACAGTGAACCGGTCTCTTTCCCTACTGGACAGCTGCCTCGGG

AAGCCAAGTTGGGCTTTAAAGTGCAGGGCCTGCTGATGTTGAGTGCTT

TTTGTTGGCCTCTCTCTCCGTGTTCACAGCGGACCTTGATTTAAATGT

CCATACAATTAAGGCACGCGGTGAATGCCAAGAATGGGGCTGGCATAA

GAAGTTATGTATTCATCCAATAATTCAAGCCAAGCAAGTATATAGGTG

TTTTAATAGTTTTTGTTTGCACTGACTCTCTTCGGTGACGGGTATTCT

TGGGTGGATAATACGGATTACGTTGTTATTGCTTAAGAATACGCGTAG

TCGAGGAGAGTACCAGTGCTATTTCCTTCAAATGAATGATTTTTACTA

ATTTTGTGTACTTTTATTGTGTCGATGTAGAATCTGCCTGGTCTATCT

GATGTGACAGCTTCTGTAGTGGACCGGCTGGCCCCATCTGGAAGACTA

GTGATTTTGTTGTTGTCTTACTGCGCTCAACAACAAATCCCAGTCTAC

CTAATGGTGCCAGCCATCGCTGCTAGCTGTAGAACTCCAGCTTCGGCC

TGTCGCCCAATCAAACTGTCCTGTTACTGAACACGTGATAATGTAGCG

AGATTTTCTGTTGTGCTTGATCTAACCATGTGGTTGCGAGGTATGAGT

AAAACATGGTTCCGTCAAGCACCATGGAACGTCACGCAGCTTTCTACG

TGAAAAGTCTGTAGAAAAGTAAGGGAAACTCAAACCCCTTTCGGCCAG

CGTGAGTGTTTCTTTGGCAGTGTCTTAGCTGGTTGTTGTGAGCAATAG

TAAGGAAGCAATCAGCAAGTATACTGCCCTAGAAGTGCTGCACGTTGT

GGGGCCCGAGACACTCCTAATGGAATGCCGTTATCCAAAGAGCAGCAC

GAACCCGACAGGGCTGAGTGGCTTGTGCTAGGGAGAGGTTTGTGTCAT

TCCTGCTGACCAAACTGCAGGAAAAACTGCTAATTGTCATGCTGAAGA

CTGCCTGACGGGGAGACTCTGCCTTCTGTAAGTAGGTCATGTAAAGAG

CACGTGCTCCTTGCTGCT

In some embodiments, the artificial microRNA cluster includes a miR-128 5' flanking sequence modified with a microRNA-21 (miR-21) sponge sequence, a miR-128 hairpin domain, a first miR-17-92 spacer sequence, a miR-124 hairpin domain, a second miR-17-92 spacer sequence, a miR-137 hairpin domain, a miR-128 3 flanking sequence and has the nucleic acid sequence of SEQ ID NO. 5 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 5.

(SEQ ID NO. 5)
CTTTTCAATTTGAAGAGAGTGCTTCCTCTGTTCTTAAGGCTAGGGAAC

CAAATTAGGTTGTTTCAATATCGTGGACGGCGCTAGGATCAACTCAAC

ATCAGTCAATGTGATAAGCTACAAGTATTCTGGTCACAGAATACAACT

CAACATCAGTCAATGTGATAAGCTACAAGATGATCCTAGCGCCGTCTT

GTCGGCAGTGGGAAGGGGGCCGATACACTGTACGAGAGTGAGTAGCA

GGTCTCACAGTGAACCGGTCTCTTTCCCTACTGCCGACAGCTGCCTCG

GGAAGCCAAGTTGGGCTTTAAAGTGCAGGGCCTGCTGATGTTGAGTGC

TTTTTGTTGGCCTCTCTCTCCGTGTTCACAGCGGACCTTGATTTAAAT

-continued

GTCCATACAATTAAGGCACGCGGTGAATGCCAAGAATGGGGCT<u>GGCAT</u>

AAGAAGTTATGTATTCATCCAATAATTCAAGCCAAGCAAGTATATAGG

TGTTTTAATAGTTTTTGTTTG<u>CA</u>CTGACTCTCTTCGGTGACGGGTATT

CTTGGGTGGATAATACGGATTACGTTGTTATTGCTTAAGAATACGCGT

AGTCGAGGAGAGTACCAGT<u>GC</u>ACACTCCTAATGGAATGCCGTTATCCA

AAGAGCAGCACGAACCCGACAGGGCTGAGTGGCTTGTGCTAGGGAGAG

GTTTGTGTCATTCCTGCTGACCAAACTGCAGGAAAAACTGCTAATTGT

CATGCTGAAGACTGCCTGACGGGGAGACTCTGCCTTCTGTAAGTAGGT

CATGTAAAGAGCACGTGCTCCTTGCTGCT

In some embodiments, the artificial microRNA cluster includes a miR-128 5' flanking sequence modified with a microRNA-21 (miR-21) sponge sequence, a miR-128 hairpin domain, a first miR-17-92 spacer sequence modified with a p50 aptamer sequence, a miR-124 hairpin domain, a second miR-17-92 spacer sequence, a miR-137 hairpin domain, a miR-128 3' flanking sequence and has the nucleic acid sequence of SEQ ID NO. 6 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 6.

(SEQ ID NO. 6)
CTTTTCAATTTGAAGAGAGTGCTTCCTCTGTTCTTAAGGCTAGGGAAC

CAAATTAGGTTGTTTCAATATCGTGGACGGCGCTAGGATCAACTCAAC

ATCAGTCAATGTGATAAGCTACAAGTATTCTGGTCACAGAATACAACT

CAACATCAGTCAATGTGATAAGCTACAAGATGATCCTAGCGCCGTCTT

<u>TCTTATGTCTCGGGATATCCCAGGGGGCCGATACACTGTACGAGAGT</u>

GAGTAGCAGGTCTCACAGTGAACCGGTCTCTTTCTGGGATATCCTCGA

GACATAAGAAACAAGATAGATCCTGAAACTGTTTTAAGGTTGGCCGAT

CTTCTGCTCGAGAATGCATGAAGCGTTCCATATTTTTCCGTGTTCAC

AGCGGACCTTGATTTAAATGTCCATACAATTAAGGCACGCGGTGAATG

CCAAGAAT<u>AATATGGAACGCTT</u>ATGTATTCATCCAATAATTCAAGCCA

AGCAAGTATATAGGTGTTTTAATAGTTTTTGTTTG<u>CA</u>CTGACTCTCTT

CCGTTATCCAAAGAGCAGCACGAACCCGACAGGGCTGAGTGGCTTGTG

CCGGTGACGGGTATTCTTGGGTGGATAATACGGATTACGTTGTTATTG

CTTAAGAATACGCGTAGTCGAGGAGAGTACCAGT<u>GC</u>ACACTCCTAATG

GAATGTAGGGAGAGGTTTGTGTCATTCCTGCTGACCAAACTGCAGGAA

AAACTGCTAATTGTCATGCTGAAGACTGCCTGACGGGGAGACTCTGCC

TTCTGTAAGTAGGTCATGTAAAGAGCACGTGCTCCTTGCTGCT

Underlined letters in SEQ ID NOs. 1-6 correspond to exemplary acceptor sites for microRNA hairpin domains included within the artificial microRNA cluster construct.

In some embodiments, the artificial microRNA or artificial microRNA cluster construct includes a polynucleotide encoding one or more microRNA hairpin domain having the nucleic acid sequence of any one of SEQ ID NO. 7-12 or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 7-12, as described below.

In some embodiments, the artificial microRNA or artificial microRNA cluster construct includes a polynucleotide encoding a miR-128 hairpin domain having the nucleic acid sequence of SEQ ID NO. 7, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 7.

(SEQ ID NO. 7)
CAGTGGGAAGGGGGCCGATACACTGTACGAGAGTGAGTAGCAGGTCT

CACAGTGAACCGGTCTCTTTCCCTACTG

In some embodiments, the artificial microRNA or artificial microRNA cluster construct includes a polynucleotide encoding a miR-124 hairpin domain having the nucleic acid sequence of SEQ ID NO. 8, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 8.

(SEQ ID NO. 8)
GGCCTCTCTCTCCGTGTTCACAGCGGACCTTGATTTAAATGTCCATAC

AATTAAGGCACGCGGTGAATGCCAAGAATGGGGCT

In some embodiments, the artificial microRNA or artificial microRNA cluster construct includes a polynucleotide encoding a miR-137 hairpin domain having the nucleic acid sequence of SEQ ID NO. 9, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 9.

(SEQ ID NO. 9)
CTGACTCTCTTCGGTGACGGGTATTCTTGGGTGGATAATACGGATTAC

GTTGTTATTGCTTAAGAATACGCGTAGTCGAGGAGAGTACCAG

In some embodiments, the artificial microRNA or artificial microRNA cluster construct includes a polynucleotide encoding a miR-7 hairpin domain having the nucleic acid sequence of SEQ ID NO. 10, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 10.

(SEQ ID NO. 10)
GTGGACCGGCTGGCCCCATCTGGAAGACTAGTGATTTTGTTGTTGTCT

TACTGCGCTCAACAACAAATCCCAGTCTACCTAATGGTGCCAGCCATC

GC

In some embodiments, the artificial microRNA or artificial microRNA cluster construct includes a polynucleotide encoding a miR-218 hairpin domain having the nucleic acid sequence of SEQ ID NO. 11, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 11.

(SEQ ID NO. 11)
GTGATAATGTAGCGAGATTTTCTGTTGTGCTTGATCTAACCATGTGGT

TGCGAGGTATGAGTAAAACATGGTTCCGTCAAGCACCATGGAACGTCA

CGCAGCTTTCTAC

In some embodiments, the artificial microRNA or artificial microRNA cluster construct includes a polynucleotide encoding a miR-34 hairpin domain having the nucleic acid sequence of SEQ ID NO. 12, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 12.

(SEQ ID NO. 12)
GGCCAGCGTGAGTGTTTCTTTGGCAGTGTCTTAGCTGGTTGTTGTGAG

CAATAGTAAGGAAGCAATCAGCAAGTATACTGCCCTAGAAGTGCTGCA

CGTTGTGGGGCCC

In some embodiments, the artificial microRNA or artificial microRNA cluster construct includes a polynucleotide encoding a non-coding RNA in the 5' flanking sequence having the nucleic acid sequence of SEQ ID NO. 13 or 14, or a variant thereof, such as polynucleotides encoding a nucleic acid sequence having at 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 13 or 14, as described below.

In some embodiments, the artificial microRNA or artificial microRNA cluster construct includes a polynucleotide encoding a miR-128 5' flanking sequence having the nucleic acid sequence of SEO ID NO. 13 or a variant thereof, such as polynucleotides encoding a nucleic acid sequence having at 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 13.

(SEQ ID NO. 13)
CTTTTCAATTTGAAGAGAGTGCTTCCTCTGTTCTTAAGGGGCTAGGGA

ACCAAATTAGGTTGTTTCAATATCGTGCTAAAAGATACTGCCTTTAGA

AGAAGGCTATTGACAATCCAGCGTGTCTCGGTGGAACTCTGACTCCAT

GGTTCACTTTCATGATGGCCACATGCCTCCTGCCCAGAGCCCGGCAGC

CA

In some embodiments, the artificial microRNA or artificial microRNA cluster construct includes a polynucleotide encoding a miR-128 5' flanking sequence modified with a miR-21 sponge sequence, having the nucleic acid sequence of SEQ ID NO. 14 or a variant thereof, such as polynucleotides encoding a nucleic acid sequence having at 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 14.

(SEQ ID NO. 14)
CTTTTCAATTTGAAGAGAGTGCTTCCTCTGTTCTTAAGGCTAGGGAAC

CAAATTAGGTTGTTTCAATATCGTGGACGGCGCTAGGATCAACTCAAC

ATCAGTCAATGTGATAAGCTACAAGTATTCTGGTCACAGAATACAACT

CAACATCAGTCAATGTGATAAGCTACAAGATGATCCTAGCGCCGTCTT

In some embodiments, the artificial microRNA or artificial microRNA cluster construct includes a polynucleotide encoding a non-coding RNA in the 3' flanking sequence having the nucleic acid sequence of SEQ ID NO. 15, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, as described below. In some embodiments, the artificial microRNA or artificial microRNA cluster construct includes a polynucleotide encoding a miR128 3' flanking sequence having the nucleic acid sequence of SEQ ID NO. 15, or a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15

(SEQ ID NO. 15)
ACACTCCTAATGGAATGCCGTTATCCAAAGAGCAGCACGAACCCGACA

GGGCTGAGTGGCTTGTGCTAGGGAGAGGTTTGTGTCATTCCTGCTGAC

CAAACTGCAGGAAAAACTGCTAATTGTCATGCTGAAGACTGCCTGACG

GGGAGACTCTGCCTTCTGTAAGTAGGTCATGTAAAGAGCACGTGCTCC

TTGCTGCT

In some embodiments, the artificial microRNA cluster construct includes a polynucleotide encoding a non-coding RNA in one or more spacer sequences, wherein the non-coding RNA has the nucleic acid sequence of any one of SEO ID NO. 16-21, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 16-21, as described below. In some embodiments, the artificial microRNA cluster construct includes a polynucleotide encoding a first miR-17-92 spacer sequence, wherein the first miR-17-92 spacer sequence has the nucleic acid sequence of SEQ ID NO. 16, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 16.

(SEQ ID NO. 16)
AGCTGCCTCGGGAAGCCAAGTTGGGCTTTAAAGTGCAGGGCCTGCTGA

TGTTGAGTGCTTTT

In some embodiments, the artificial microRNA cluster construct includes a polynucleotide encoding a second miR-17-92 spacer sequence, wherein the second miR-17-92 spacer sequence has the nucleic acid sequence of SEQ ID NO. 17, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 17.

(SEQ ID NO. 17)
TAAGAAGTTATGTATTCATCCAATAATTCAAGCCAAGCAAGTATATAG

GTGTTTTAATAGTTTTTGTTT

In some embodiments, the artificial microRNA cluster construct includes a polynucleotide encoding a third miR-17-92 spacer sequence, wherein the third miR-17-92 spacer sequence has the nucleic acid sequence of SEQ ID NO. 18, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 18.

(SEQ ID NO. 18)
TATTTCCTTCAAATGAATGATTTTTACTAATTTTGTGTACTTTTATTG

TGTCGATGTAGAATCTGCCTGGTCTATCTGATGTGACAGCTTCT

In some embodiments, the artificial microRNA cluster construct includes a polynucleotide encoding a fourth miR-17-92 spacer sequence, wherein the fourth miR-17-92 spacer sequence has the nucleic acid sequence of SEQ ID NO. 19, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 19.

(SEQ ID NO. 19)
TAGCTGTAGAACTCCAGCTTCGGCCTGTCGCCCAATCAAACTGTCCTG

TTACTGAA

In some embodiments, the artificial microRNA cluster construct includes a polynucleotide encoding a fifth miR-17-92 spacer sequence, wherein the fifth miR-17-92 spacer sequence has the nucleic acid sequence of SEQ ID NO. 20, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 20.

(SEQ ID NO. 20)
AAAAGTCTGTAGAAAAGTAAGGGAAACTCAAACCCCT

In some embodiments, the artificial microRNA cluster construct includes a polynucleotide encoding a first miR-17-92 spacer sequence modified with a p50 aptamer sequence, wherein the first miR-17-92 spacer sequence modified with a p50 aptamer sequence has the nucleic acid sequence of SEQ ID NO. 21, or is a variant thereof, such as polynucleotides encoding a nucleic acid sequence having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 21.

(SEQ ID NO. 21)
GGGATATCCTCGAGACATAAGAAACAAGATAGATCCTGAAACTGTTTT

AAGGTTGGCCGATCTTCTGCTCGAGAATGCATGAAGCGTTCCATATTT

TT

The artificial microRNA and microRNA cluster constructs described herein can be constructed by combining various elements (e.g. 5' flanking sequence, hairpin domain, spacer sequence, 3' flanking sequence, and any associated non-coding RNA sequences) in any combination, so long as the combination does not interfere with the processing of the microRNA cluster within a cell (e.g. a cell of a human subject) to produce mature and functional microRNAs. Provided below are non-limiting examples of the various combinations of elements that can be produced to create artificial microRNAs and microRNA clusters.

In some embodiments, the artificial microRNA construct includes a hairpin domain, such as a hairpin domain encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others, that is heterologous with respect to the artificial microRNA construct. In some embodiments, the hairpin domain is heterologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEO ID NO. 13 or SEQ ID NO. 14, among others. In some embodiments, the hairpin domain is heterologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the hairpin domain is homologous with respect to the artificial microRNA construct. In some embodiments, the hairpin domain is homologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 13 or SEQ ID NO. 14, among others. In some embodiments, the hairpin domain is homologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others.

In some embodiments, the artificial microRNA construct includes a 5' flanking sequence, such as a 5' flanking sequence encoded by any one of SEQ ID NO. 13 or SEQ ID NO. 14, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others, that is heterologous with respect to the artificial microRNA construct. In some embodiments, the 5' flanking sequence optionally includes a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes a microRNA sponge sequence. In some embodiments, the microRNA sponge sequence is antisense or partially antisense to a target microRNA sequence. In some embodiments, the target microRNA sequence is a miR-21 nucleotide sequence. In some embodiments, the non-coding RNA sequence encodes an aptamer. In some embodiments, the 5' flanking sequence is heterologous with respect to the hairpin domain of the artificial microRNA construct, such as a hairpin domain encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of anyone of SEQ ID NOs. 7-12, among others. In some embodiments, 5' flanking sequence is heterologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the 5' flanking sequence is homologous with respect to the artificial microRNA construct. In some embodiments, the 5' flanking sequence is homologous with respect to the hairpin domain of the artificial microRNA construct, such as a hairpin domain encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the 5' flanking sequence is homologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others.

In some embodiments, the artificial microRNA construct includes a 3' flanking sequence, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others, that is heterologous with respect to the artificial microRNA construct. In some embodiments, the 3' flanking sequence optionally includes a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes a microRNA sponge sequence. In some embodiments, the microRNA sponge sequence is antisense or partially antisense to a target microRNA sequence. In some embodiments, the target microRNA sequence is a miR-21 nucleotide sequence. In some embodiments, the non-coding RNA sequence encodes an aptamer. In some embodiments, the 3' flanking sequence is heterologous with respect to the hairpin domain of the artificial microRNA construct, such as a hairpin domain encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, 3' flanking sequence is heterologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the 3' flanking sequence is homologous with respect to the artificial microRNA construct. In some embodiments, the 3' flanking sequence is homologous with respect to the hairpin domain of the artificial microRNA construct, such as a hairpin domain encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the 3' flanking sequence is homologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others.

In some embodiments, the artificial microRNA cluster construct includes two or more hairpin domains, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others, that are heterologous with respect to the artificial microRNA cluster construct, such as an artificial microRNA cluster construct encoded by any one of SEQ ID NOs. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the two or more hairpin domains are heterologous with respect to the 5' flanking sequence of the artificial microRNA cluster construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the two or more hairpin domains are heterologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the two or more hairpin domains are heterologous with respect to one or more spacer sequences of the artificial microRNA cluster, such as one or more spacer sequences encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others. In some embodiments, the two or more hairpin domains are homologous with respect to the artificial microRNA cluster construct, such as an artificial microRNA cluster construct encoded by any one of SEQ ID NO. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the two or more hairpin domains are homologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the two or more hairpin domains are homologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the two or more hairpin domains are homologous with respect to one or more spacer sequences of the artificial microRNA cluster, such as one or more spacer sequence encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others.

In some embodiments, the artificial microRNA cluster construct includes a 5' flanking sequence, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others, that are heterologous with respect to the artificial microRNA cluster construct, such as an artificial microRNA cluster construct encoded by any one of SEQ ID NOs. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the 5' flanking sequence optionally includes a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes a microRNA sponge sequence. In some embodiments, the microRNA sponge sequence is antisense or partially antisense to a target microRNA sequence. In some embodiments, the target microRNA sequence is a miR-21 nucleotide sequence. In some embodiments, the non-coding RNA sequence encodes an aptamer. In some embodiments, the 5' flanking sequence is heterologous with respect to two or more hairpin domains of the artificial microRNA cluster construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the 5' flanking sequence is heterologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NOs. 15, among others. In some embodiments, the 5' flanking sequence is heterologous with respect to one or more spacer sequences of the artificial microRNA cluster, such as one or more spacer sequences encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others. In some embodiments, the 5' flanking sequence is homologous with respect to the artificial microRNA cluster construct, such as an artificial microRNA cluster construct encoded by any one of SEQ ID NO. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the 5' flanking sequence is homologous with respect to two or more hairpin domains of the artificial microRNA construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others, among others. In some embodiments, the 5' flanking sequence is homologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the 5' flanking sequence is homologous with respect to one or more spacer sequences of the artificial microRNA cluster, such as one or more spacer sequences encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others.

In some embodiments, the artificial microRNA cluster construct includes a 3' flanking sequence, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others, that are heterologous with respect to the artificial microRNA cluster construct, such as an artificial microRNA cluster construct encoded by any one of SEQ ID NOs. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the 3' flanking sequence optionally includes a non-coding RNA sequence.

In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments, the non-coding RNA sequence encodes a microRNA sponge sequence. In some embodiments, the microRNA sponge sequence is antisense or partially antisense to a target microRNA sequence. In some embodiments, the target microRNA sequence is a miR-21 nucleotide sequence. In some embodiments, the non-coding RNA sequence encodes an aptamer. In some embodiments, the 3' flanking sequence is heterologous with respect to two or more hairpin domains of the artificial microRNA cluster construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the 3' flanking sequence is heterologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the 3' flanking sequence is heterologous with respect to one or more spacer sequences of the artificial microRNA cluster, such as one or more spacer sequences encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others. In some embodiments, the 3' flanking sequence is homologous with respect to the artificial microRNA cluster construct, such as an artificial microRNA cluster construct encoded by any one of SEQ ID NO. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the 3' flanking sequence is homologous with respect to two or more hairpin domains of the artificial microRNA construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the 3' flanking sequence is homologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the 3' flanking sequence is homologous with respect to one or more spacer sequences of the artificial microRNA cluster, such as one or more spacer sequences encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others.

In some embodiments, the artificial microRNA cluster construct includes one or more spacer sequences, such as one or more spacer sequences encoded by any one of SEQ ID NOs. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others, that are heterologous with respect to the artificial microRNA cluster construct, such as an artificial microRNA cluster construct encoded by any one of SEQ ID NOs. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the spacer sequence optionally includes a non-coding RNA sequence. In some embodiments, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, microRNA sponges, and long non-coding RNAs. In some embodiments, the non-coding RNA sequence encodes an aptamer. In some embodiments, the aptamer binds to a p50 protein. In some embodiments, the one or more spacer sequences are heterologous with respect to two or more hairpin domains of the artificial microRNA cluster construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 7-12, among others. In some embodiments, the one or more spacer sequences are heterologous with respect to the 5' flanking sequence of the artificial microRNA construct, such as a 5' flanking sequence encoded by any one of SEQ ID NO. 13 or SEQ ID NO. 14 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the one or more spacer sequences are heterologous with respect to the 3' flanking sequence of the artificial microRNA construct, such as a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the one or more spacer sequences are heterologous with respect to one or more spacer sequences of the artificial microRNA cluster, such as a spacer sequence encoded by any one of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others. In some embodiments, the artificial microRNA cluster construct includes one or more spacer sequences, such as one or more spacer sequences encoded by any one of SEQ ID NOs. 16-21, among others, that are homologous with respect to the artificial microRNA cluster construct, such as an artificial microRNA cluster construct encoded by any one of SEQ ID NOs. 1-6 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 1-6, among others. In some embodiments, the one or more spacer sequences are homologous with respect to two or more hairpin domains of the artificial microRNA cluster construct, such as two or more hairpin domains encoded by any one of SEQ ID NOs. 7-12 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEO ID NOs. 7-12, among others. In some embodiments, the one or more spacer sequences are homologous with respect to the 5' flanking sequence of the artificial microRNA construct, such as a 5' flanking sequence encoded by any one of SEQ ID NO. 13 or SEQ ID NO. 14, or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NO. 13 or SEQ ID NO. 14, among others. In some embodiments, the one or more spacer sequences are homologous a 3' flanking sequence encoded by SEQ ID NO. 15 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of SEQ ID NO. 15, among others. In some embodiments, the one or more spacer sequences are homologous with respect to one or more spacer sequences of the artificial microRNA cluster, such as a spacer sequence encoded by anyone of SEQ ID NO. 16-21 or a variant thereof having at least 70% (e.g., at least 70%, 75%, 80%, 85%, 86%, 87%, 88%, 89%, 90%, 91%, 92%, 93%, 94%, 95%, 96%, 97%, 98%, 99% or more) sequence identity to the nucleic acid sequence of any one of SEQ ID NOs. 16-21, among others.

In any of the forgoing embodiments, the 5' flanking sequence, the 3' flanking sequence, or any of the one or more spacer sequences may be modified (e.g. replaced, inserted, concatenated) with a non-coding RNA sequence having a specified biological activity (e.g., microRNA sponge activity, aptamer activity, among others). In some embodiments of any of the foregoing aspects, the non-coding RNA sequence encodes any one of the following, including scaffolds for proteins, modifiers of pre-mRNA splicing, transfer-RNAs, ribosomal RNAs, Piwi-interacting-RNAs, small nucleolar RNAs, small nuclear RNAs, extracellular RNAs, small Cajal body-specific RNAs, and long non-coding RNAs. In some embodiments of any of the foregoing aspects, the non-coding RNA sequence encodes a microRNA sponge sequence. In some embodiments of any of the foregoing aspects, the microRNA sponge sequence is antisense or partially antisense to a target microRNA sequence. In some embodiments of any of the foregoing aspects, the target microRNA sequence is a miR-21 nucleotide sequence. In some embodiments of any of the foregoing aspects, the non-coding RNA sequence encodes an aptamer. In some embodiments, the aptamer binds to a p50 protein. As a non-limiting example, SEQ ID NO. 14 includes a modified 5' flanking sequence having a miR-21 sponge sequence. As yet another non-limiting example, SEQ ID NO. 21 includes a modified spacer sequence having a p50 aptamer sequence.

Percent (%) sequence identity can be calculated using routine methods known in the art.

Expression Vectors for Gene Delivery of Artificial microRNAs and microRNA Clusters In addition to achieving high rates of transcription, stable expression of an exogenous gene in a mammalian cell can be achieved by integration of the polynucleotide containing the gene into the nuclear genome of the mammalian cell. A variety of vectors for the delivery and integration of polynucleotides encoding exogenous genes into the nuclear DNA of a mammalian cell have been developed. Examples of expression vectors are known in the art. Expression vectors for use in the compositions and methods described herein contain a polynucleotide sequence that encodes an artificial microRNA or microRNA cluster composition, as well as, e.g., additional sequence elements used for the expression of these agents and/or the integration of these polynucleotide sequences into the genome of a mammalian cell. Certain vectors that can be used for the expression of compositions disclosed herein include plasmids that contain regulatory sequences, such as promoter and enhancer regions, which direct gene transcription. Other useful vectors for expression of the instant compositions contain polynucleotide sequences that enhance the rate of translation of these genes or improve the stability or nuclear export of the immature, unprocessed transcript. These sequence elements include, e.g., 5' and 3' untranslated regions, and polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker are genes that encode resistance to antibiotics, such as ampicillin, chloramphenicol, kanamycin, nourseothricin.

Viral Vectors for Expression of Artificial microRNA and/or microRNA Clusters

Viral genomes provide a rich source of vectors that can be used for the efficient delivery of exogenous genes into a mammalian cell. Viral genomes are particularly useful vectors for gene delivery as the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors are a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). In some embodiments, the expression vector is a Herpes Simplex virus. Other viruses include Norwalk virus, togavirus, flavivirus, reoviruses, papovavirus, hepadnavirus, human papilloma virus, human foamy virus, and hepatitis virus, for example. Examples of retroviruses are: avian leukosis-sarcoma, avian C-typo viruses, mammalian C-type, B-typo viruses, D-type viruses, oncoretroviruses, HTLV-BLV group, lentivirus, alpharetrovirus, gammaretrovirus, spumavirus. In some embodiments, the expression vector is a lentivirus. Other examples are murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses.

Retroviral Vectors

The delivery vector used in the methods and compositions described herein may be a retroviral vector. In some embodiments, the retroviral vector is a replicating retroviral vector. One type of retroviral vector that may be used in the methods and compositions described herein is a lentiviral vector. Lentiviral vectors (LVs), a subset of retroviruses, transduce a wide range of dividing and non-dividing cell types with high efficiency, conferring stable, long-term expression of the transgene.

The use of lentivirus-based gene transfer techniques relies on the in vitro production of recombinant lentiviral particles carrying a highly deleted viral genome in which the transgene of interest is accommodated. In particular, the recombinant lentivirus are recovered through the in trans coexpression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, incapsidation, and expression, in which the sequences to be expressed are inserted.

A lentiviral vector used in the methods and compositions described herein may include one or more of a 5'-Long terminal repeat (LTR), HIV signal sequence, HIV Psi signal 5'-splice site (SD), delta-GAG element, Rev Responsive Element (RRE), 3'-splice site (SA), elongation factor (EF) 1-alpha promoter and 3'-self inactivating LTR (SIN-LTR). The lentiviral vector optionally includes a central polypurine tract (cPPT) and a woodchuck hepatitis virus post-transcriptional regulatory element (WPRE. The lentiviral vector may further include a pHR' backbone, which may include for example as provided below.

A lentiviral vector used in the methods and compositions described herein may a 5-Long terminal repeat (LTR), HIV signal sequence, HIV Psi signal 5-splice site (SD), delta-GAG element, Rev Responsive Element (RRE), 3-splice site (SA), elongation factor (EF) 1-alpha promoter and 3-self inactivating LTR (SIN-LTR). It will be readily apparent to one skilled in the art that optionally one or more of these regions is substituted with another region performing a similar function.

Artificial microRNA or microRNA cluster compositions are required to be expressed at sufficiently high levels. Transgene expression can be driven by a promoter sequence. Optionally, the lentiviral vector includes a cytomegalovirus (CMV) promoter. The promoter may also be EF1 or bacteriophage T7 (T7) promoter. A person skilled in the art will be familiar with a number of promoters that will be suitable in the vector constructs described herein.

Enhancer elements can be used to increase expression of modified DNA molecules or increase the lentiviral integration efficiency. The lentiviral vector used in the methods and compositions described herein may include a nef sequence. The lentiviral vector used in the methods and compositions described herein may include a cPPT sequence which enhances vector integration. The cPPT acts as a second origin of the (+)-strand DNA synthesis and introduces a partial strand overlap in the middle of its native HIV genome. The introduction of the cPPT sequence in the transfer vector backbone strongly increased the nuclear transport and the total amount of genome integrated into the DNA of target coils. The lentiviral vector used in the methods and compositions described herein may include a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cells. The addition of the WPRE to lentiviral vector results in a substantial improvement in the level of transgene expression from several different promoters, both in vitro and in vivo. The lentiviral vector used in the methods and compositions described herein may include both a cPPT sequence and WPRE sequence.

The vector used in the methods and compositions described herein may, be a clinical grade vector.

AAV Vectors

The compositions and methods described herein may be incorporated into rAAV vectors and/or virions in order to facilitate their introduction into a cell. rAAV vectors useful in the compositions and methods described herein are recombinant nucleic acid constructs that include (1) a heterologous sequence to be expressed (e.g., a polynucleotide encoding an artificial microRNA or microRNA cluster) and (2) viral sequences that facilitate integration and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV wild-type genes deleted in whole or in part, but retain functional flanking ITR sequences. The AAV ITRs may be of any serotype suitable for a particular application.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2, and VP3, which are required for virion assembly.

rAAV virions useful in conjunction with the compositions and methods described herein include those derived from a variety of AAV serotypes including AAV 1, 2, 3, 4, 5, 6, 7, 8, 9, 10 and rh74. For targeting cells located in or delivered to the central nervous system, AAV2, AAV9, and AAV10 may be particularly useful. In some embodiments, the AAV vector is an AAV2 vector. In some embodiments, the AAV vector is an AAV9 vector.

Also useful in conjunction with the compositions and methods described herein are pseudotyped rAAV vectors. Pseudotyped vectors include AAV vectors of a given serotype pseudotyped with a capsid gene derived from a serotype other than the given serotype (e.g., AAV1, AAV2, AAV3, AAV4, AAV5, AAV6, AAV7, AAV8, AAV9, and AAV10, among others).

AAV virions that have mutations within the virion capsid may be used to infect particular cell types more effectively than non-mutated capsid virions. For example, suitable AAV mutants may have ligand insertion mutations for the facilitation of targeting AAV to specific cell types.

Viral Regulatory Elements

The viral regulatory elements are components of delivery vehicles used to introduce nucleic acid molecules into a host cell. The viral regulatory elements are optionally retroviral regulatory elements. For example, the viral regulatory elements may be the LTR and gag sequences from HSC1 or MSCV. The retroviral regulatory elements may be from lentiviruses or they may be heterologous sequences identified from other genomic regions.

One skilled in the art would also appreciate that as other viral regulatory elements are identified, these may be used with the nucleic acid molecules described herein.

Methods for the Delivery of Trangenes to Target Cells

Techniques that can be used to introduce a polynucleotide using, such as an artificial microRNA or microRNA cluster into a mammalian cell, using a targeted delivery system well known in the art. Examples of targeted delivery systems are provided in the examples below. For example, electroporation can be used to permeabilize mammalian cells (e.g., human target cells) by the application of an electrostatic potential to the cell of interest. Mammalian cells, such as human cells, subjected to an external electric field in this manner are subsequently predisposed to the uptake of exogenous nucleic acids. A similar technique, Nucleofection™, utilizes an applied electric field in order to stimulate the uptake of exogenous polynucleotides into the nucleus of a eukaryotic cell.

Additional techniques useful for the transfection of target cells are the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for example, by direct fusion of the liposome with the cell membrane or by endocytosis of the complex. Similar techniques that exploit ionic interactions with the cell membrane to provoke the uptake of foreign nucleic acids are contacting a cell with a cationic polymer-nucleic acid complex. Exemplary cationic molecules that associate with polynucleotides so as to impart a positive charge favorable for interaction with the cell membrane are activated dendrimers, polyethylenimine, and diethylaminoethyl (DEAE)-dextran. Magnetic beads are another tool that can be used to transfect target cells in a mild and efficient manner, as this methodology utilizes an applied magnetic field in order to direct the uptake of nucleic acids.

Another useful tool for inducing the uptake of exogenous nucleic acids by target cells is laserfection, also called optical transfection, a technique that involves exposing a cell to electromagnetic radiation of a particular wavelength in order to gently permeabilize the cells and allow polynucleotides to penetrate the cell membrane. The bioactivity of this technique is similar to, and in some cases found superior to, electroporation.

Impalefection Is another technique that can be used to deliver genetic material to target cells. It relies on the use of nanomaterials, such as carbon nanofibers, carbon nanotubes, and nanowires. Needle-like nanostructures are synthesized perpendicular to the surface of a substrate. DNA containing the gene, intended for intracellular delivery, is attached to the nanostructure surface. A chip with arrays of these needles is then pressed against cells or tissue. Cells that are impaled by nanostructures can express the delivered gene(s).

Magnetofection can also be used to deliver nucleic acids to target cells. The magnetofection principle is to associate nucleic acids with cationic magnetic nanoparticles. The magnetic nanoparticles are made of iron oxide, which is fully biodegradable, and coated with specific cationic proprietary molecules varying upon the applications. Their association with the gene vectors (DNA, siRNA, viral vector, etc.) is achieved by salt-induced colloidal aggregation and electrostatic interaction. The magnetic particles are then concentrated on the target cells by the influence of an external magnetic field generated by magnets.

Another useful tool for inducing the uptake of exogenous nucleic acids by target cells is sonoporation, a technique that involves the use of sound (typically ultrasonic frequencies) for modifying the permeability of the cell plasma membrane permeabilize the cells and allow polynucleotides to penetrate the cell membrane.

The compositions described herein may also be formulated for delivery in exogenous, small membrane vesicles (30 nm to 100 nm in diameter) of endocytic origin that are released into the extracellular environment following fusion of multivesicular bodies with the plasma membrane. Exosomes can be loaded with varied therapeutics such as small molecule drugs and nucleic acid molecules (e.g., inhibitory RNA molecules, such as siRNA, shRNA, or microRNA (e.g., such as artificial microRNA and/or microRNA clusters disclosed herein)) to form therapeutic exosomes, which constitute an attractive carrier and delivery system for therapeutics. Exosomes contain transmembrane- and membrane-anchored proteins that likely enhance endocytosis, thus promoting more efficient delivery of their internal content. Another advantage of therapeutic exosomes is enhanced stability and reduced clearance from circulation. The use of therapeutic exosomes as carrier and delivery system for therapeutics might also minimize cytotoxic effects observed with the use of synthetic nanoparticles (e.g., liposomes) in vivo. Exosomes can be isolated from supernatant of cells (e.g., fibroblast, fibroblast-like mesenchymal cells, mast cells, cancer cells, tumor cells, and/or cells from cancer tissue) by differential centrifugation processes. Following isolation, the exosomes (i.e., exosomes isolated from donor cells) can be modified so as to remove genetic materials (e.g., mRNA). Empty donor exosomes can be used for direct transfer to recipient cells or for direct transfection or microinjection of a therapeutic agent into the exosomes. Methods of transferring therapeutic agents directly into exosomes include transformation, transfection and microinjection.

The compositions described herein may also be formulated for delivery in virosomes, artificial targeted delivery systems for therapeutic agents consisting of a phospholipid mono- or bi-layer vesicle that incorporates viral surface glycoproteins to facilitate fusion with target cells. Virosomes are safe as a targeted delivery system for therapeutic agents (e.g., artificial microRNA and microRNA cluster compositions disclosed herein) as they lack the immunogenic properties of the virus from which they are derived, thereby precluding the possibility of mounting an immune response in the host. Virosomes containing the compositions described herein may be administered according to the methods known in the art.

Cell-to-Cell Diffusion of Transgenic microRNAs

An important facet of the present invention is that transgene delivery of artificial microRNA clusters to human glioblastoma cells resulted in intercellular diffusion of transgenic microRNAs to adjacent "Receiver" cells that were not transduced by the transgene. This finding was confirmed in vivo (see, e.g., Example 7) and in vitro (see, e.g., Example 8) and was shown not to require physical cell-to-cell contact, suggesting a microvesicle-mediated diffusion. Intercellular passage of microRNAs from transduced cells resulted in overexpression of microRNAs from the artificial cluster in receiver cells and profoundly reduced the clonogenic growth and proliferation of cancer cells. Thus, according to the present methods, artificial microRNA or microRNA cluster compositions described herein may be expressed in a target cell population within a subject, whereupon expression, the artificial microRNAs expressed individually or from a cluster along with any associated non-coding RNA sequences may be secreted in extracellular vesicles (e.g., microvesicles) and internalized by nearby cells (e.g., bystander cells), whereupon internalization the artificial microRNAs expressed individually or from a cluster may produce a therapeutic effect.

Methods of Treatment

Selection of Subjects

Subjects that may be treated as described herein are subjects having a disease (e.g., a cancer, such as GBM, leukemia, breast cancer, thyroid cancer). The type of disease may be a cancer, including but not limited to cancers such as GBM, leukemia, breast cancer, or thyroid cancer. In some embodiments, the cancer is GBM. In some embodiments, the cancer is leukemia. In some embodiments, the cancer is breast cancer. In some embodiments, the cancer is thyroid cancer. The compositions and methods described herein can be used to treat patients with normal expression levels of microRNAs and/or epigenetic regulator proteins, increased expression levels of microRNAs and/or epigenetic regulator protein, reduced expression levels of microRNAs and/or epigenetic regulator protein, and patients whose expression levels of microRNAs and/or epigenetic regulator proteins are unknown.

Routes of Administration

An effective amount a composition described herein for treatment of a disease (e.g., cancer, such as GBM, leukemia, breast cancer, or thyroid cancer) can be administered to a subject by standard methods. For example, the composition can be administered by any of a number of different routes including, e.g., systemic administration such as intravenous, intraperitoneal, intradermal, subcutaneous, percutaneous injection, oral, intranasal, transdermal (topical), or transmucosal. The composition can be administered orally or administered by injection, e.g., intramuscularly, intravenously, intraperitoneally, intrathecally, intracerebroventricularly, intraparenchymally, or intratumorally. In some embodiments, the composition is administered intratumorally. The most suitable route for administration in any given case will depend on the particular agent administered, the patient, the particular disease or condition being treated, pharmaceutical formulation methods, administration methods (e.g., administration time and administration route), the patient's age, body weight, sex, severity of the diseases being treated, the patient's diet, and the patient's excretion rate. The agent can be encapsulated or injected, e.g., in a viscous form, for delivery to a chosen site, e.g., a tumor site. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The compositions described herein can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the composition in the required amount in an appropriate solvent with one or a combination of ingredients enumerated above, as required, followed by filtered sterilization. Generally, dispersions are prepared by incorporating the composition into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

The compositions described herein can be administered directly (e.g., therapeutic microRNAs) or inserted into expression vectors used as gene therapy vectors. Gene therapy vectors can be delivered to a subject by, for example, intravenous injection, local administration, or by stereotactic injection. The pharmaceutical preparation of the gene therapy vector can include the gene therapy vector in an acceptable diluent, or can include a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration. Methods of formulating pharmaceutical agents are known in the art.

The compositions described herein can be administered locally, e.g., to the site of a cancer in a subject. Examples of local administration include epicutaneous, inhalational (e.g. by way of a nebulizer), intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect. As an example, for the treatment of a cancer described herein, the compositions described herein may be administered locally (e.g., intratumorally) in a compound-impregnated substrate such as a wafer, microcassette, or resorbable sponge placed in direct contact with the affected tissue. Alternatively, the composition is infused into the brain or cerebrospinal fluid using standard methods. A composition for use in the methods described herein can be administered at the site of a tumor, e.g., intratumorally. In certain embodiments, the agent is administered to a mucous membrane of the subject Cell-Mediated Delivery According to the methods described herein, a subject can be administered a pluripotent, multipotent cell (e.g., a mesenchymal stem cell, a cancer cell, among others), or differentiated cell that expresses a polynucleotide encoding any of the microRNA or microRNA cluster compositions described herein, including but not limited to any one of the polynucleotides encoding any of the nucleic acid sequences of SEQ ID NOS. 1-21, or a polynucleotide encoding a nucleic acid having at least 70% sequence identity (e.g., 70%, 75%, 80%, 85%, 90%, 95%, 96%, 97%, 98%, 99%, or more, sequence identity) to anyone of the nucleic acid sequences of SEQ ID NOS. 1-21.

Cells that may be used in conjunction with the compositions and methods described herein include cells that are capable of undergoing further differentiation. For example, one type of cell that can be used in conjunction with the compositions and methods described herein is a multipotent cell. A multipotent cell is a cell having the capacity to differentiate into a discrete subset of cell types. A non-limiting example of a multipotent cell includes mesenchymal stem cells (MSCs; also known as mesenchymal stromal cells). Mesenchymal stem cells have the capacity to differentiate into osteoblasts, chondrocytes, myocytes, and adipocytes, among other cell types. Other cells that may be used in conjunction with the compositions and methods described herein include cancer cells. In some embodiments, the cancer cells are GBM cancer cells. In some embodiments, the cancer cells are leukemia cancer cells. In some embodiments, the cancer cells are breast cancer cells. In some embodiments, the cancer cells are thyroid cancer cells.

MSCs and/or cancer cells can be obtained from the subject (e.g. a human subject) by, for example, obtaining MSCs and/or cancer cells from the body or an organ of the body containing MSCs and/or cancer cells. Such sources include unfractionated bone marrow, umbilical cord, placenta, amniotic fluid, brain, breasts, thyroid, and/or teeth. Once obtained from the subject, MSCs and/or can be enriched for cells having specific genetic or protein markers of interest using methods well-known in the art. For example, the more mature, differentiated cells can be selected against based on cell surface molecules they express. Cells that may be used in conjunction with the compositions and methods described herein include autologous cells. Cells described herein may also differentiate into a variety of cell types as described above. Differentiation may occur ex vivo or in vivo. As described herein, cell-mediated delivery of artificial microRNA or microRNA cluster compositions can be performed in combination with administration of one or more additional therapeutic agents or therapeutic modalities. The MSCs, among other multipotent cells, and/or cancer cells may be genetically modified to express the artificial microRNA or microRNA cluster compositions described herein by contacting the cells with an expression vector (e.g., via transfection or transduction) containing a nucleotide encoding the artificial microRNA or microRNA cluster compositions using any of the methods described herein. Other methods for introducing compositions described herein into cell of interest may be employed.

In some embodiments, the cells contacted with an expression vector encoding a microRNA or microRNA cluster, as described herein, express (e.g. transcribe) the microRNA or microRNA cluster encoded within the vector. In some embodiments, the cells are introduced into a subject (e.g. a human subject) having a disease (e.g., cancer, such as GBM, leukemia, breast cancer, or thyroid cancer, among others). In some embodiments, the cells express the artificial microRNAs or microRNA clusters contained therein within the subject. In some embodiments, the expressed artificial microRNAs (individually or as a cluster) are packaged into microvesicles (e.g. exosomes, extracellular vesicles) within the cells and the microvesicles secreted into the extracellular space within the subject. In some embodiments, the secreted microvesicles can be internalized by surrounding cells (e.g., surrounding cancer cells) within the subject. In some embodiments, the internalized microvesicles can release the packaged microRNA into the cytoplasm of the surrounding cells, whereupon they may exert a biological activity (e.g. any activity associated with microRNAs or associated non-coding regions, as described herein). In some embodiments, the biological activity results in a therapeutic effect in the subject.

Dosing

Subjects that can be treated as described herein are subjects with having or a disease (e.g., a cancer, such as GBM, leukemia, breast cancer, thyroid cancer). The cancer may be a primary tumor or a metastasized tumor. In some embodiments, the cancer is GBM. In some embodiments, the cancer is leukemia. In some embodiments, the cancer is breast cancer. In some embodiments, the cancer is thyroid cancer. Subjects who can be treated with the methods disclosed herein include subjects who have had one or more tumors resected, received chemotherapy or other pharmacological treatment for the cancer, received radiation therapy, and/or received other therapy for the cancer. Subjects who have never previously been treated for cancer can also be treated using the methods and compositions described herein.

In some embodiments, the agent (e.g. an expression vector encoding any of the microRNA or microRNA cluster compositions described herein, or a genetically modified cell, such as a mesenchymal stem cell or a cancer cell transfected or transduced with the expression vector) is administered in an amount and for a time effective to result in one of (or more, e.g., 2 or more, 3 or more, 4 or more of): (a) reduced tumor size, (b) reduced rate of tumor growth, (c) increased tumor cell death (d) reduced tumor progression, (e) reduced number of metastases, (f) reduced rate of metastasis, (g) reduced tumor migration, (h) reduced tumor invasion, (i) reduced tumor volume, (j) decreased tumor recurrence, (k) increased survival of subject, (l) increased progression free survival of subject.

The methods described herein may include a step of selecting a treatment for a patient. The method includes (a) identifying (e.g., diagnosing) a patient who has a disease (e.g., a cancer, such as GBM, leukemia, breast cancer, thyroid cancer), and (b) selecting an artificial microRNA or microRNA cluster composition, e.g., compositions described herein, to treat the condition in the patient. In some embodiments, the method includes administering the selected treatment to the subject. In some embodiments, a patient is Identified as having cancer based on imaging (e.g., MRI, CT, or PET scan), biopsy, or blood sample (e.g., detection of blood antigen markers, circulating tumor DNA (e.g., by PCR). In some embodiments, a patient is identified as having cancer after presenting with one or more symptoms of a paraneoplastic syndrome (e.g., fever, auto-antibodies directed against nervous system proteins, ataxia, dizziness, nystagmus, difficulty swallowing, loss of muscle tone, loss of fine motor coordination, slurred speech memory loss, vision loss, sleep disturbances, dementia, seizures, dysgeusia, cachexia, anemia, itching, or sensory loss in the limbs). In some embodiments, a patient presents with symptoms of paraneoplastic syndrome and is then identified as having cancer based on imaging (e.g., CT, MRI, or PET scans).

In one embodiment, the method includes (a) identifying (e.g., diagnosing) a patient who has a neoplasm, (b) optionally evaluating the subject for metastasis to brain or spinal cord, and (c) selecting an artificial microRNA or microRNA cluster composition (e.g., compositions disclosed herein), to treat the patient if the neoplasm exhibits metastasis to brain or spinal cord. In some embodiments, the neoplasm is GBM. In some embodiments the neoplasm is lung cancer (e.g., small cell lung cancer, non-small cell lung cancer), breast cancer, thyroid cancer, leukemia ovarian cancer, skin cancer (e.g., melanoma), lymphoma, renal cell carcinoma, GI tract cancer (e.g., gastric cancer), head and neck cancer, uterine cancer, ovarian cancer, testicular cancer, thymoma, kidney cancer, diffuse large B-cell lymphoma, hepatocellular carcinoma, prostate cancer, pancreatic cancer, colorectal cancer.

In one embodiment, the method includes (a) identifying (e.g., diagnosing) a patient who has cancer, (b) optionally evaluating the subject (e.g., human patient) expression of endogenous microRNAs, and (c) selecting an artificial microRNA or microRNA cluster composition (e.g., compositions disclosed herein) to treat the patient if the cancer exhibits downregulation of specific single or multiple microRNAs. In some embodiments, the neoplasm is a brain cancer (e.g., GBM), thyroid cancer, leukemia, lung cancer (e.g., small cell lung cancer, non-small cell lung cancer), breast cancer, skin cancer (e.g., melanoma), lymphoma, renal cell carcinoma, GI tract cancer, prostate cancer, pancreatic cancer, ovarian cancer, uterine cancer, head and neck cancer, esophageal cancer, mesothelioma or colorectal cancer. MicroRNA expression can be measured in a cancer sample collected from a subject using standard techniques known in the art, such as quantitative RT-PCR, RNA sequencing, fluorescent in situ hybridization, cDNA microarray, and droplet digital PCR. A cancer sample can be evaluated for increased expression of single or multiple microRNA by comparison to a reference sample (e.g., a non-cancerous cell of the same typo).

In some embodiments, the method includes administering the selected treatment to the subject.

The method may also include a step of assessing the subject for a parameter of cancer progression or remission, e.g., assessing the subject for one or more (e.g., 2 or more, 3 or more, 4 or more) of: primary tumor size (e.g., by imaging), number of metastases (e.g., by imaging or biopsy), cell death in situ (e.g., by biopsy), blood antigen markers (e.g., by ELISA), circulating tumor DNA (e.g., by PCR), or function of the affected organ (e.g., by a test of circulating enzymes for liver, albuminuria for kidney, lung capacity for lung, etc.).

In certain embodiments, an artificial microRNA or microRNA cluster composition administered according to the methods described herein does not have a direct effect on the gut. Any effect on the gut is reduced compared to the effect observed if the composition is administered directly to the gut. In some embodiments, direct effects on the gut are avoided by administering the agent locally to a subject.

Subjects with cancer are treated with an effective amount of an artificial microRNA or microRNA cluster composition described herein. The methods described herein also include contacting a tumor or cancer cell with an effective amount of the composition. In some embodiments, an effective amount of an artificial microRNA or microRNA cluster composition is an amount sufficient to treat the cancer or tumor, cause remission, reduce tumor growth, reduce tumor volume, reduce tumor metastasis, reduce tumor invasion, reduce tumor proliferation, reduce tumor migration, or reduce tumor number, increase tumor microRNA expression, increase cancer cell death, increase cancer cell autophagy increase time to recurrence, or improve survival.

The compositions described herein are administered in an amount (e.g., an effective amount) and for a time sufficient to effect one of the outcomes described above. The composition may be administered once or more than once. The composition may be administered once daily, twice daily, three times daily, once every two days, once weekly, twice weekly, three times weekly, once biweekly, once monthly, once bimonthly, twice a year, or once yearly. Treatment may be discrete (e.g., an injection) or continuous (e.g., treatment via an implant or infusion pump). Subjects may be evaluated for treatment efficacy 1 week, 2 weeks, 1 month, 2 months, 3 months, 4 months, 5 months, 6 months or more following administration of an artificial microRNA or microRNA cluster composition depending on the composition and route of administration used for treatment. Depending on the outcome of the evaluation, treatment may be continued or ceased, treatment frequency or dosage may change, or the patient may be treated with a different composition. Subjects may be treated for a discrete period of time (e.g., 1, 2, 3, 4, 5, 6, 7, 8, 9, 10, 11, or 12 months) or until the disease or condition is alleviated, or treatment may be chronic depending on the severity and nature of the disease or condition being treated.

Combination Therapy

The compositions described herein can be administered in combination with a second therapeutic agent for treatment of a disease (e.g., a cancer, such as glioblastoma multiforme, leukemia, breast cancer, thyroid cancer). In some embodiments, the second therapeutic agent is selected based on tumor type, tumor tissue of origin, tumor stage, or mutations in genes expressed by the tumor.

Chemotherapy

One type of therapeutic agent that can be administered in combination with the compositions of the present invention described herein is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as temozolomide, thlotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues. KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norieucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, opitiostanol, mopitiostano, testolactone; anti-adronals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraenne; pontostatin; phonamot; pirarubicin; losoxantrone; podophyllinic acid; 2-ethyihydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel; chloranbucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. In some embodiments, the chemotherapeutic agent is temozolomide. In some embodiments, the chemotherapeutic is an immunomodulatory agent. Two or more chemotherapeutic agents can be used in a cocktail to be administered in combination with the compositions described herein. Suitable dosing regimens of combination chemotherapies are known in the art.

Non-Drug Therapies

Another type of therapeutic modality that can be administered in combination with the compositions disclosed herein is a therapeutic modality that is a non-drug treatment. For example, the second therapeutic agent is radiation therapy, immunotherapy (e.g. an immunomodulatory agent), cryotherapy, alternating electric field therapy, hyperthermia and/or surgical excision of tumor tissue Biologic Cancer Agents Yet another type of agent that can be administered in combination with the compositions disclosed herein is a therapeutic agent that is a biologic such as a cytokine (e.g., interferon or an interleukin (e.g., IL-2 or IL-12)) used in cancer treatment. In other embodiments the biologic is an anti-angiogenic agent, such as an anti-VEGF agent, e.g., bevacizumab. In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. In some embodiments, the biologic is an immunomodulatory agent. In some embodiments, the biologic cancer agent is an immunomodulatory agent.

Checkpoint Inhibitors

One type of agent that can be also administered in combination with the compositions described herein is a checkpoint inhibitor.

CAR-T Therapy

Another therapy that can be employed in combination with the methods and compositions described herein is chimeric antigen receptor (CAR)-T therapy, or therapy with lymphocytes, such as autologous or allogeneic T cells, that have been modified to express a CAR that recognizes specific cancer antigens.

Oncolytic Viruses

Another type of therapeutic agent that can be administered in combination with a composition described herein is an oncolytic virus.

Kits

The compositions described herein can be provided in a kit for use in treating a disease (e.g., cancer, such as glioblastoma multiforme (GBM), leukemia, breast cancer, or thyroid cancer, among others). Compositions may include expression vectors described herein (e.g., retroviral vector, such as a lentivirus, a replicating retrovirus, or an adeno-associated viral (AAV) vector that express compositions including artificial microRNA constructs (e.g., artificial microRNAs or microRNA clusters). The kit can include a package insert that instructs a user of the kit, such as a physician, to perform the methods described herein. The kit may optionally include a syringe or other device for administering the composition.

EXAMPLES

The following are various exemplary compositions and methods which describe the invention. It is understood that other embodiments may be practiced given the general description provided above.

Example 1. Engineering microRNA Clusters in Silico

Figure 1B:
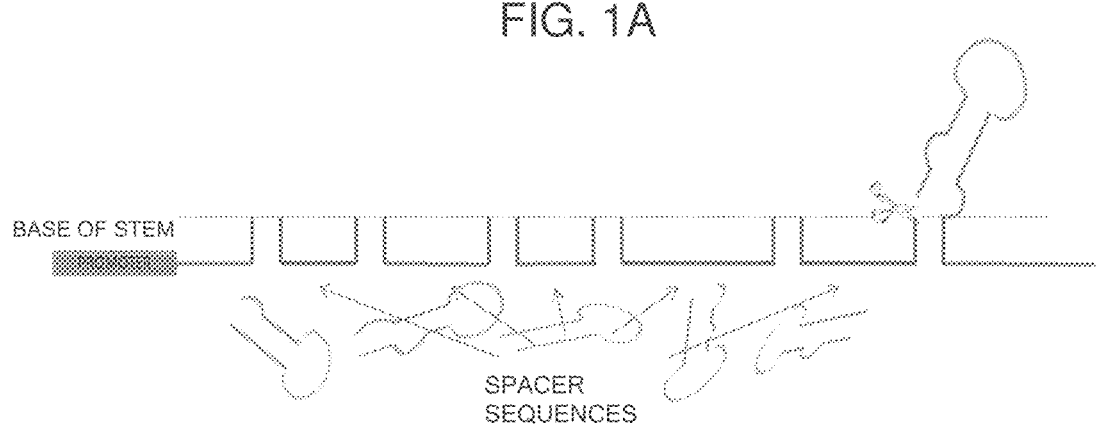
Figure 1C:
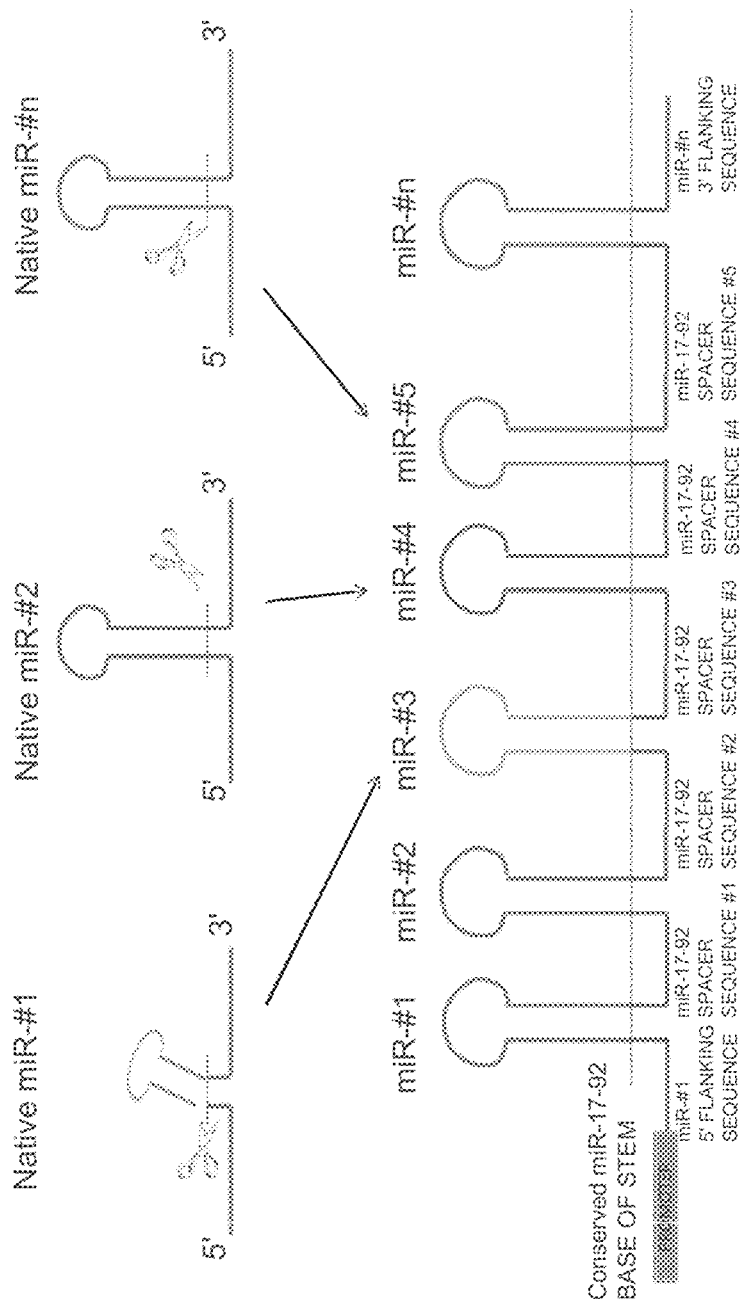
Figure 1D:
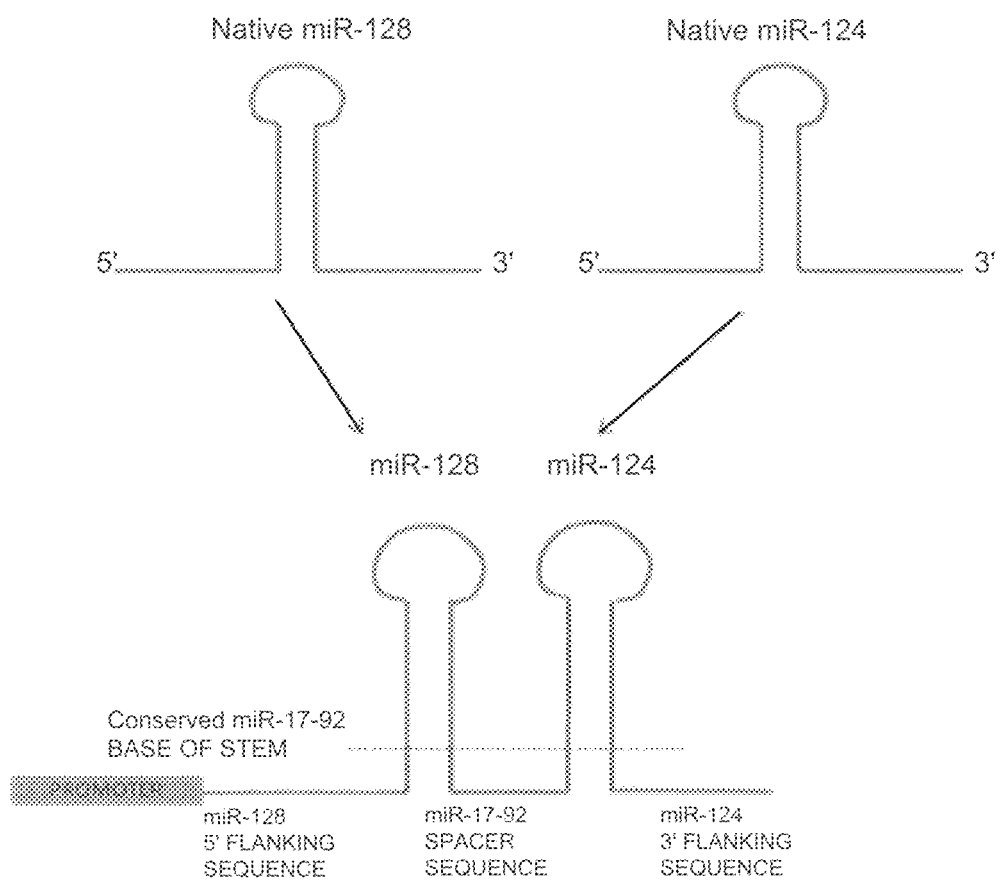
Figure 1E:
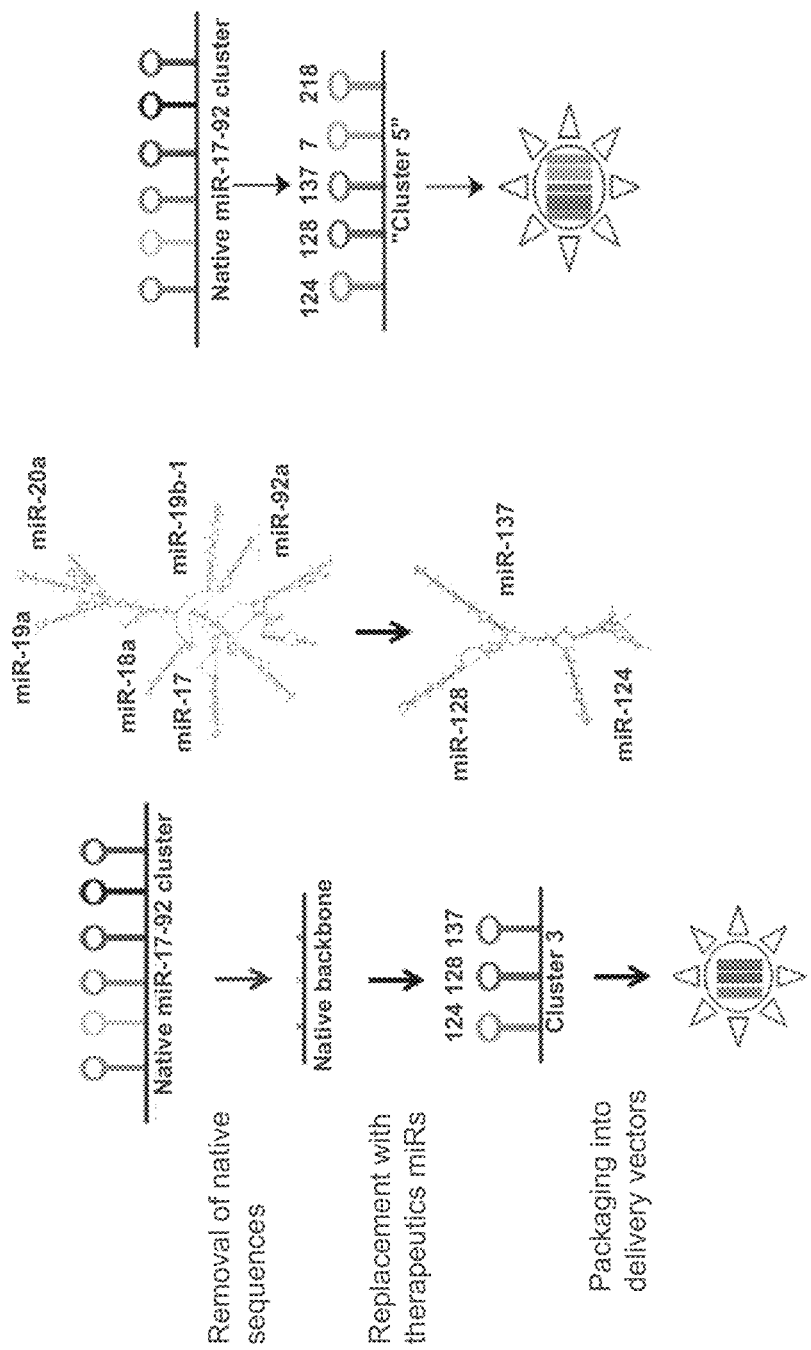

DNA structures of pre-existing, naturally occurring microRNA clusters can be used as a backbone (e.g. a scaffold) to engineer virtually any microRNA cluster, while the native microRNA hairpin sequences can be replaced with other microRNA hairpins of choice. Accordingly, a microRNA cluster can be divided into functional parts (the hairpins) and structural parts (the "spacer sequences", "base of stem" sequences and "flanking sequences") (FIG. 1A). The structural parts may also be modified to become functional parts by substituting, inserting, or concatenating non-coding RNA sequences having a specified biological activity (e.g. microRNA sponge activity, aptamer activity, among others) into the structural parts. Since microRNA expression does not require an open reading frame (unlike protein coding genes) manipulation of these DNA sequences is routinely facilitated. Typically, step 1 consists of removing a DNA sequence encoding an appropriate native microRNA hairpin contained in a microRNA cluster, with the exception of typically 3-21 nucleotides at both the 5' and 3' end of each hairpin stem. These nucleotides are left to create a suitable "acceptor site" (thereafter called "base of stem" sequences) for the insertion of a non-native microRNA, as these nucleotides will reconstitute the base of the engineered microRNA stem, a structure that is essential for correct processing of any microRNAs (FIG. 1B). Next, in step 2, the sequences of the microRNA hairpins of interest are "attached" to the base of stem sequences. Hero the native spacer sequences from the miR-17-92 cluster are used to separate multiple inserted microRNA hairpins, thus retaining the original configuration of the miR-17-92 microRNA cluster (FIG. 1C). FIG. 1D shows a further example of an artificial microRNA cluster constructed containing two heterologous microRNA hairpins (miR-128 and miR-124; termed "Cluster 2") inserted into the backbone of a naturally occurring miR-17-92 cluster. Other non-limiting examples of artificial microRNA cluster constructs are illustrated in FIG. 1E, in which the genetic backbone of the miR-17-92 cluster was used for the construction of an artificial microRNA cluster containing three heterologous microRNA hairpin domains (e.g., miR-124, miR-128, and miR-137; termed "Cluster 3") as well as an artificial cluster containing five heterologous microRNA hairpin domains (e.g., miR-124, miR-128, and miR-137, miR-7, and miR-218; termed "Cluster 5"). These artificial microRNA clusters are suitable for packaging into expression vectors for virtually any therapeutic application (e.g., treatment of cancer, such as glioblastoma multiforme (GBM), leukemia, breast cancer, or thyroid cancer, among others)

Importantly, the engineering is performed "in silico" by creating appropriate DNA sequences according to the principles outlined above. Advantageously, enzymatic restriction digestions or ligations are not typically required since artificial DNA sequences, once contemplated, can be directly generated in their entirety according to standard DNA sequencing methodologies (e.g. Sanger sequencing).

Figure 2A:
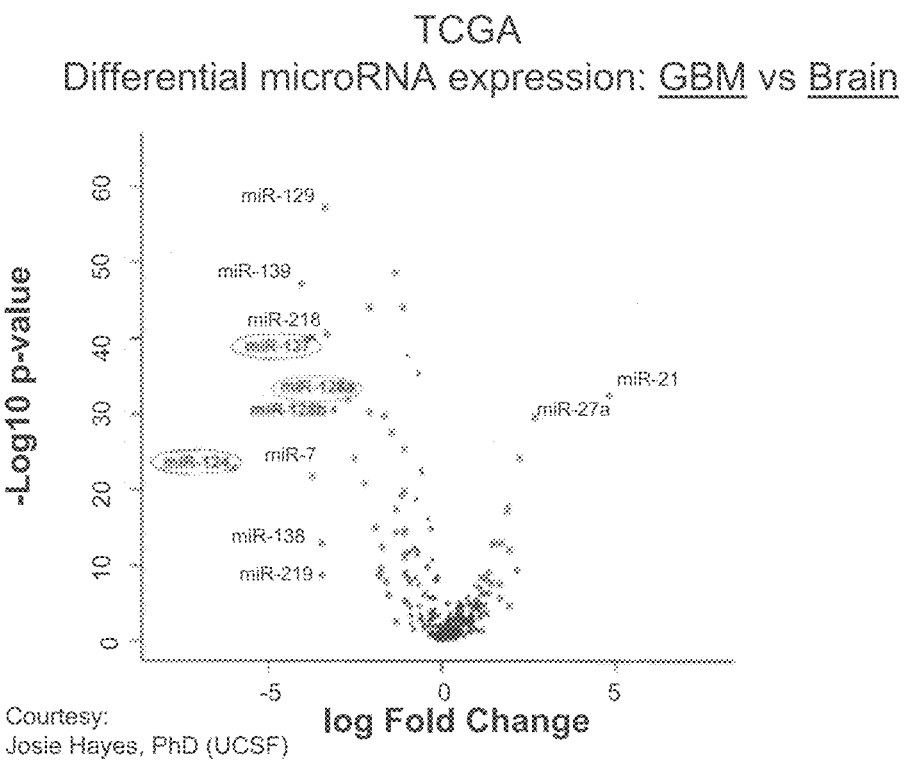
FIGS. 2A-2F shows a series of figures demonstrating clustered changes in microRNA expression in glioblastoma multiforme (GBM) during cellular differentiation, and changes in expression of target genes of the noted microRNAs.
Figure 2B:
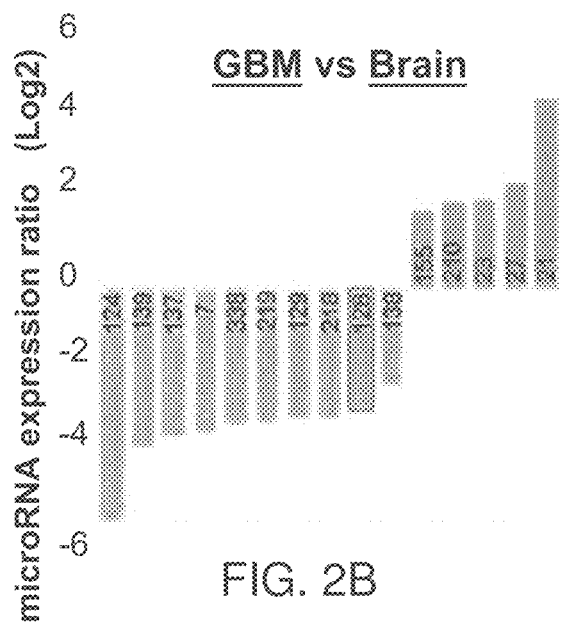

Example 2. MIR-128 Belongs to a Group of microRNAs, all Lost in GBM, which Function Together by Targeting Multiple Epigenetic Proteins MicroRNA expression analysis from The Cancer Genome Atlas (TCGA) database revealed that there is a signature of 10 microRNAs consistently downregulated (cut off>4 fold) in all GBM patient samples which were analyzed (n=520; FIG. 2A-B). To verify the possibility of a functional link among any of these microRNAs, human neural progenitor cells (NPCs) were induced to differentiate into either neurons or astrocytes by selective growth in defined media (epidermal growth factor/fibroblast growth factor) for neurosphores, retinoic acid for neuronal differentiation, and fetal bovine serum for astrocytic differentiation, and the differential expression of the 10 microRNAs was assessed.

Figure 2C:
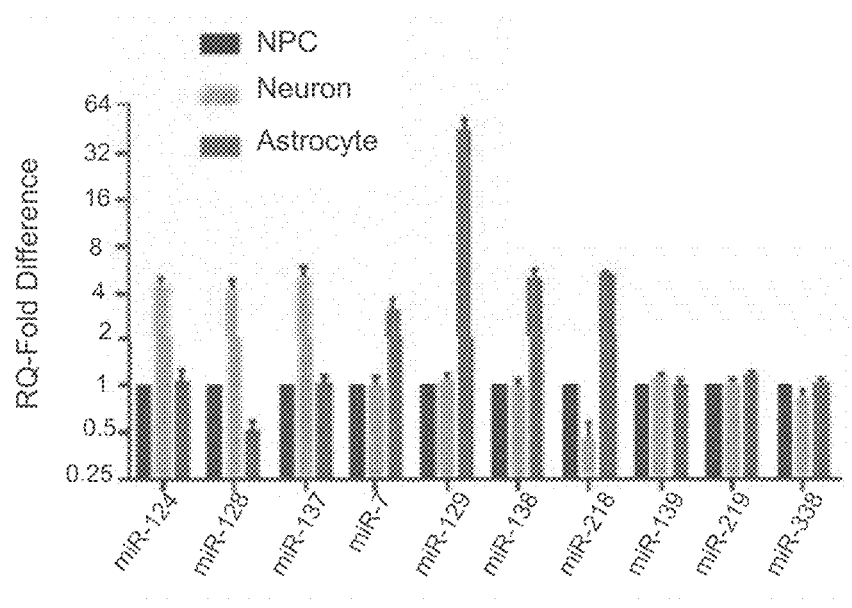
Figure 2D:
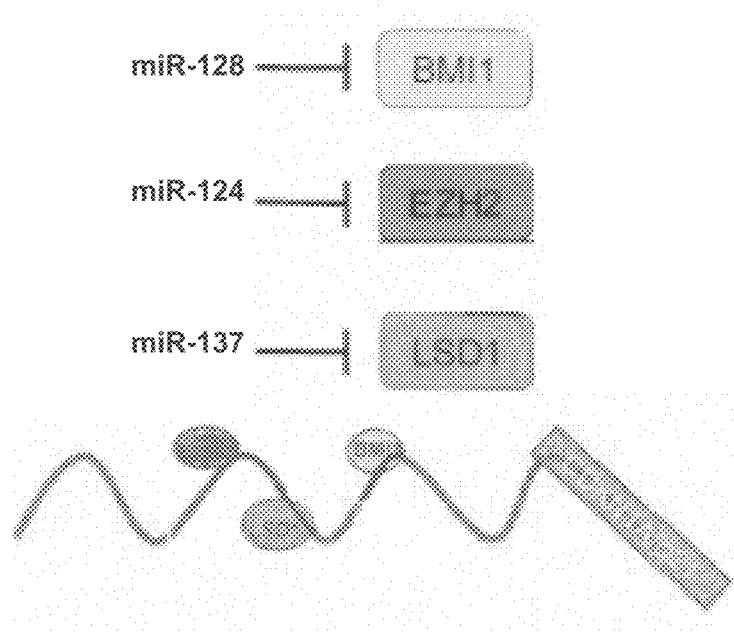

Among the 10 genes, miR-128, miR-124 and miR-137 displayed a similar pattern of induction upon neuronal differentiation, suggesting that they could function together towards a broader regulation of the neuronal specification (FIG. 2C). Similarly, other microRNAs were uniquely induced during astrocytic differentiation, strongly suggesting that specific clusters of microRNAs were differentially activated during different cellular conditions. It is known that miR-128 controls BMI1 proto-oncogene polycomb ring finger (BMI1), and reports from the literature linked miR-124 with enhancer of zeste 2 polycomb repressive complex 2 subunit (EZH2), another fundamental epigenetic protein ubiquitous in GBM, and miR-137 with lysine demethylase 1a (LSD1), a histone demethylase fundamental for the maintenance of glioblastoma cell stemness (FIG. 2D).

Figure 2E:
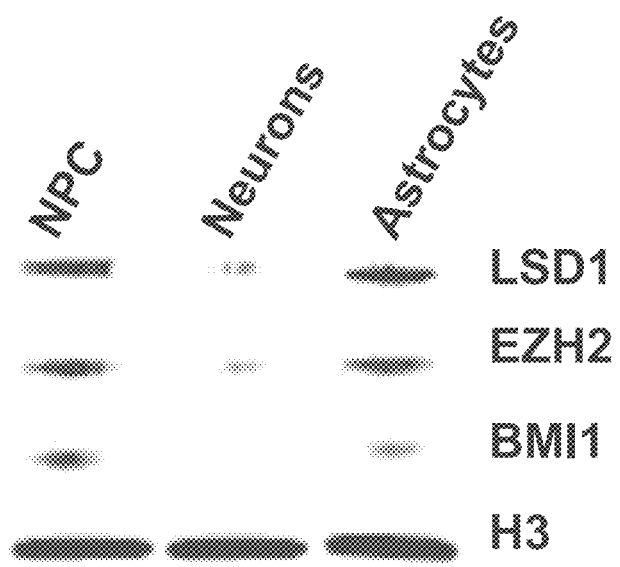
Figure 2F:
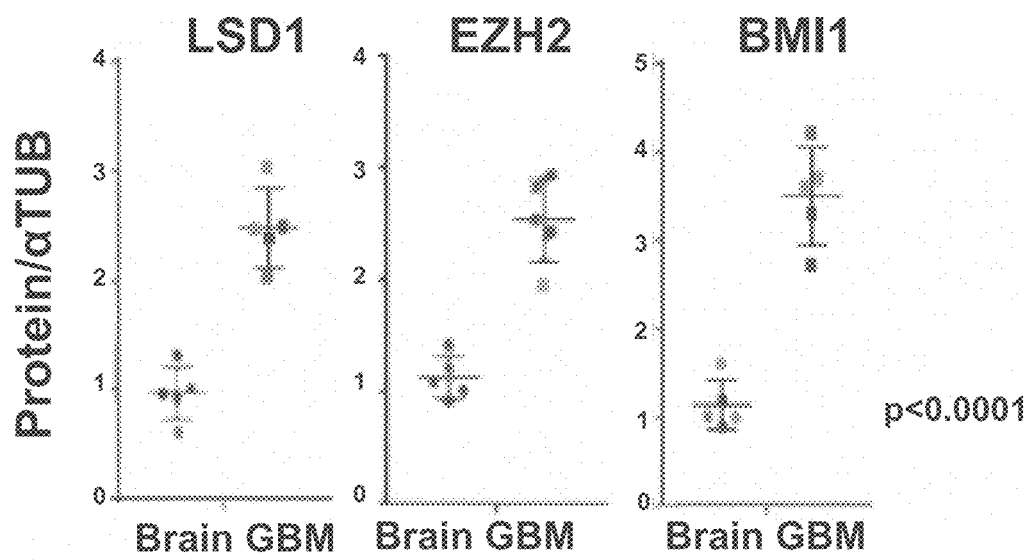

As shown in FIG. 2E, these three epigenetic regulator proteins are downregulated upon induction of neuronal differentiation, thus correlating inversely with the expression of the three microRNAs. The analysis of three consecutive GBM surgical specimens confirmed that this strong inverse correlation between the three microRNA and the three target proteins is maintained in vivo (FIG. 2F).

Example 3. Functionality of an Artificial miR-128-124 Cluster

As a proof of principle for engineering artificial microRNA clusters, miR-128 and miR-124, two microRNAs that are expressed in neurons and are downregulated in GBM and other cancers, were chosen to generate an artificial microRNA cluster. The sequence encoding the first two microRNAs of the miR-17-92 cluster (miR-17 and miR-18a) was used as a scaffold. The stem and hairpins of miR-17 and miR-18a were removed, while the two corresponding base of stem sequences were maintained and used as an anchor for miR-128 and miR-124 hairpins. The two microRNAs were separated by the native miR-17-92 cluster spacer sequence #1 (e.g., SEQ ID NO. 17), in order to retain the original configuration of the cluster. In order to limit the use of DNA sequences from miR-17-92, a microRNA cluster that is oncogenic, the flanking sequences at the 5' and 3' ends, also useful for microRNA processing, were taken from miR-128 and miR-124, respectively. The final sequence encoding the artificial miR-128-124 cluster generated a 560 bp sequence (SEQ ID NO. 1). General methods for preparing such a microRNA cluster are described in Example 1.

Figure 3A:
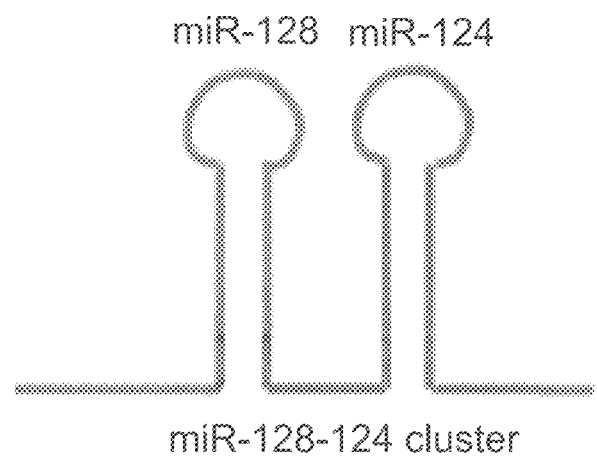
FIGS. 3A-3E illustrates functionality of artificial miR-128-124 cluster.
Figure 3B:
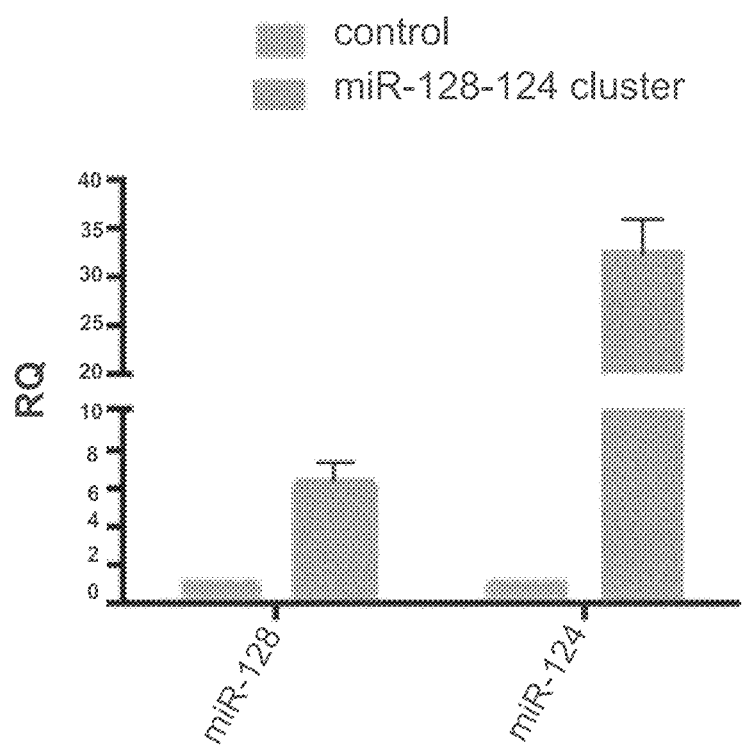

This artificial miR-128-124 cluster was cloned into a green fluorescent protein (GFP)-expressing lentiviral vector, and transduced into GBM cells. Real time qPCR obtained after creation of stable cell lines showed that cells infected with the artificial miR-128-124 cluster expressed both miR-124 and miR-128, confirming that each microRNA is correctly processed into the two mature microRNAs, recapitulating the function of a native microRNA cluster (FIG. 3A-2B).

Figure 3C:
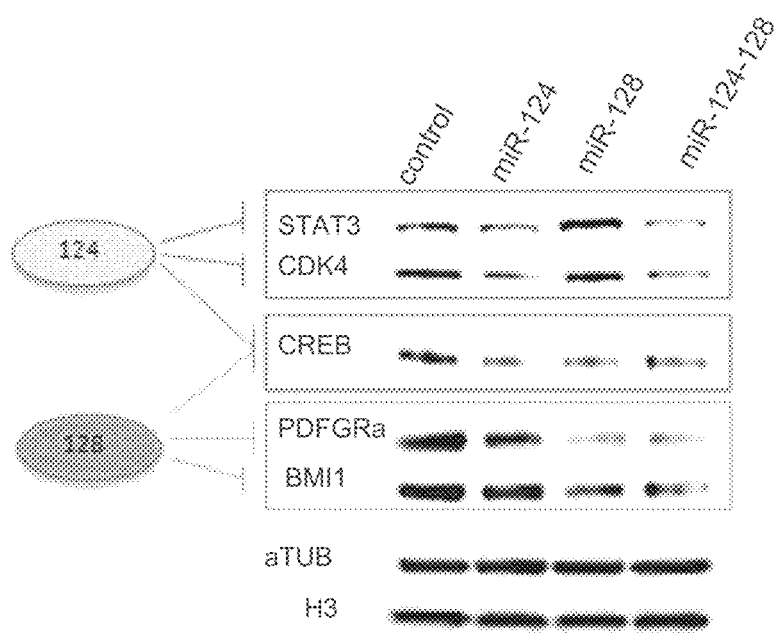
Figure 3D:
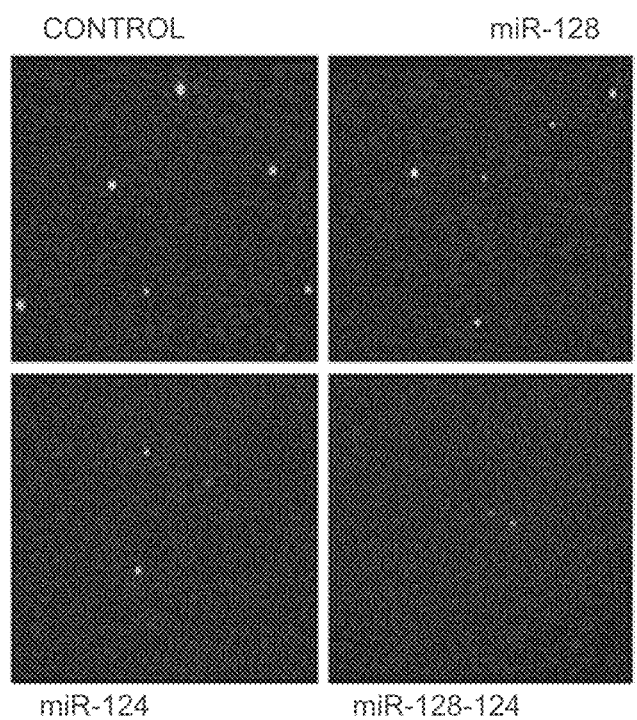
Figure 3E:
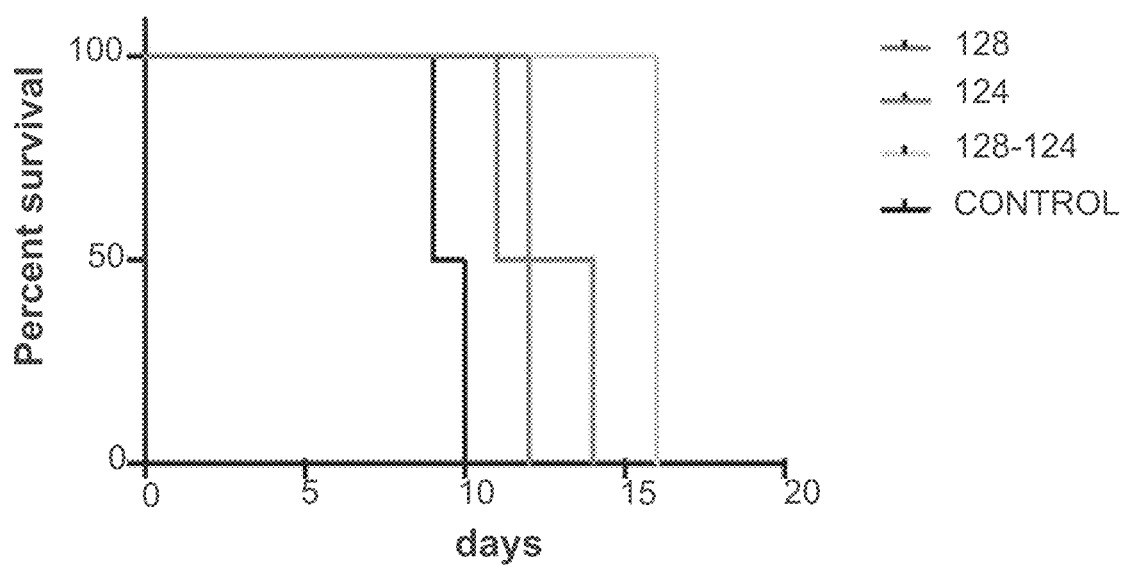

Furthermore, the combination of two microRNAs resulted in a broader downregulation of target proteins as compared to single microRNA overexpression (FIG. 3C). Importantly, cells overexpressing the miR-128-124 cluster evidenced a decreased proliferative and clonogenic capacity as compared to cells infected with control or with single microRNA vectors (FIG. 3D), and when intracranially injected into nude mice displayed a much less aggressive behavior, resulting in statistically significant prolonged survival (FIG. 3E).

Example 4. Compensatory Upregulation of Epigenetic Regulator Proteins

Figure 4A:
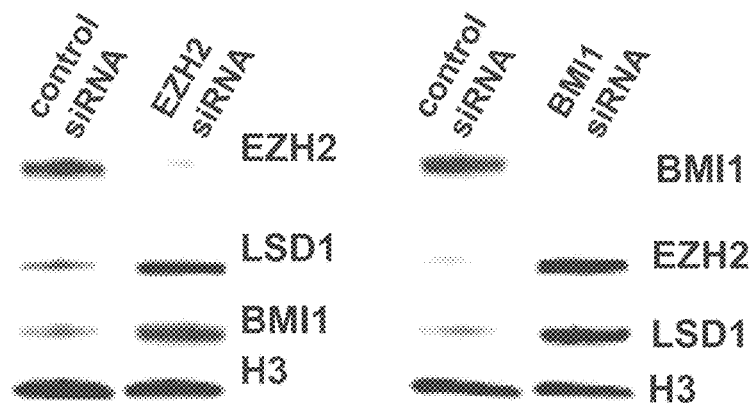
FIGS. 4A-4C illustrates compensatory upregulation of several epigenetic regulator proteins upon single knock-down of individual epigenetic regulator proteins, treatment with chemotherapeutic agents, or irradiation.
Figure 4B:
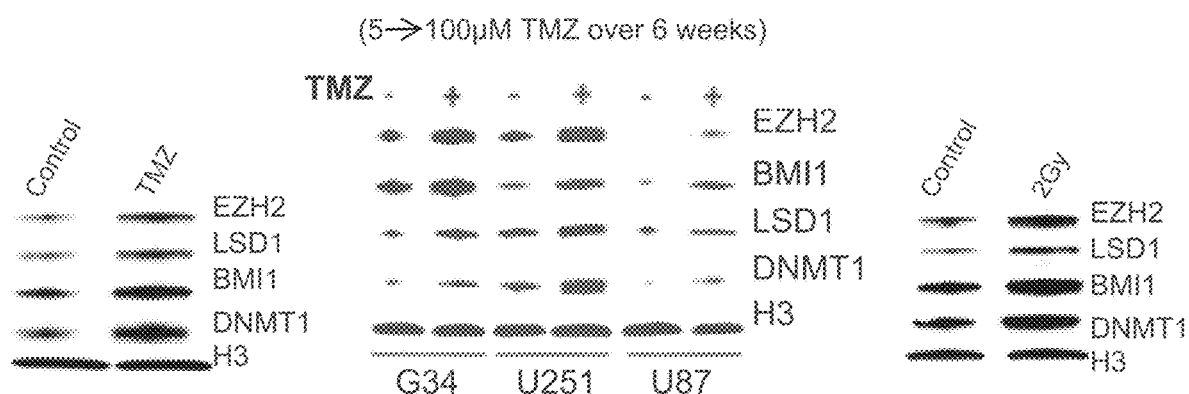
Figure 4C:
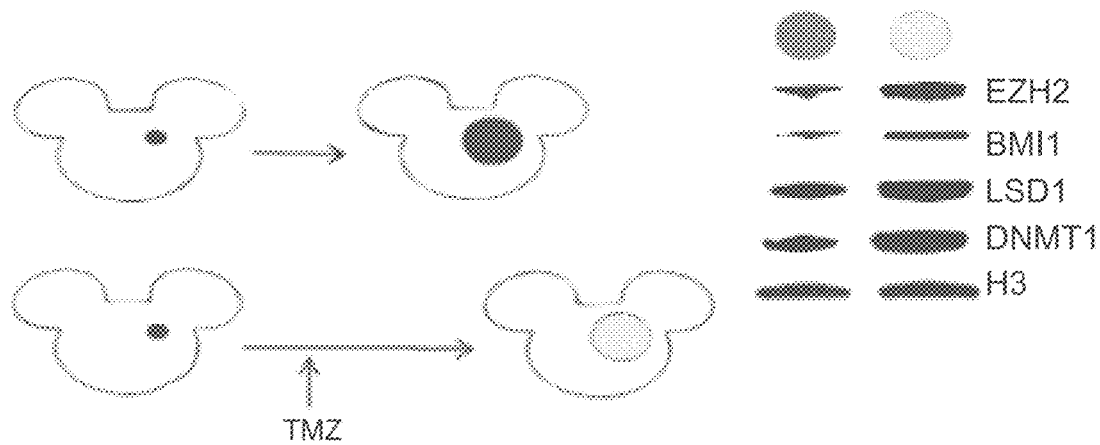

Several chromatin-associated epigenetic regulator proteins described above (EZH2, BM1 and LSD1) have been shown to be interdependent in their oncogenic function whereby downregulation of only one (by siRNA) results in upregulation of the others, as a rescue mechanism (FIG. 4A). Moreover, these proteins have been shown to be important in mediating cell survival after genotoxic stress as a consequence of DNA damage by chemotherapy with temozolomide (TMZ) or radiation (FIG. 4B). GBM cells upregulate these proteins as a survival mechanism, and this change persists over time. This has been verified also in vivo (FIG. 4C). These results underscore the utility of using artificial microRNA clusters to target multi-protein cellular signaling pathways associated with disease.

Example 5. Engineering Multiple microRNAs into a Polycistronic DNA Sequence for Vector-Mediated Delivery to GBM Cells Since some microRNAs exist in nature encoded in clusters within a short genomic DNA segment (<5 kbp), such sequences are useful as genetic scaffolds to create an artificial DNA sequence capable of encoding virtually any microRNA or combination of microRNAs contemplated, and could provide a technical solution to the application of the strategy of simultaneously overexpressing multiple microRNAs of choice. In this example, the sequence of the miR-17-92 cluster was chosen as a scaffold since it encodes a large number of microRNAs within the shortest DNA segment (~900 bp).

Figure 5A:
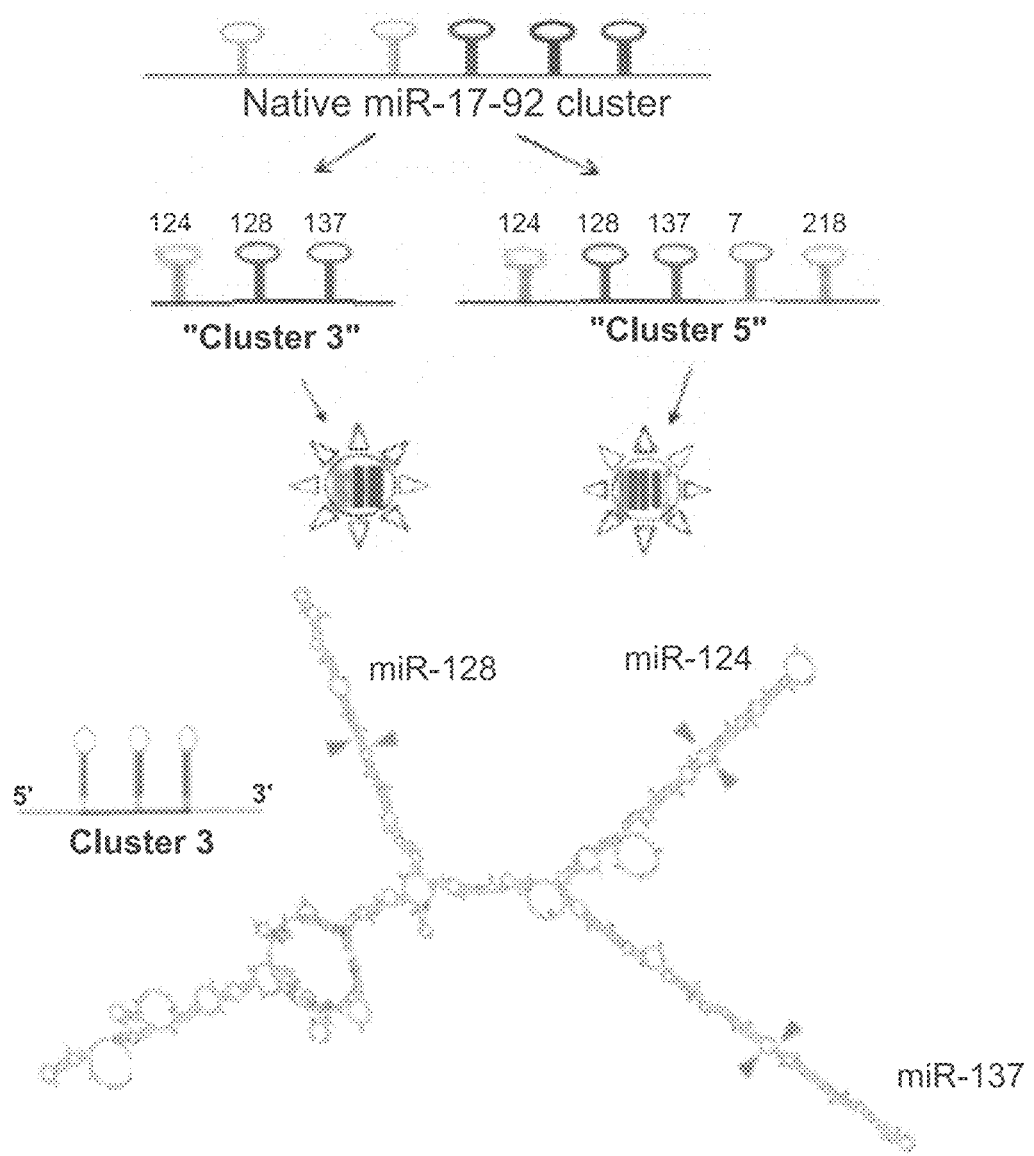
FIGS. 5A-5F illustrates the production and use of Cluster 3, Cluster 5, and Cluster 6 (miR-124, miR-128, miR-137, miR-7, miR-218, miR-34), and their biological significance.
Figure 5A:
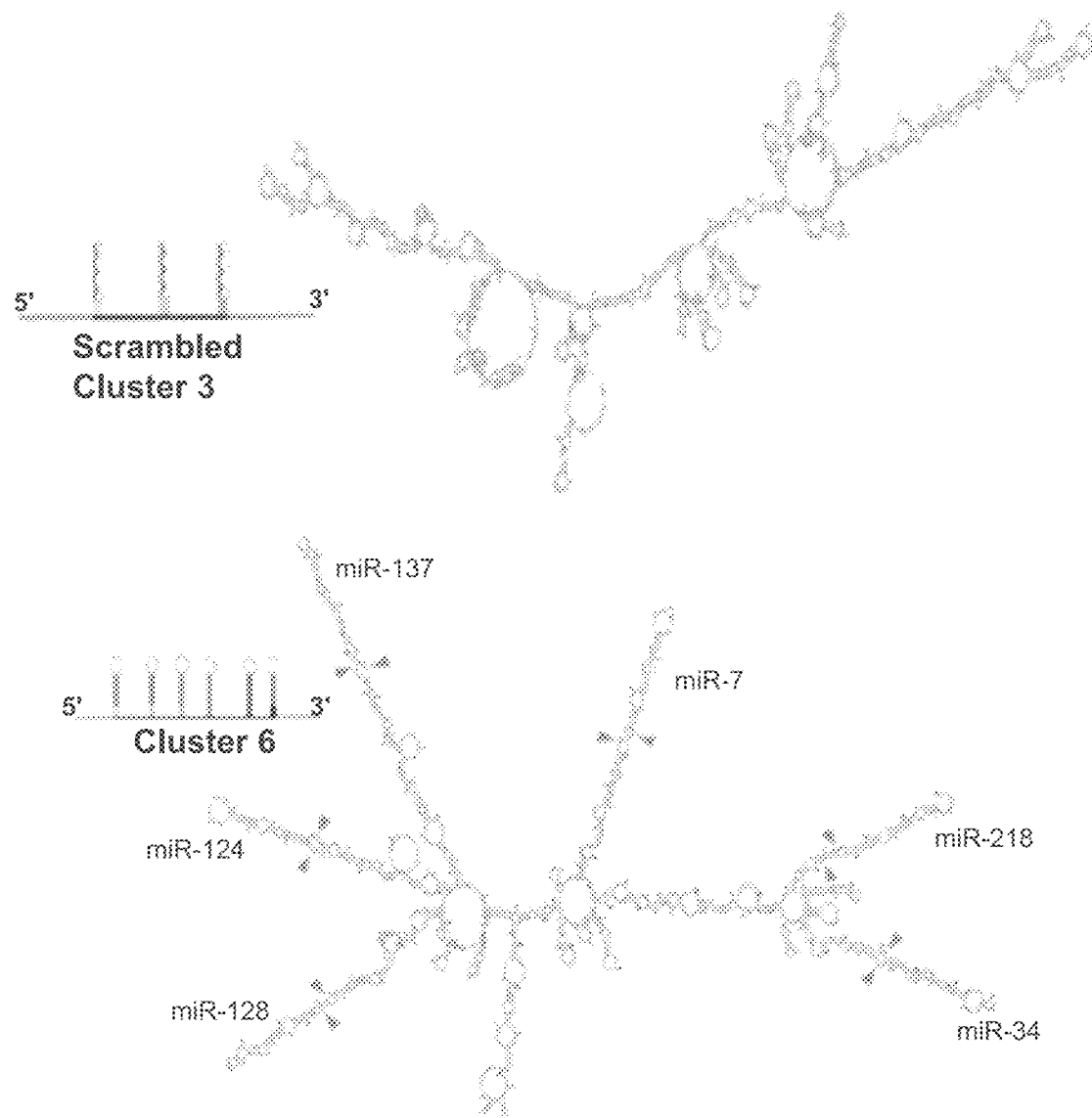

In engineering an artificial microRNA cluster, the ~70 nucleotide sequences encoding for each native microRNA hairpin found in the miR-17-92 cluster were removed and substituted with the ~70 nucleotide sequences encoding heterologous microRNAs of choice (either miR-124, miR-128 and miR-137 (Cluster 3), miR-124, miR-128, miR-137, miR-7, and miR-218, (Cluster 5), or miR-124, miR-128, miR-137, miR-7, and miR-218, and miR-34 (Cluster 6)). Secondary structures of the microRNA sequence of Cluster 3 and Cluster 6, as well as a scrambled control sequence for Cluster 3 are shown in FIG. 5A.

Figure 5B:
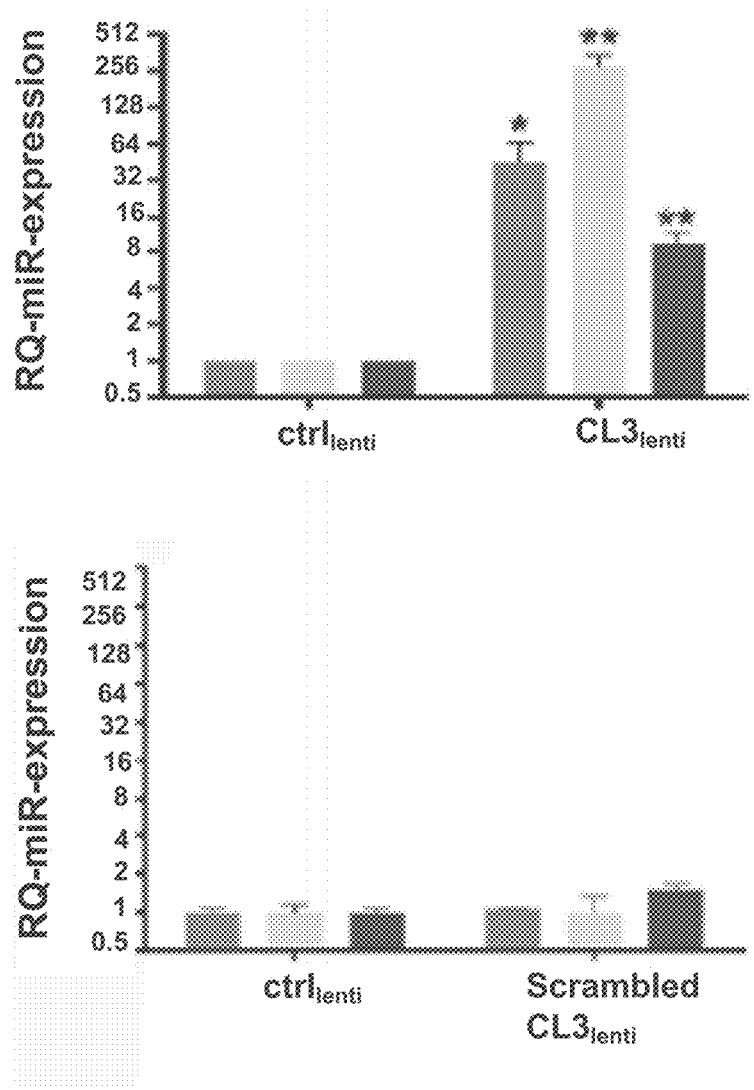
Figure 5B:
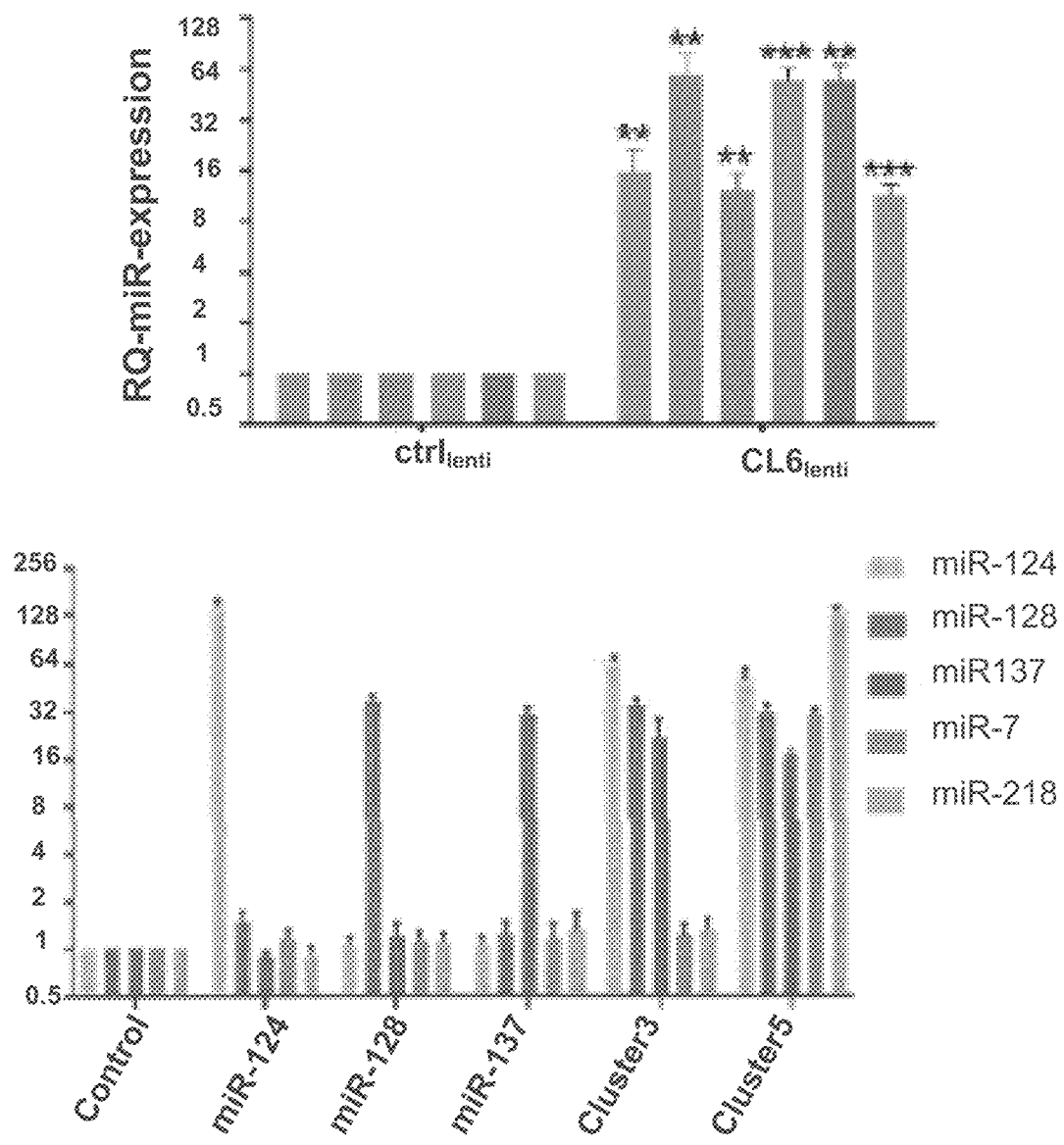

The artificial DNA sequences were subsequently cloned into a retroviral (lentiviral) vector (pCDH-GFP, System Biosciences) which was then used to stably transduce multiple GIC lines and induce overexpression of the microRNAs (FIG. 5A) as assayed by qRT-PCR in glioblastoma initiating cells (GICs; FIG. 5B).

Figure 5C:
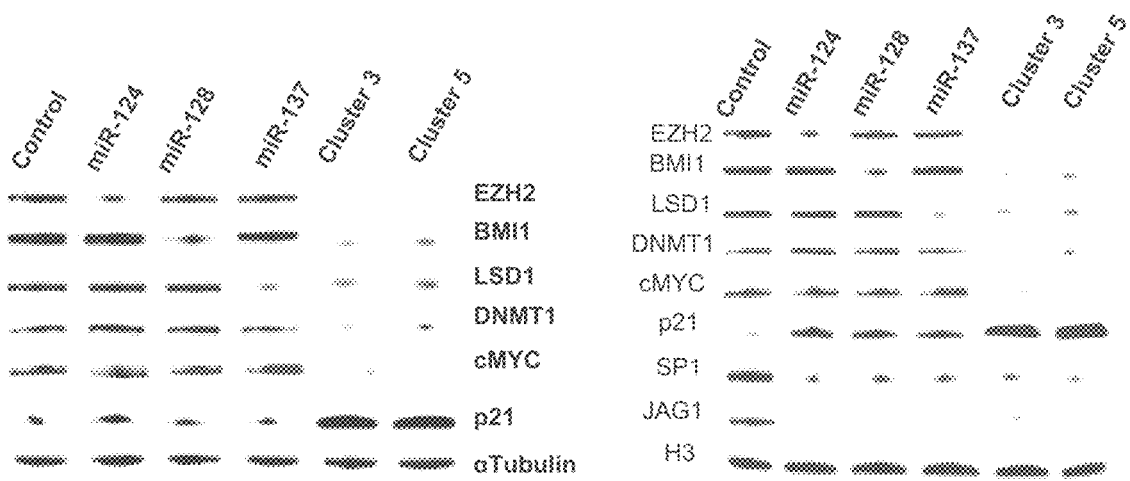
Figure 5D:
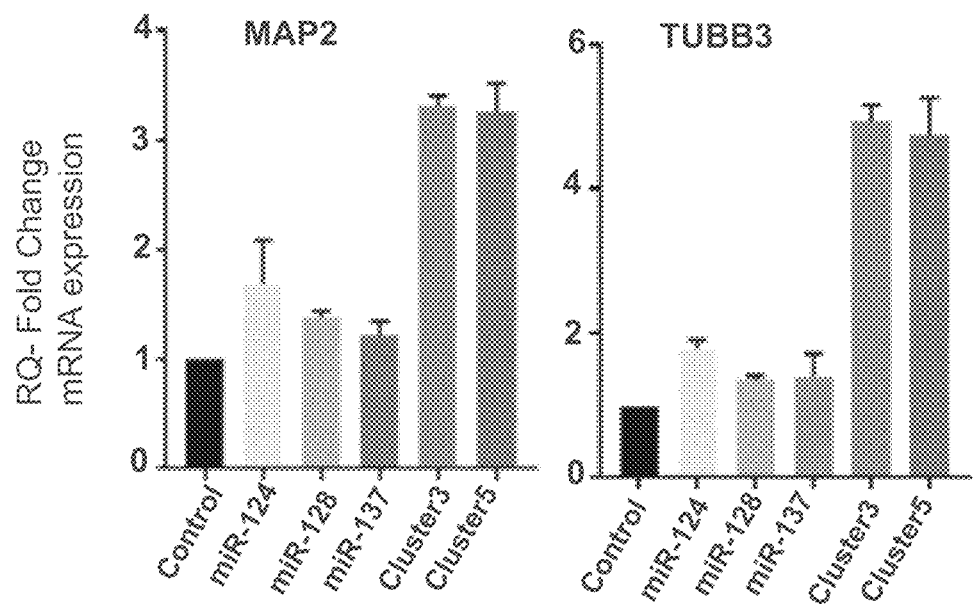
Figure 5E:
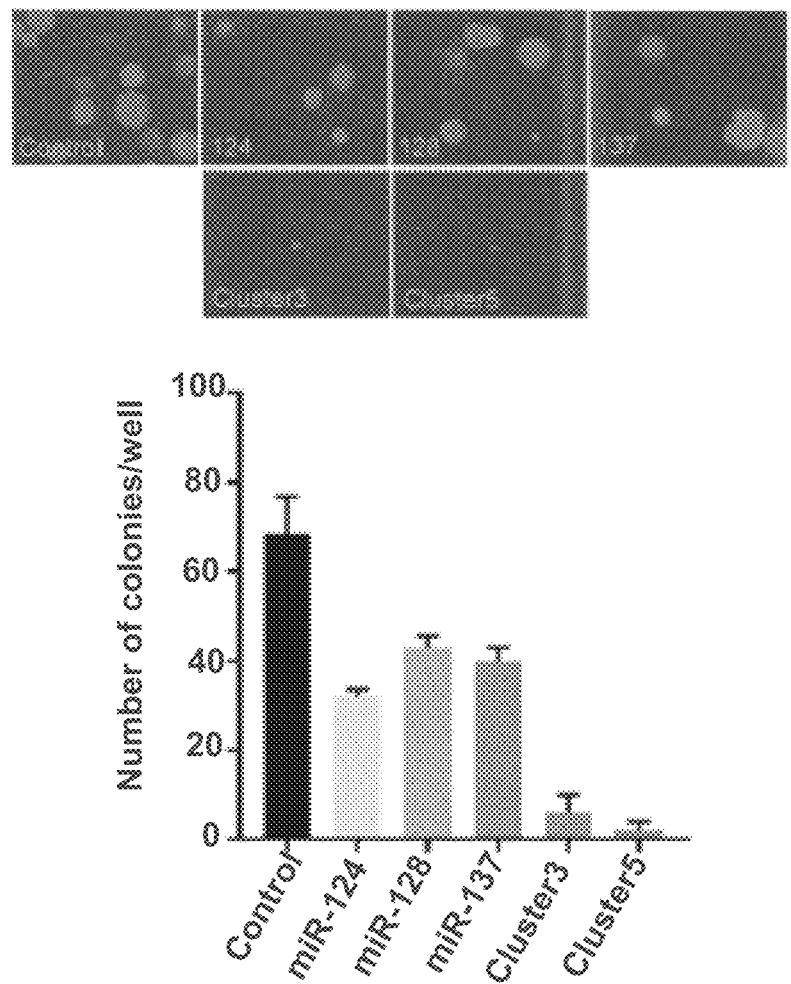
Figure 5F:
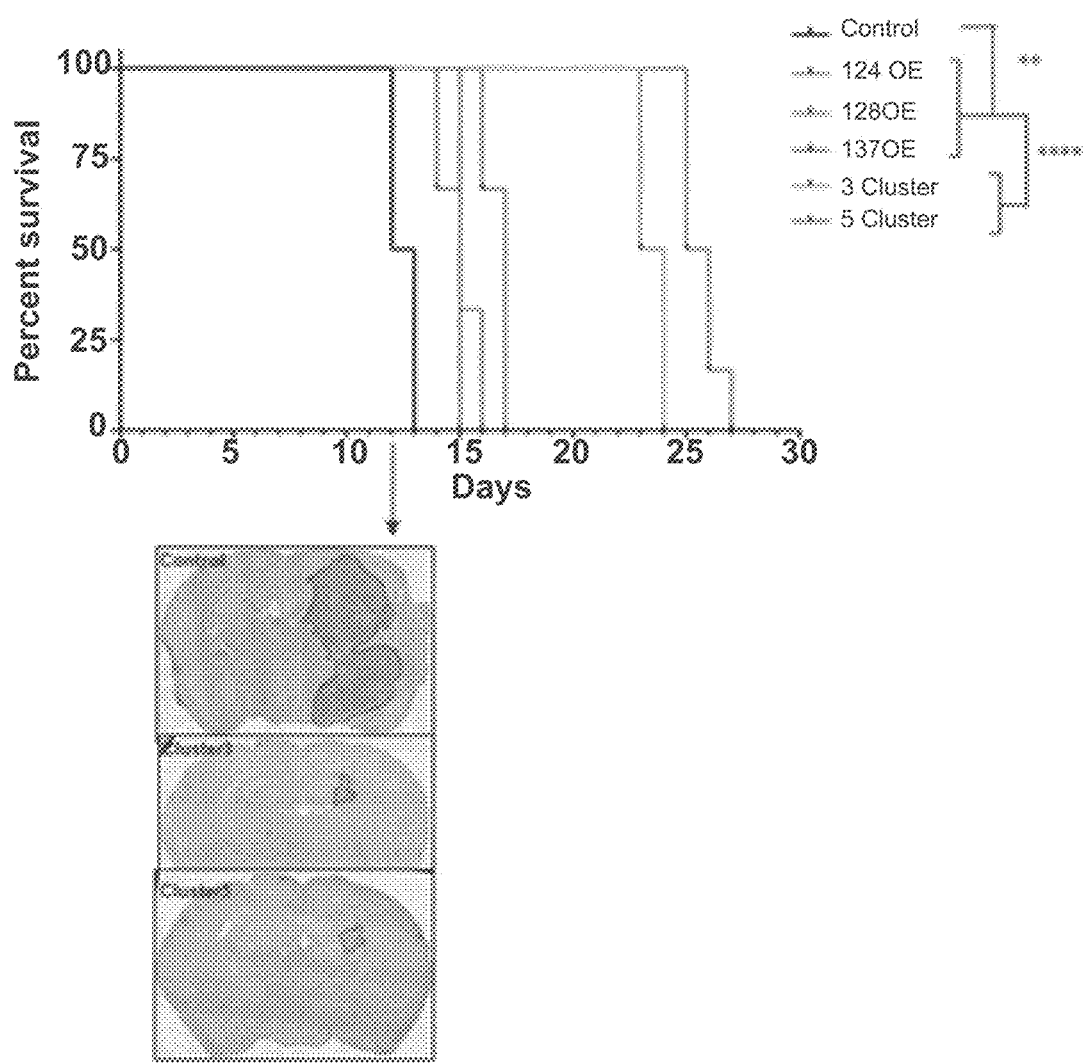

Overexpression of each microRNA did not induce expression of the others, evidencing a functional independence among the five microRNAs (FIG. 5B). Transduction with the viral vector encoding a scrambled Cluster 3 sequence did not produce detectable increases in microRNAs encoded by the normal Cluster 3 sequence, confirming the importance of sequence specificity for producing mature microRNAs encoded from artificial clusters. Biologically, this resulted in downregulation of multiple specific targeted epigenetic proteins, but, most significantly, also downregulation of other non-target proteins (DNA methyltransferase 1 (DNMT1) and MYC proto-oncogene BHLH transcription factor (MYC)), an effect which was not obtained with upregulation of single microRNAs and which confirmed a synergistic effect of this clustered approach (FIG. 5C). The synergistic effect was observed also at (i) the level of induction of markers of neuronal differentiation, microtubule associated protein 2 (MAP2) and tubulin beta 3 class III (TUBB3) (FIG. 5D), (ii) cell clonal ability (FIG. 5E), (iii) proliferation and (iv) survival in an intracranial mouse model (FIG. 5F).

Figure 6A:
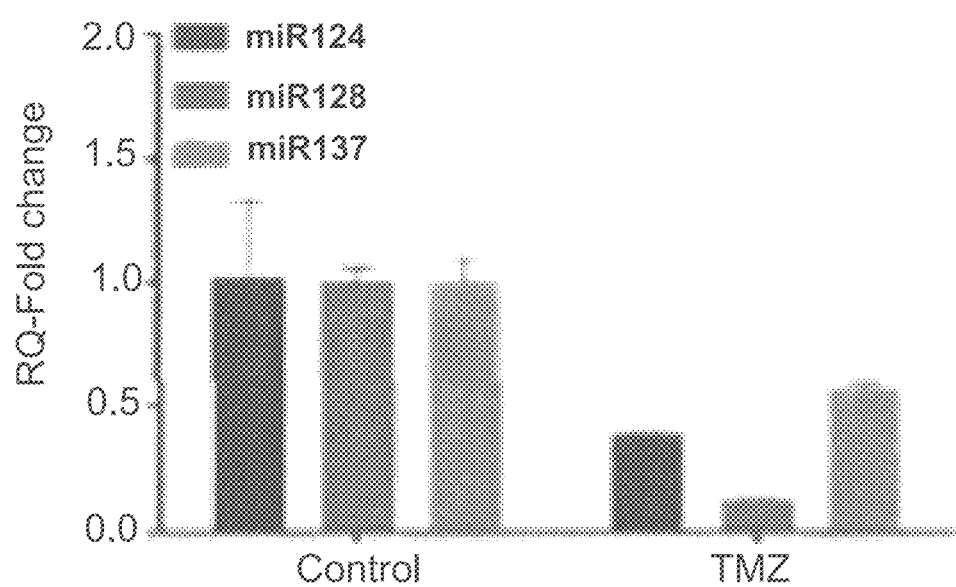
FIGS. 6A-6F illustrates the effect of clustered microRNAs on GBM cells treated with TMZ or irradiation.

Example 6. Clustered microRNAs Combined with Chemotherapy Enhance GBM Cell Death and Prolong Animal Survival MiR-128 has been previously shown to impair DNA repair after irradiation of GBM cells, likely by preventing upregulation of BMI1. It has also been shown that many other proteins with epigenetic function, including EZH2, LSD1 and DNMT1, are upregulated upon sublethal cellular stress (e.g., hypoxia, temozolomide, or low dose radiation) (FIG. 4C), as well as a simultaneous further downregulation of miR-124, miR-128 and miR-137 (FIG. 6A). This response was consistent in all six GBM lines studied and for all epigenetic proteins tested. Preventing this upregulation response by administering Cluster 3 or Cluster 5 could provide a therapeutic effect against GBM. This strategy was employed as follows.

Figure 6B:
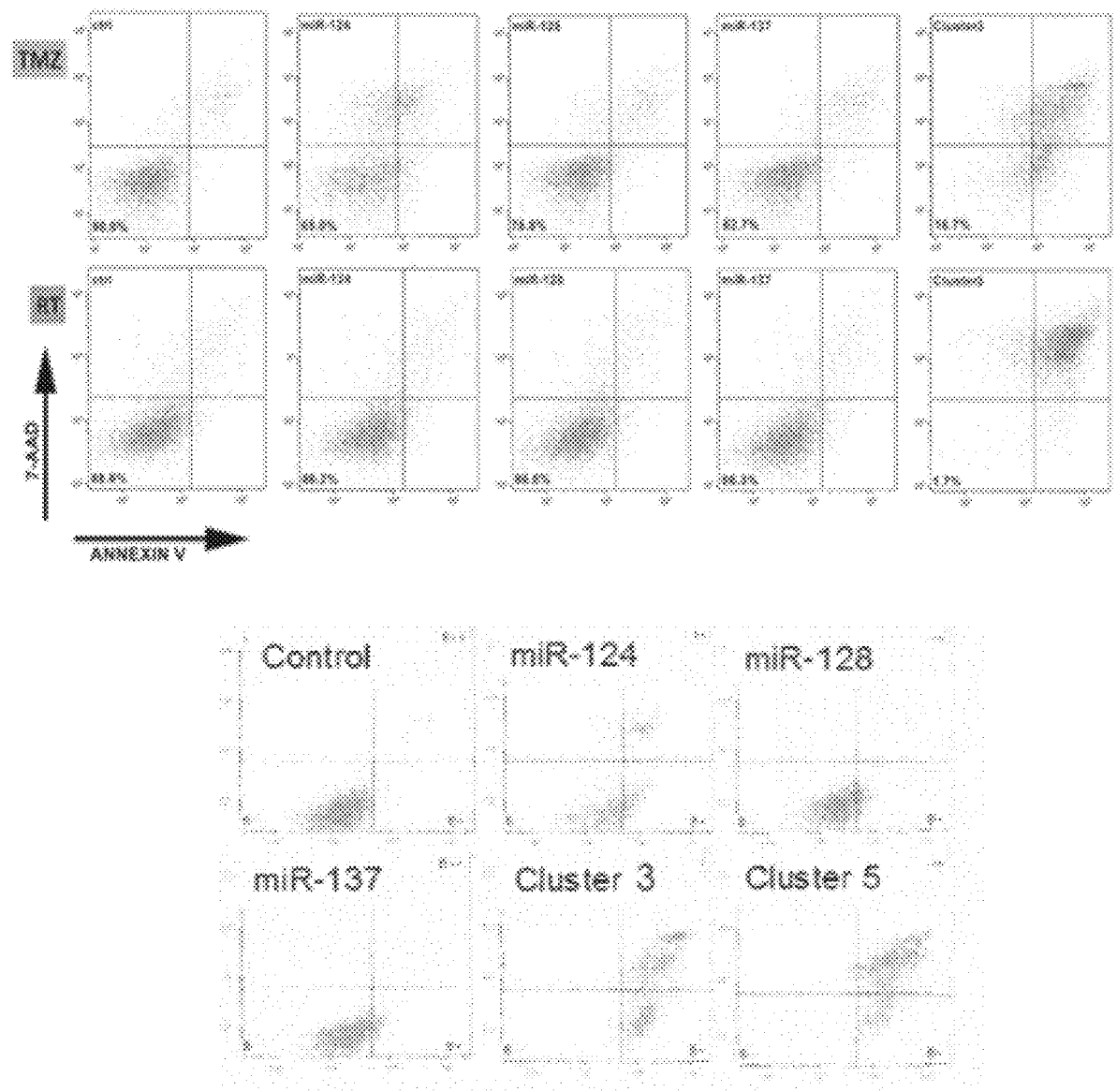

Treatment of GBM cells with TMZ or irradiation in this setting resulted in an increase in cell death (up to 85%) but only in cells overexpressing the microRNA Cluster 3 or Cluster 5 and not the single miR-137 microRNA, nor the negative control (FIG. 6B).

Figure 6C:
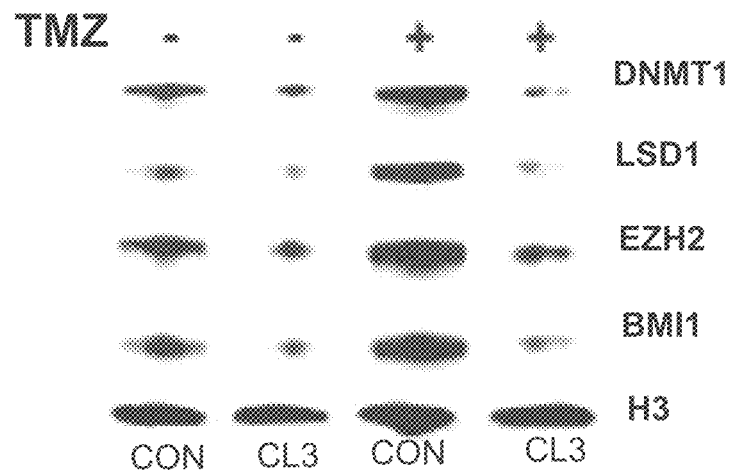
Figure 6D:
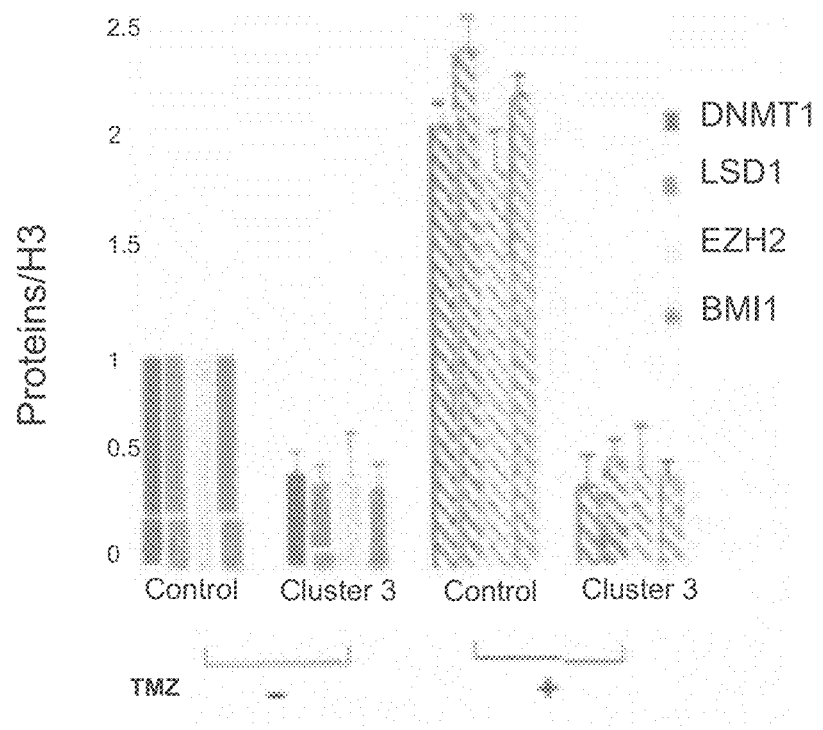
Figure 6E:
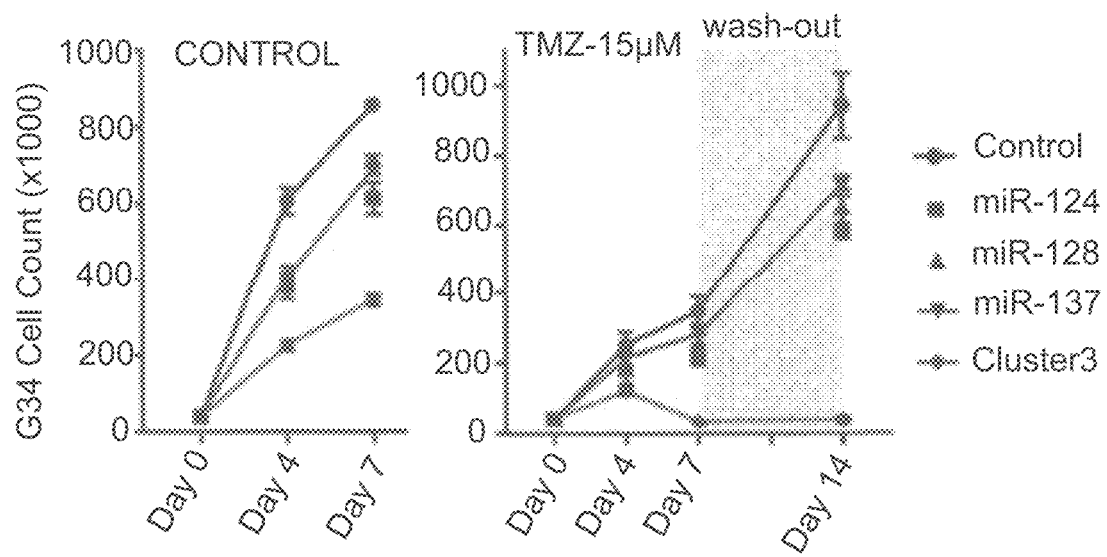
Figure 6F:
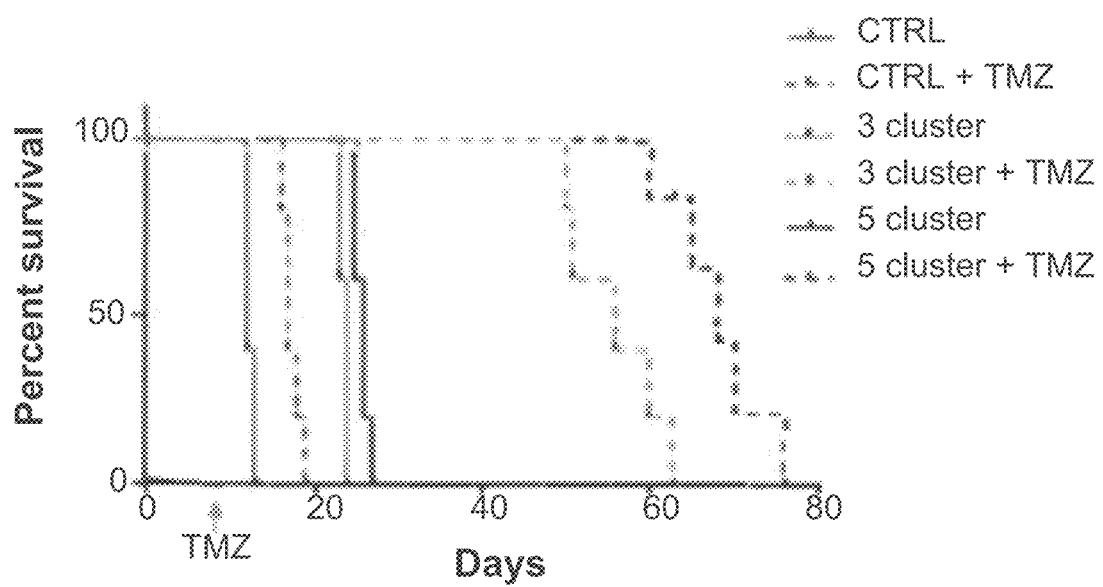

Administration of Cluster 3 to GBM cells in vitro prevented the upregulated expression of epigenetic regulators upon TMZ treatment (FIG. 6C-6D) and reduced the clonogenic potential of GBM cells (FIG. 6E). Furthermore, in an in vivo model, mice were intracranially implanted with glioblastoma initiating cells (GICs) expressing either control vector, Cluster 3 or Cluster 5 vector and treated with intra-peritoneal TMZ injections (20 mg/Kg/day for 5 days). This resulted in greater than 300% survival benefit in animals implanted with cells overexpressing multiple microRNAs vs ~40% survival benefit in animals implanted with control cells (FIG. 6F).

Example 7. Transgenic microRNAs are Transferred from Transduced Cells to Bystander Cells, and Retain their Biological Function To test the possibility that microRNAs produced from artificial microRNA clusters could potentially be released from cells transduced with the cluster-encoding construct, two stable GIC lines overexpressing GFP and either negative control or Cluster 3 (GFP+ cells), were co-cultured with GIC cells only transduced with red fluorescent protein (RFP+ cells) in a 1:1 ratio to generate mosaic neurospheres.

After 5 days, mosaic neurospheres were collected, dissociated and the RFP+ cells (Receivers) were separated by fluorescence activated cell sorting (FACS) from the GFP+ cells (Donors). RFP+ cells were then lysed and RNA and proteins were obtained and analyzed.

Bystander cells co-cultured with Donor cells had a significantly higher expression of the three mature microRNAs, but not of the transgene, suggesting that the observed microRNA increase in RFP+ cells was not due to contamination by GFP+ cells (otherwise the transgene would have been detected by PCR) and that only mature microRNAs and not the encoding transgene, were transferred. Importantly, RFP+ cells growing with Cluster3-expressing GFP+ cells showed a decrease in all epigenetic regulator proteins targeted by microRNAs, confirming that the transferred microRNAs were functional.

Figure 7A:
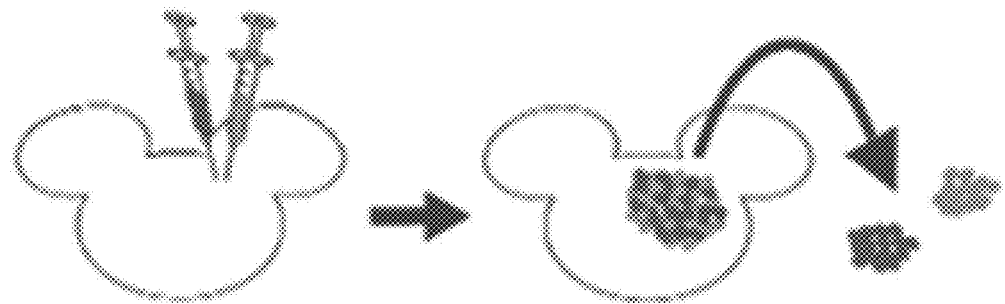
FIGS. 7A-7E illustrates in vivo evidence of cell-to-cell microRNA transfer from transduced GICs to bystander cells.
Figure 7B:
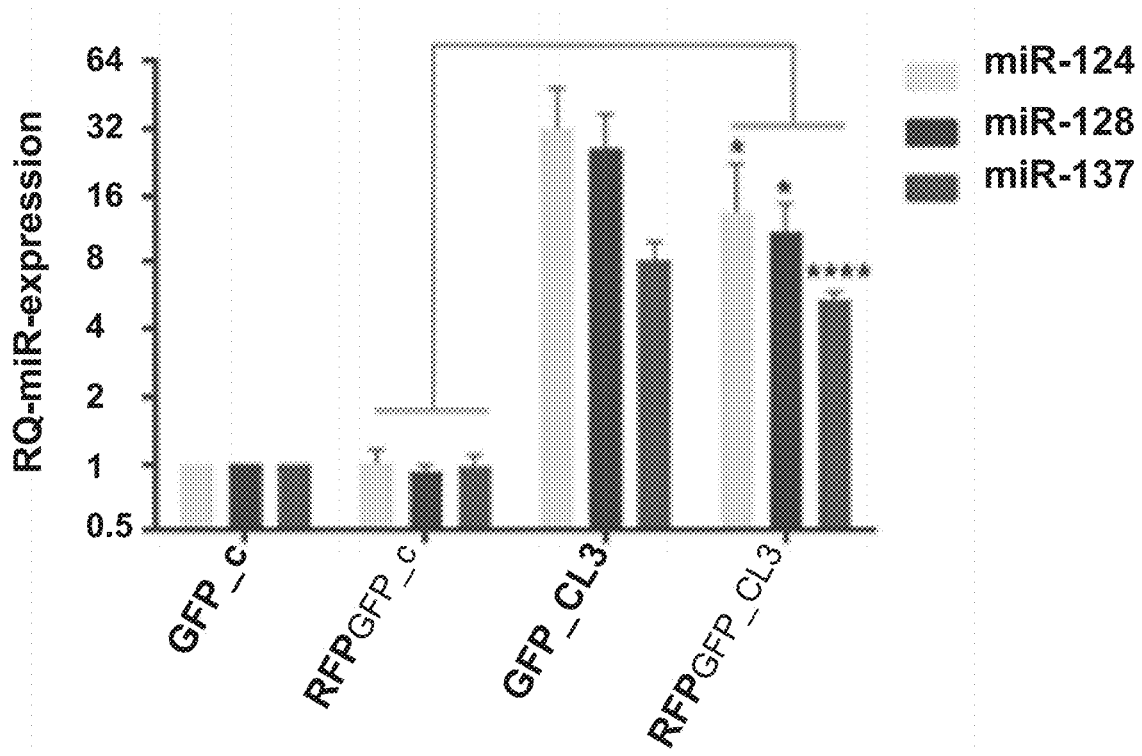
Figure 7C:
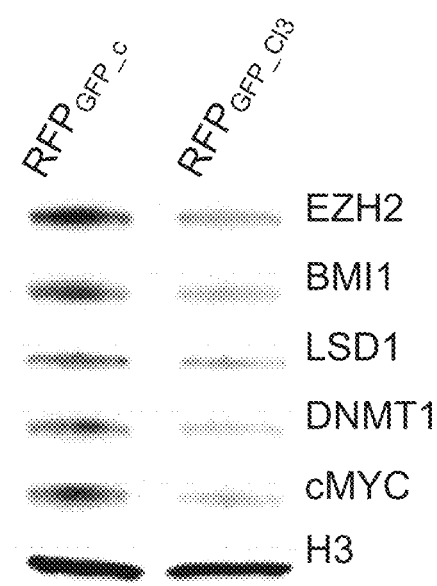

To substantiate that this effect was maintained in vivo, nude mice were intracranially injected with 5,000 RFP+ and 5,000 GFP+(expressing either negative control or Cluster 3) human GICs and tumors were allowed grow until mice became symptomatic (FIG. 7A). At day 12 post implantation, 2 mice per group were sacrificed, the tumor extracted under a microscope, dissociated, and FACS sorted to collect RFP+ cells. Replicating the findings obtained in vitro, robust transfer of microRNAs from GFP+ cells to RFP+ cells was detected as measured by qRT-PCR (FIG. 7B), and a reduction in expression of epigenetic regulator proteins in RFP+ cells was observed as measured by western blot (FIG. 7C).

Figure 7D:
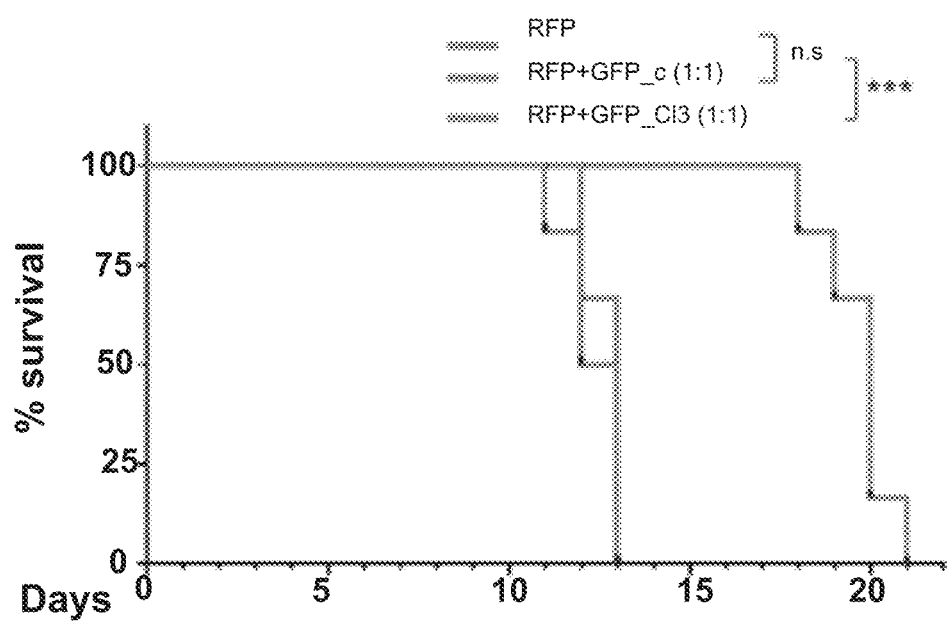
Figure 7E:
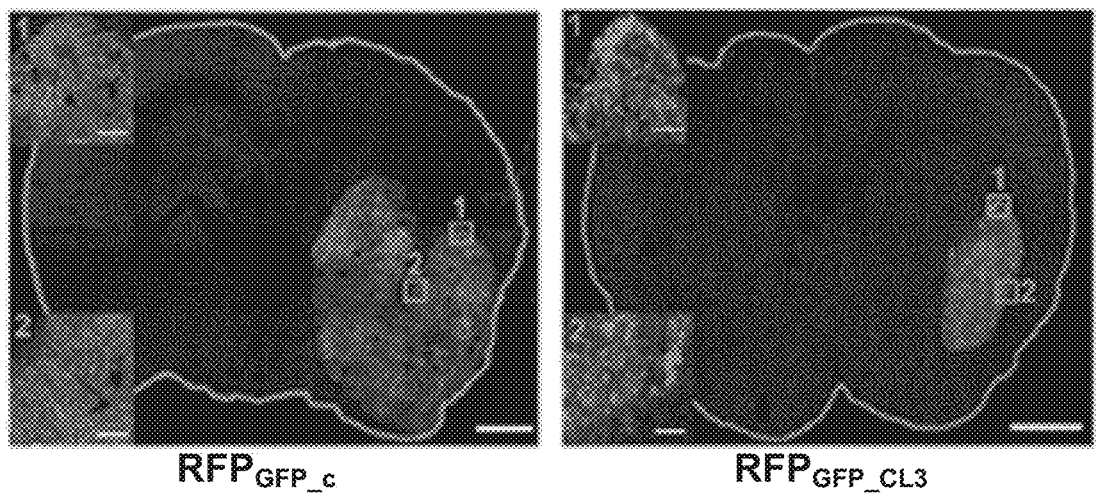

It was observed that the mice implanted with RFP+GFP-Cluster3 cells survived significantly longer than mice implanted with RFP+GFP-control and even RFP+ only (FIG. 7D) and exhibited reduced tumor burden (FIG. 7E), suggesting that a clinically relevant antitumor effect was achieved even if only a fraction of tumor cells are directly transduced by the transgene. This has important practical implications, because it represents a feasible scenario obtainable with a vector-mediated, in vivo delivery of the described transgenic microRNA clusters.

Example 8. Cell-to-Cell Transfer of Transgenic microRNAs is not Dependent on Physical Cell-to-Cell Contact The possibility that GBM cells transduced with a transgene expressing an artificial microRNA cluster could transfer expressed artificial microRNAs to bystander tumor cells without physical cell-to-cell contact (e.g., through extracellular microvesicles) was tested. This concept was tested in two co-cultured human GIC populations, one expressing an RFP transgene only (RFP+ microRNA "Receiver" cells) and the other expressing a transgene encoding GFP as well as either individual microRNAs (124, 128, or 137) or microRNA Cluster 3 (GFP+ microRNA "Donor" cells).

Figure 8A:
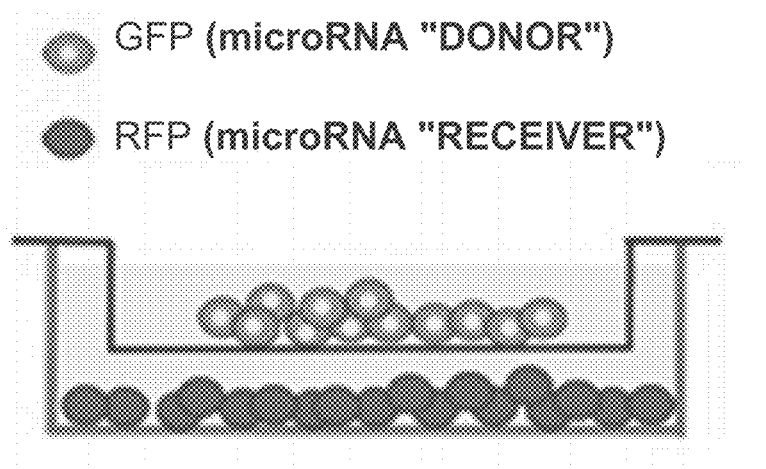
FIGS. 8A-8C illustrates an in vitro assay to determine the necessity of cell-to-cell contact for extracellular microRNA transfer.
Figure 8B:
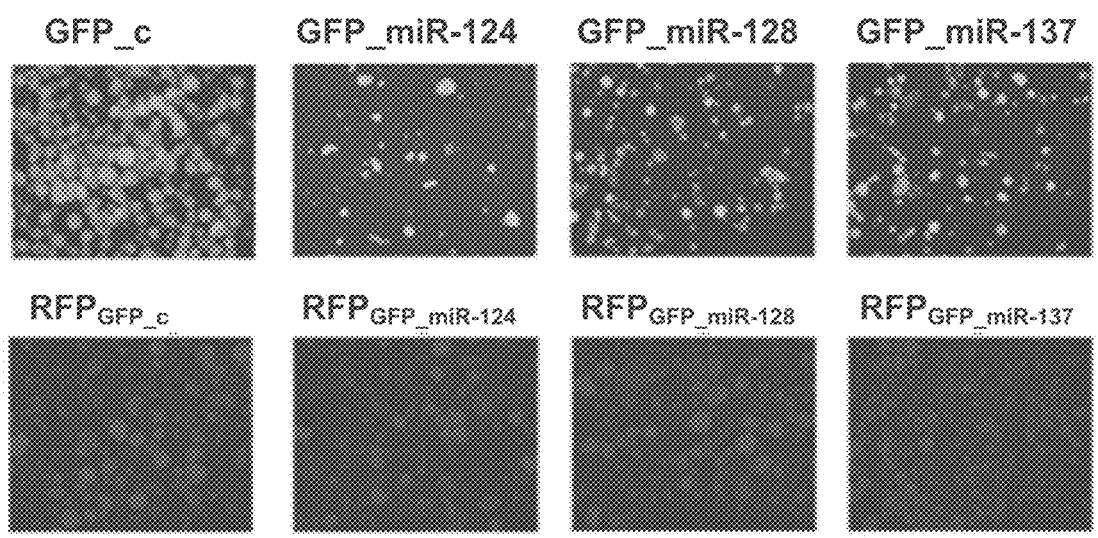

RFP+ and GFP+ cells were separated by a semipermeable membrane that permits the passage of small molecules such as soluble factors and extracellular vesicles, but precludes the two cell populations from physical cell-to-cell contact (FIG. 8A). After five days of co-culture, the clonogenic potential of the two cell populations was compared by comparing colony formation of RFP+ and GFP+ cells expressing microRNAs individually or as a cluster. GFP+ cells expressing individual microRNAs showed modest reductions in colony formation with respect to the control GFP+ cells, while RFP+ cells co-cultured with the control or single-microRNA-expressing GFP+ cells appeared not to be affected (FIG. 8B).

Figure 8C:
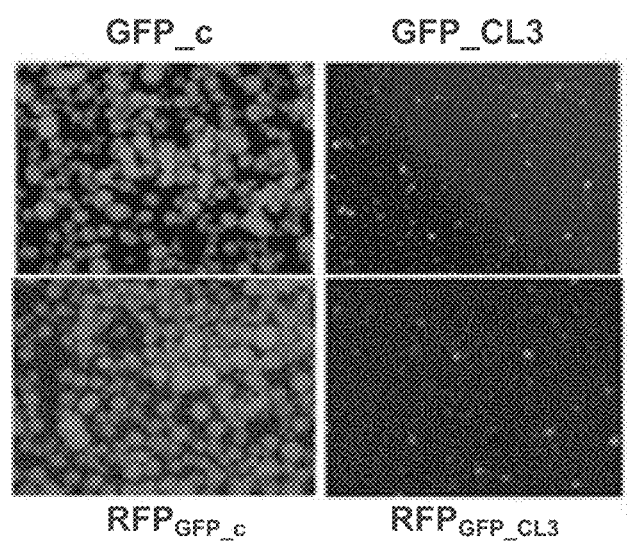

In contrast, when GFP+ cells expressed Cluster 3, both GFP+ and RFP+ cells showed a substantial reduction in colony formation, even though RFP+ cells were not directly transduced with the Cluster 3 transgene (FIG. 8C). This finding demonstrates that microRNAs expressed in the Donor cells were transferred to the Receiver cells absent any physical cell-to-cell contact.

Figure 9A:
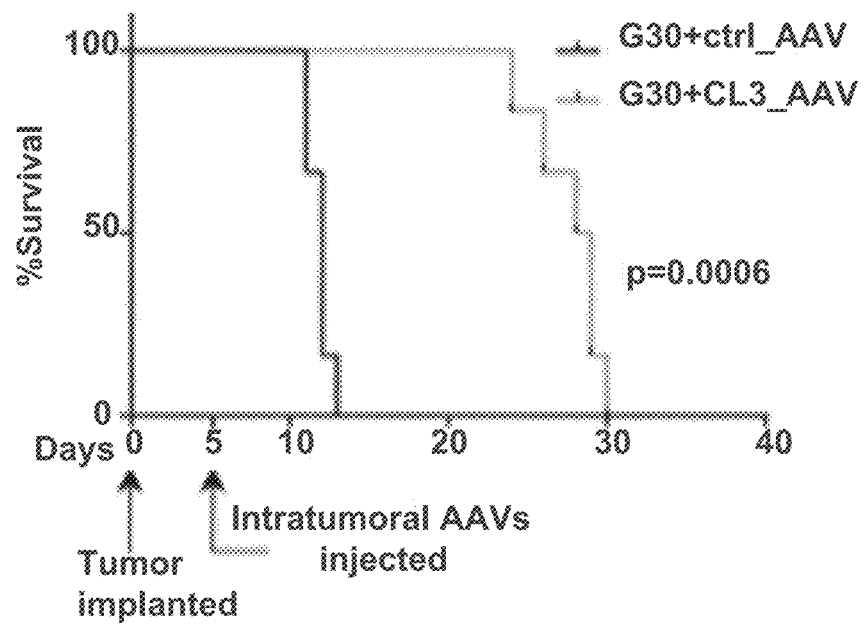
FIGS. 9A-9B illustrates the effect of adeno-associated viral 2 (AAV2)-mediated delivery of Cluster 3.
Figure 9B:
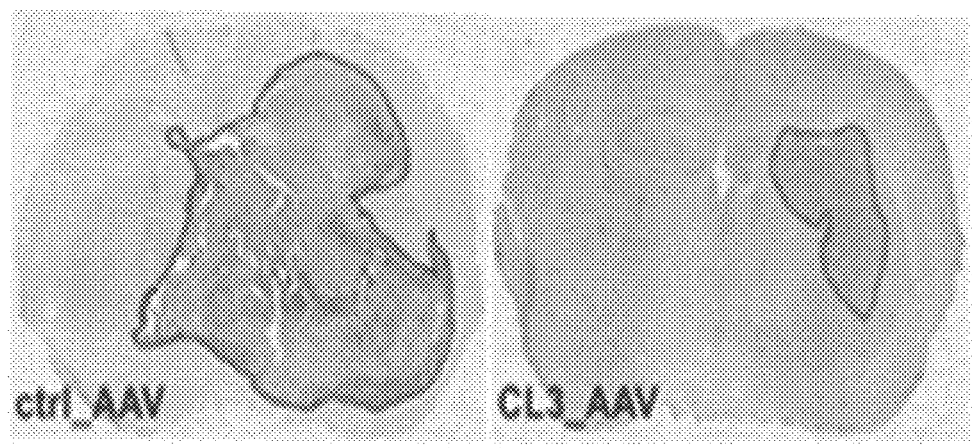

Example 9. Adeno-Associated Viral (AAV) Vectors are Suitable Expression Vectors for Artificial microRNA Constructs in Mammals In Vivo AAV expression vectors were tested for the ability to efficiently deliver transgenes encoding artificial microRNA clusters in mice in vivo. GBM tumor cells were first implanted into the brains of mice in vivo at day 0. Five days later, AAV2 vectors encoding either a control construct or a transgene encoding cluster 3 were injected intratumorally. Mice injected with the AAV2 vector encoding Cluster 3 showed almost a 3-fold increase in survival benefit (FIG. 9A) and reduced tumor growth (FIG. 9B) compared to mice receiving the control construct despite the absence of any other treatments. These findings demonstrate that AAV vectors are useful for therapeutic delivery of transgenes encoding artificial microRNA clusters.

Figure 10A:
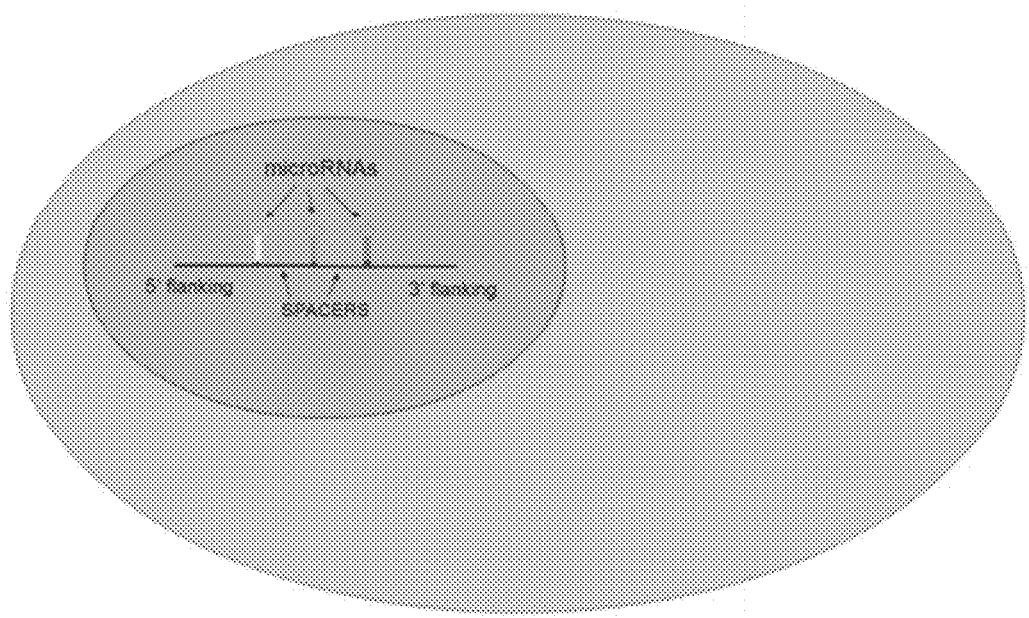
FIG. 10A-10C illustrates differential subcellular localization of microRNAs encoded within a microRNA cluster. Although microRNAs are initially processed in the cell nucleus (FIG. 10A), the microRNA hairpins as well as the 5 and 3' flanking sequences are transported out of the nucleus into the cytoplasm, while the spacer sequences between microRNA hairpins remain in the nucleus, as they do not have nuclear export signals (FIG. 10B).
Figure 10B:
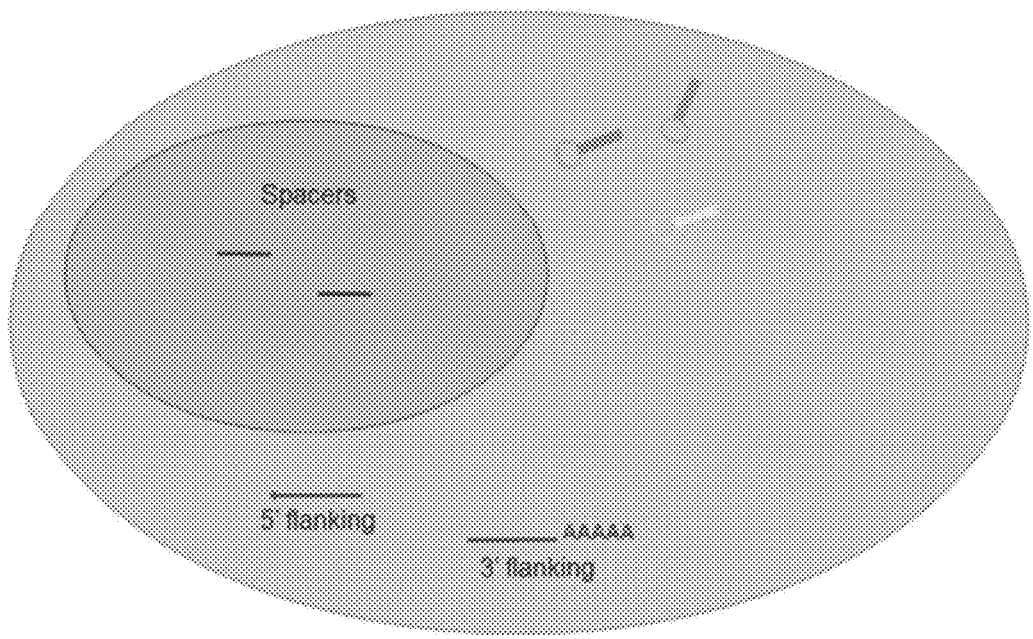
Figure 10C:
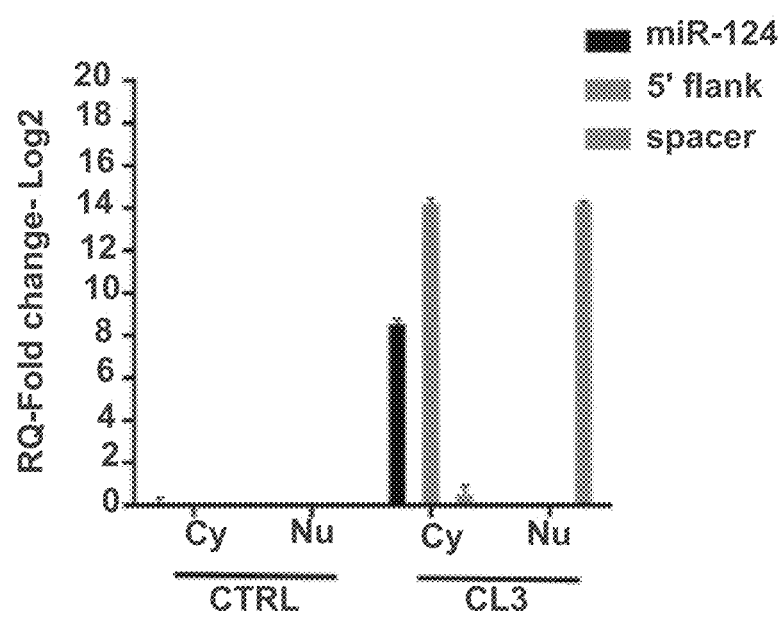

Example 10. Leveraging Differential Subcellular Localization of Non-Coding RNAs Derived from Processing of Artificial microRNA Constructs Nucleic acid sequences surrounding the microRNA hairpins of a microRNA cluster were previously presumed to be removed and degraded during intracellular processing of microRNAs to produce mature microRNA hairpins. Experimental detection of these surrounding sequences, however, confirmed that they are retained inside of the cell, suggesting that the artificial microRNA constructs of the present invention produced not only the artificial microRNA hairpins, but additional non-coding RNA byproduct sequences as well. These non-coding RNAs distribute either in the cytoplasm or the nucleus, depending on their initial location within the primary transgene transcript. In particular, both 5' and 3' flanking sequences are transported to the cytoplasm, while spacer sequences between microRNA hairpins remain in the nucleus since they do not have nuclear export signals (FIGS. 10A-10B). PCR analysis from cytoplasmic (Cy) and nuclear (Nu) extract confirmed the persistence and distribution of these sequences (FIG. 10C).

Figure 11A:
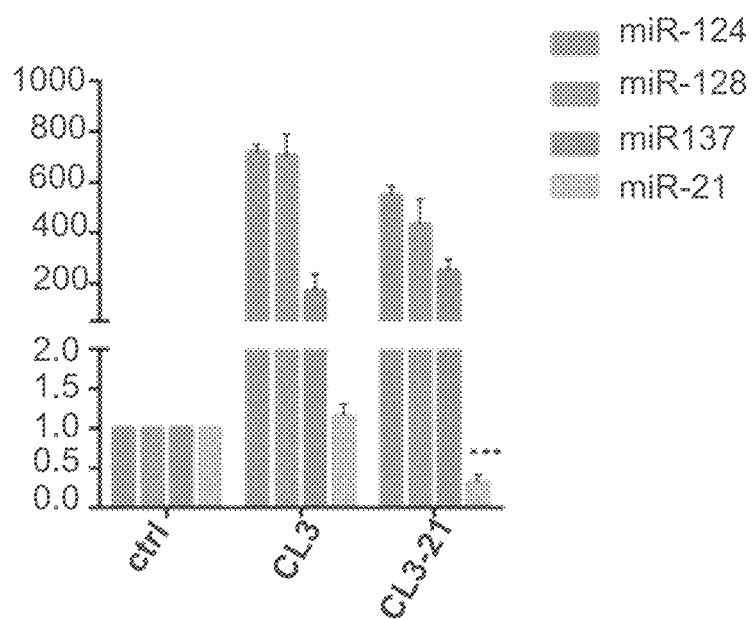
FIGS. 11A-11F illustrates expression and activity of a modified Cluster 3 construct which incorporates an additional non-coding RNA sequence antisense to miR-21 in its 5' flanking sequence.
Figure 11B:
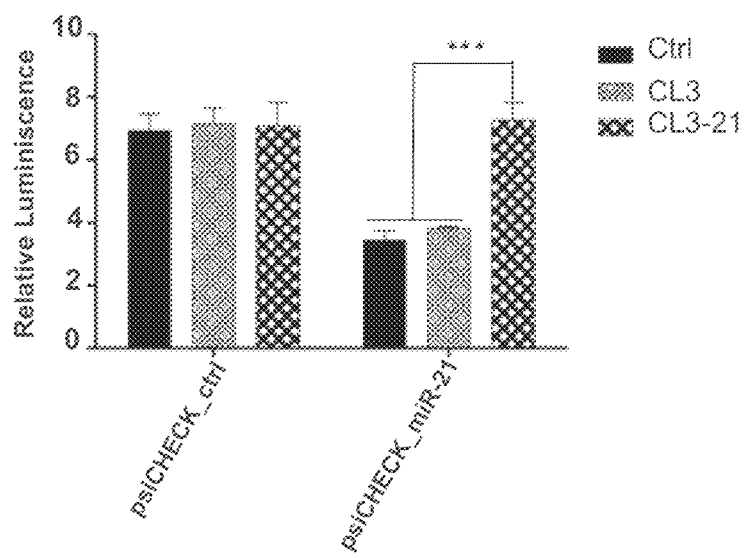
Figure 11C:
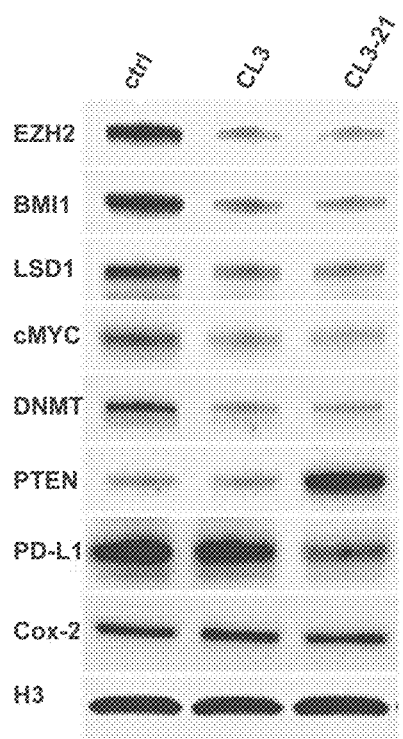
Figure 11D:
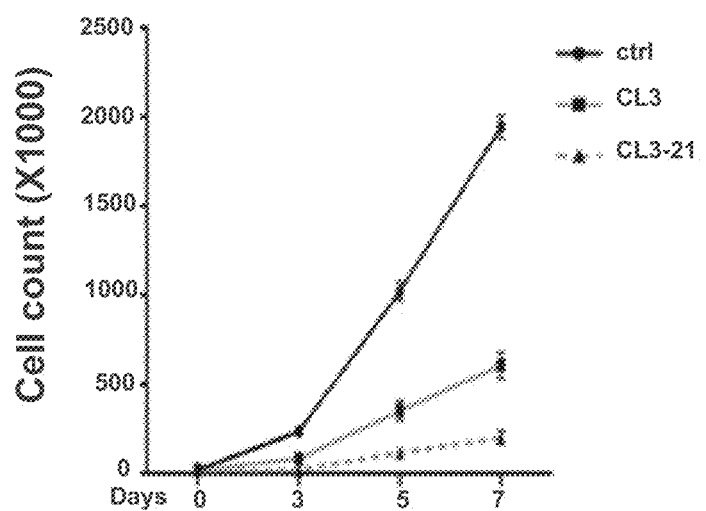
Figure 11E:
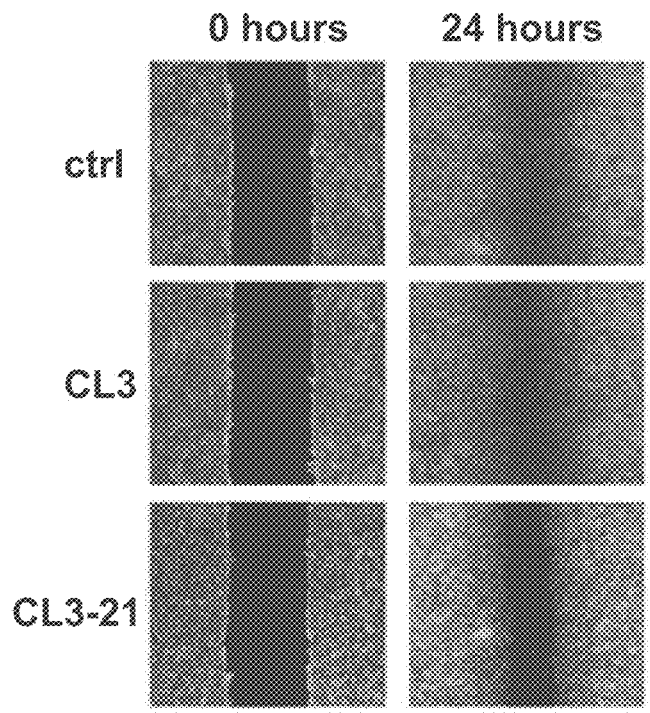
Figure 11F:
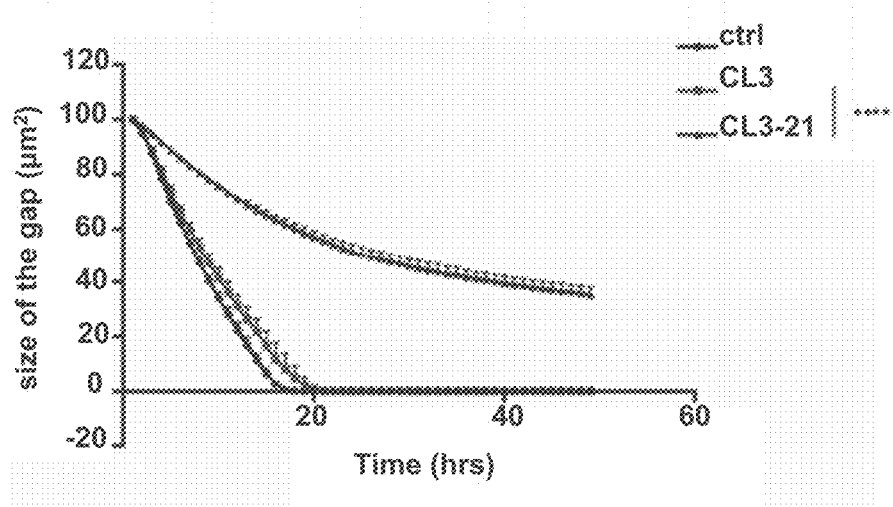

Example 11. Sequestering Deleterious microRNAs in the Cytoplasm Using microRNA Sponge Sequences Encoded within Flanking Sequences of Artificial microRNA Constructs The non-coding RNA byproduct sequences produced from the intracellular processing of the microRNA cluster described in Example 10 and previously believed to be "junk", were tested for their ability expand the biological effect of the artificial microRNA cluster constructs of the present invention. Since 5' and 3' flanking sequences are transported to the cytoplasm, they can be used as sponges to sequester unwanted microRNAs (e.g., microRNA sponges), in consideration of the fact that mature microRNAs are usually concentrated in the cytoplasm. Thus, the 5' flanking sequence used in the first version of Cluster 3 was modified with a sequence of similar length containing a miR-21 antisense sequence (e.g. a miR-21 sponge sequence). The new transgene (CL3-21) still produced the microRNAs but also induced a measurable decrease in the level of mature miR-21, suggesting the presence of a functional microRNA sponge (FIG. 11A-B). This was further verified by western blotting for known targets of miR-21, the phosphatase and tensin homolog (PTEN) and programmed cell death 4 (PDCD4) proteins (FIG. 11C), which became upregulated, and also by the quantification of cell proliferation and migration (FIGS. 11D-11F), which are known to be affected by miR-21.

Figure 12A:
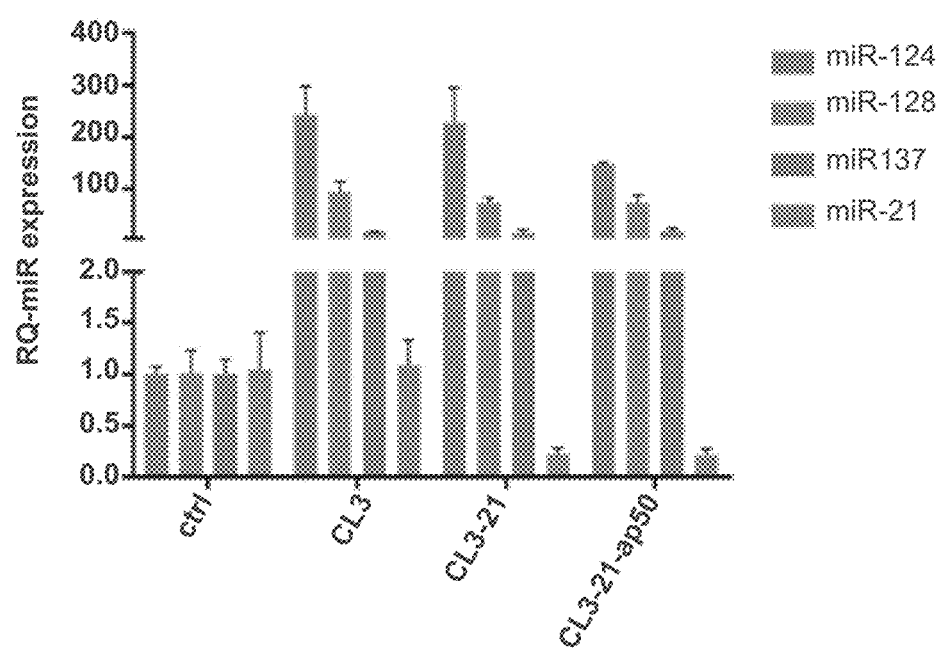
FIGS. 12A-12E illustrates the biological effects of microRNA clusters having non-coding RNA spacer sequences encoding an aptamer shown to bind p50.
Figure 12B:
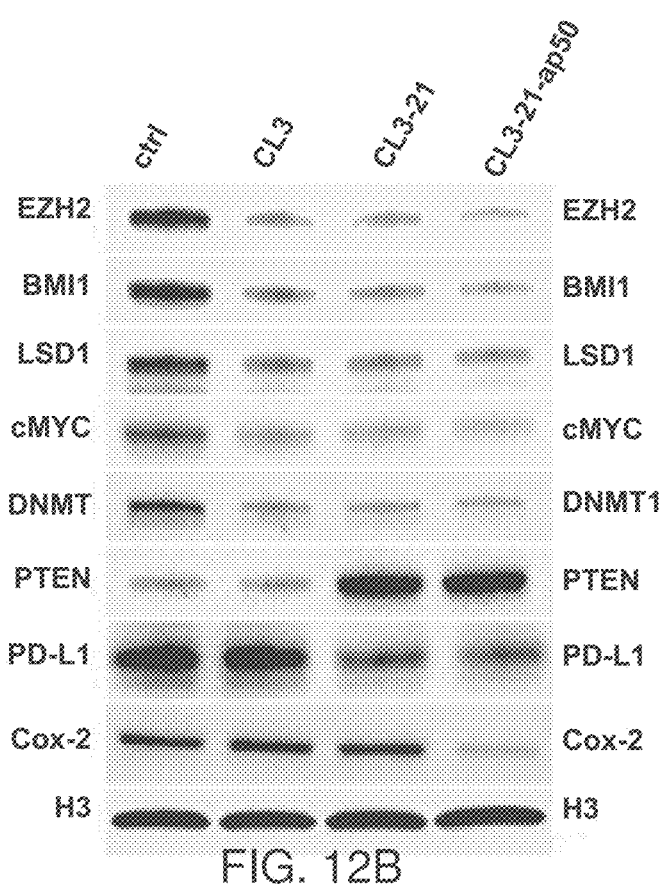
Figure 12C:
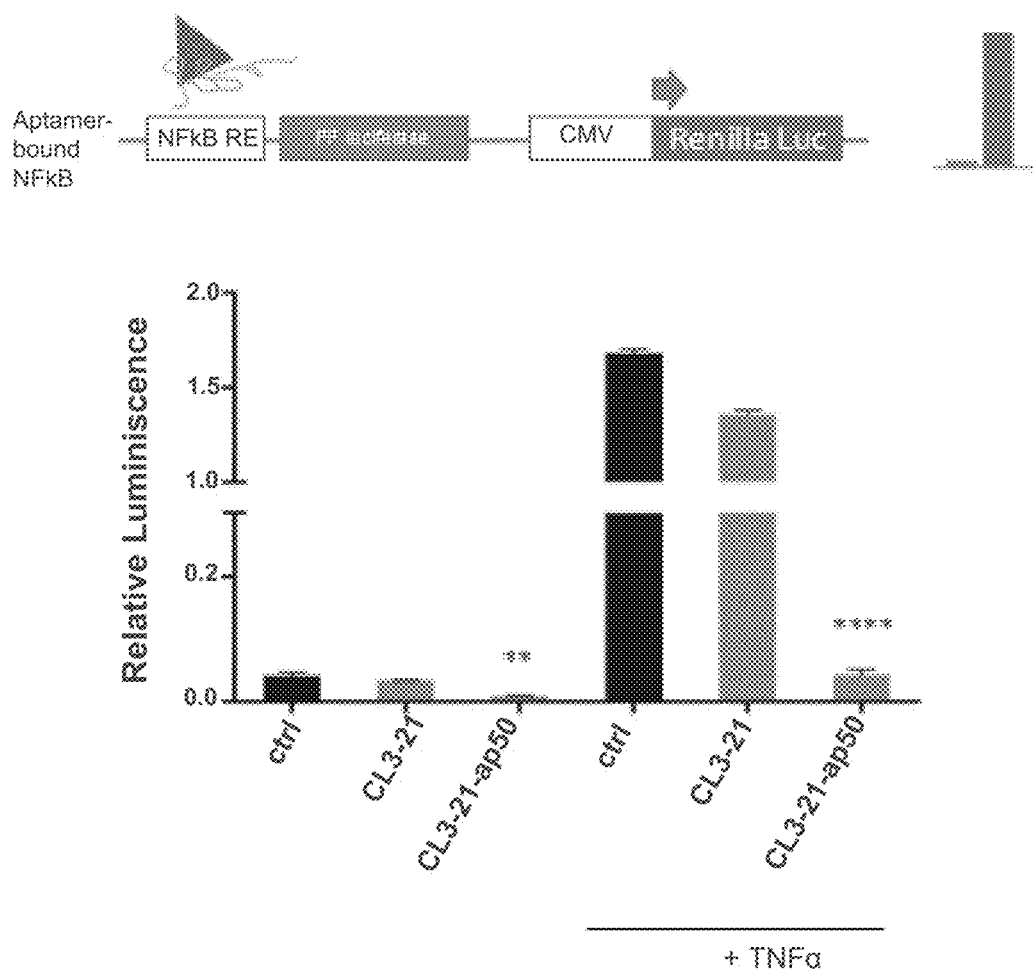
Figure 12D:
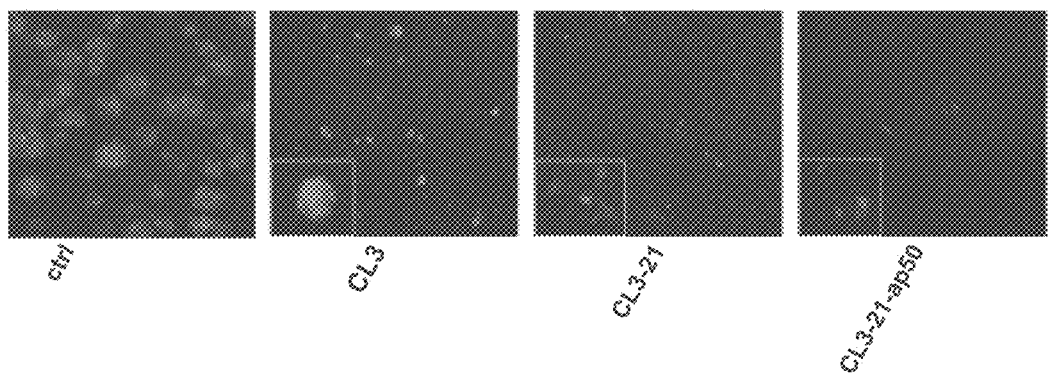
Figure 12E:
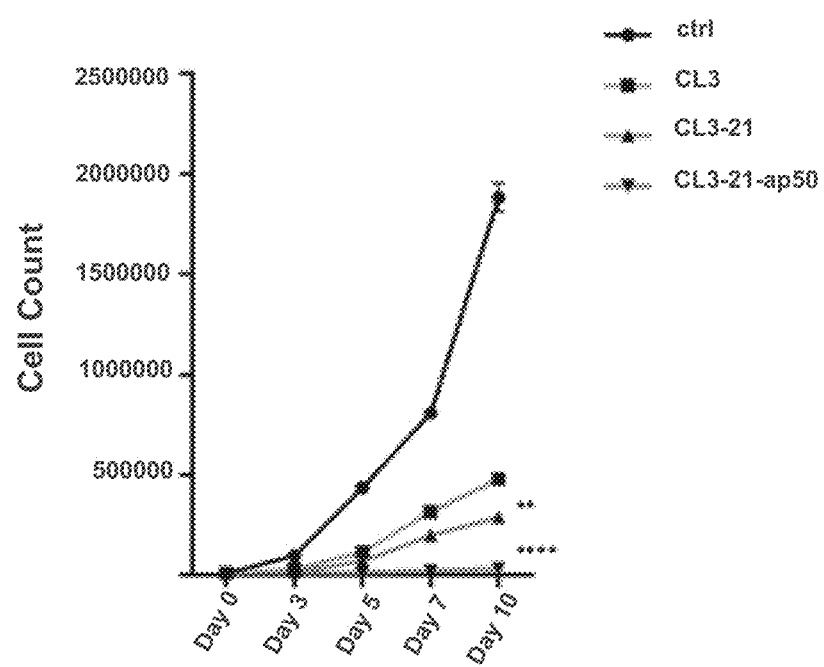

Example 12. Leveraging Nuclear Localization of the Spacer Sequences of Artificial microRNA Clusters for Therapeutic Targeting Since spacer sequences within the microRNA hairpins remain in the nucleus, they were tested for their capacity to interfere with the function of transcription factors. As a proof of principle, a new transgene was created (CL3-21-ap50) in which the first spacer sequence of the CL3-21 sponge transgene was modified with a sequence of similar length encoding an aptamer previously shown to bind to and inactivate p50, a fundamental protein in the nuclear factor kappa B subunit 1 (NFkB) pathway, which is crucial in cancer biology and a difficult therapeutic target. Aptamers are synthetic non-coding RNA or DNA molecules which assume specific tri-dimensional conformations that facilitate selective binding to proteins. Similarly to the CL3-21 construct, the sequence modification in CL-21-ap50 did not alter the production of the microRNAs, nor the production of the miR-21 sponge sequence (FIG. 12A), but, in addition, inhibited p50 activation as demonstrated by using a specific NFkB-luciferase reporter system (FIG. 12C). Cell proliferation was also greatly impaired to the point that no cell growth was observed over a period of 10 days (FIGS. 12D-12E). The experimental findings provided here and in Example 11 indicate that vector-mediated delivery of artificial microRNA constructs described herein can exploit the cellular microRNA biogenesis process to introduce biologically active non-coding RNAs into cells (e.g. cells of a human subject). Such non-coding RNAs can then be used for performing a variety of functions associated with non-coding RNAs (e.g. microRNA sponge activity, aptamer activity, among others).

Example 13: Administration of Viral Vectors Encoding an Artificial microRNA Cluster to Humans In Vivo Administration of viral vectors encoding an artificial microRNA cluster may be administered to an animal to treat virtually any condition. One exemplary condition is cancer. In one working example, the patient is administered an expression vector (e.g., a retroviral vector, such as a lentiviral vector, or an AAV vector) including an artificial microRNA construct operably linked to a promoter. The transgene encoding and artificial microRNA construct may be one having a single microRNA hairpin or an artificial microRNA cluster encoding at two or more (e.g., 2, 3, 4, 5, or 6) microRNA hairpins. Such a microRNA cluster may further include non-coding RNA sequences within the 5' or 3' flanking sequences or spacer sequences. The composition containing the expression vector which includes the artificial microRNA construct may be administered to the patient, for example, systemically (e.g., by way of intravenous injection, intraperitoneal injection, oral ingestion, or inhalation) or by way of intrathecal injection, intracerebroventricular injection, intraparenchymal injection, or intratumoral injection. The composition may also be administered to the patient by virtue of first administering the composition to a population of autologous cells, as is desired and subsequently administering the cells to the patient according to standard methods. To treat GBM, the expression vector can be administered at standard doses known in the art.

Tumor growth and tumor burden, if desired, is assessed using standard imaging methods (e.g., digital radiography, PET scan CT scan, or MRI scan). Images from before and after administration of the expression vector may be compared to evaluate the efficacy of the treatment, and rate of disease progression can be assessed by comparison to the patient's medical history prior to administration of the vector. A finding of a reduction in the total number of tumors, number of primary tumors, volume of tumors, growth of tumors, or rate of disease progression provides a basis for evaluating the usefulness of the expression vector. Subsequent doses may be administered as needed.

Other Embodiments

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure. Other embodiments are in the claims.

What is claimed is:

1. A composition comprising a non-naturally occurring microRNA cluster composition, the cluster comprising:
   (i) a 5' flanking sequence;
   (ii) two or more microRNA hairpin domains, wherein the two or more hairpin domains are separated by one or more spacer sequences;
   (iii) two or more pairs of acceptor sites attached to the two or more microRNA hairpin domains, wherein the two or more pairs of acceptor sites are heterologous to said microRNA hairpin domains; and
   (iv) a 3' flanking sequence.

2. The composition of claim 1, wherein the two or more hairpin domains of the microRNA cluster comprise a stem domain and a loop domain, wherein the stem domain comprises a biologically active sequence.

3. The composition of claim 2, wherein the biologically active sequence is antisense or partially antisense to a target sequence.

4. The composition of claim 1, wherein the two or more hairpin domains of the microRNA cluster are heterologous to the microRNA cluster.

5. The composition of claim 1, wherein the two or more hairpin domains comprise miR-128 and miR-124 hairpin domains.

6. The composition of claim 1, wherein the microRNA cluster comprises three or more microRNA hairpin domains.

7. The composition of claim 6, wherein the three or more microRNA hairpin domains comprise miR-128, miR-124, and miR-137 hairpin domains.

8. The composition of claim 1, wherein the microRNA cluster comprises six microRNA hairpin domains.

9. The composition of claim 8, wherein the six microRNA hairpin domains comprise miR-128, miR-124, miR-137, miR-7, miR-218, and miR-34 hairpin domains.

10. The composition of claim 1, wherein the one or more spacer sequences separating the two or more hairpin domains are spacer sequences homologous to a miR-17-92 cluster.

11. The composition of claim 1, wherein the one or more spacer sequences separating the two or more hairpin domains are spacer sequences heterologous to a miR-17-92 cluster and comprise a non-coding RNA sequence, wherein the noncoding RNA sequence encodes an aptamer.

12. The composition of claim 11, wherein the non-coding RNA sequence encodes an aptamer that binds to a p50 protein.

13. The composition of claim 1, wherein: (i) the 5' flanking sequence comprises a miR-128 5' flanking sequence a microRNA sponge sequence, or a microRNA sponge sequence that is fully or partially antisense to a miR-21 target sequence, and/or (ii) the 3' flanking sequence comprises a miR-128 3' flanking sequence.

14. The composition of claim 1, wherein at least one hairpin domain is heterologous with respect to the 5' flanking sequence, or wherein at least one hairpin domain is heterologous with respect to the 3' flanking sequence, or wherein at least one hairpin domain is heterologous with respect to the one or more spacer sequences.

15. The composition of claim 1, wherein the two or more pairs of acceptor sites attached to the two or more microRNA hairpin domains each comprise a 5' acceptor site attached at its 3' end to the 5' end of the two or more microRNA hairpin domains and a 3' acceptor site attached at its 5' end to the 3' end of the two or more microRNA hairpin domains, wherein the 5' acceptor site and/or the 3' acceptor site comprises 3-21 nucleotides.

16. The composition of claim 1, wherein the microRNA cluster comprises:
   a miR-128 5' flanking sequence, a miR-128 hairpin domain, a first miR-17-92 spacer sequence, a miR-124 hairpin domain, a second miR-17-92 spacer sequence, a miR-137 hairpin domain, and a miR-128 3' flanking sequence.

17. The composition of claim 1, wherein the microRNA cluster comprises:
   a 5' flanking sequence comprising a microRNA sponge sequence that is fully or partially antisense to a miR-21 target sequence, a miR-128 hairpin domain, a first spacer sequence encoding an aptamer that binds to a p50 protein, a miR-124 hairpin domain, a second spacer sequence comprising a miR-17-92 spacer sequence, a miR-137 hairpin domain, and a miR-128 3' flanking sequence.

18. The composition of claim 1, wherein the microRNA cluster comprises:
   a miR-128 5' flanking sequence, a miR-128 hairpin domain, a first miR-17-92 spacer sequence, a miR-124 hairpin domain, a second miR-17-92 spacer sequence, a miR-137 hairpin domain, a third miR-17-92 spacer sequence, a miR-7 hairpin domain, a fourth miR-17-92 spacer sequence, a miR-218 domain, a fifth miR-17-92 spacer sequence, a miR-34 hairpin domain, and a miR-128 3' flanking.

19. An expression vector comprising a non-naturally occurring microRNA cluster composition, the cluster comprising:
   (i) a 5' flanking sequence;
   (ii) two or more microRNA hairpin domains, wherein the two or more hairpin domains are separated by one or more spacer sequences;
   (iii) two or more pairs of acceptor sites attached to the two or more microRNA hairpin domains, wherein the two or more pairs of acceptor sites are heterologous to said microRNA hairpin domains; and
   (iv) a 3' flanking sequence.

20. The vector of claim 19, wherein the vector is a plasmid or a virus.

21. The vector of claim 20, wherein the virus is a viral vector selected from the group consisting of: a lentiviral vector, an adeno-associated viral vector (AAV), or a replicating retroviral vector.

22. A method of treating a disease in a subject in need thereof, the method comprising administering to the subject an expression vector comprising a non-naturally occurring microRNA cluster composition, the cluster comprising:
   (i) a 5' flanking sequence;
   (ii) two or more microRNA hairpin domains, wherein the two or more hairpin domains are separated by one or more spacer sequences;
   (iii) two or more pairs of acceptor sites attached to the two or more microRNA hairpin domains, wherein the two or more pairs of acceptor sites are heterologous to said microRNA hairpin domains; and
   (iv) a 3' flanking sequence.

23. The method of claim 22, wherein the expression vector is administered to the subject as part of a targeted delivery system, wherein the targeted delivery system is selected from a group consisting of liposomes, exosomes, virosomes, and nanoparticles.

24. The method of claim 22, wherein the expression vector is formulated for administration to autologous cells of the subject ex vivo, and the cells are then formulated for administration to the subject in vivo.

25. The method of claim 22, wherein the expression vector is formulated for administration to the subject by way of intravenous injection, intraperitoneal injection, oral ingestion, inhalation, intrathecal injection, intracerebroventricular injection, intraparenchymal injection, or intratumoral injection.

26. The method of claim 22, wherein the expression vector is formulated for administration to the subject in combination with a second therapeutic agent or a second therapeutic modality.

27. The composition of claim 1, wherein the 5' flanking sequence and/or the 3' flanking sequence comprises a microRNA sponge sequence.

28. The composition of claim 27, wherein the sponge sequence is antisense or partially antisense to a target microRNA sequence.

29. The composition of claim 28, wherein the target microRNA sequence is a miR-21 nucleotide sequence.

30. The expression vector of claim 19, wherein the 5' flanking sequence and/or the 3' flanking sequence comprises a microRNA sponge sequence.

31. The expression vector of claim 30, wherein the sponge sequence is antisense or partially antisense to a target microRNA sequence.

32. The expression vector of claim 31, wherein the target microRNA sequence is a miR-21 nucleotide sequence.

33. The method of claim 22, wherein the 5' flanking sequence and/or the 3' flanking sequence comprises a microRNA sponge sequence.

34. The method of claim 33, wherein the sponge sequence is antisense or partially antisense to a target microRNA sequence.

35. The method of claim 34, wherein the target microRNA sequence is a miR-21 nucleotide sequence.

\* \* \* \* \*